(12) United States Patent
Aruffo et al.

(10) Patent No.: US 6,376,459 B1
(45) Date of Patent: Apr. 23, 2002

(54) INHIBITING B CELL ACTIVATION WITH SOLUBLE CD40 OR FUSION PROTEINS THEREOF

(75) Inventors: Alejandro A. Aruffo, Edmonds; Jeffrey A. Ledbetter, Seattle, both of WA (US); Ivan Stamenkovic, Brookline, MA (US); Randolph Noelle, Plainfield, NH (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 08/114,944

(22) Filed: Aug. 31, 1993

Related U.S. Application Data

(63) Continuation-in-part of application No. 07/835,799, filed on Feb. 14, 1992, now abandoned.

(51) Int. Cl.[7] ......................... A61K 38/02; A61K 38/04
(52) U.S. Cl. ...................... 514/2; 514/12; 514/885; 424/133.1; 530/350; 530/866; 530/868
(58) Field of Search .................... 424/130.1, 133.1, 424/134.1, 141.1, 143.1, 144.1; 530/300, 350, 395, 868, 866; 514/2, 8, 12, 885

(56) References Cited

U.S. PATENT DOCUMENTS

| 5,247,069 A | * | 9/1993 | Ledbetter et al. ............ 530/350 |
| 5,434,131 A | * | 7/1995 | Linsley et al. ................. 514/2 |
| 5,474,771 A | * | 12/1995 | Lederman et al. ........ 424/133.1 |

OTHER PUBLICATIONS

Bach Tips 14: 213–216 (1993).*
Stuber et al. J Exp Med. 183: 693–698 (1996).*
Larsen et al. Transplantation 61: 4–9 (1996).*
Biscone et al. Kidney International 48: 458–468 (1995).*
Gray et al. J Exp. Med. '80: 141–155 (1994).*
Stuart et al. Lab. Invest. 54: 1–3 (1986).*
Brennan Clin Exp Immunol. 97: 1–3 (1994).*
Harris et al. TIBTECH 11: 42–45 (1993).*
Konrad et al. Biological Barrier to Protein Delivery pp. 409–437 (1993).*
Borrebaeck et al. Immunol. Today.*
Durie et al. Science 261: 1328–1330 (1993).*
Noelle et al. PNAS 89: 6550–6554 (1992).*
Hollenbaugh et al. EMBO J, 11: 4313–4321 (1992).*
Alfons et al. J Exp Med 178: 1555–1565 (1993).*
Foy et al. J Exp Med 178: 1567–1575 (1993).*
Clark et al. Ann. Rev. Immunol. 9: 97–127 (1991).*
Clark et al. PNAS 83: 4494–4498 (1986).*
Dorken et al. Leukocyte Typing IV pp. 90–91 (1989).*
Aruffo et al. Cell 61: 1303–1313 (1990).*
Stamenkovic et al. EMBO J. 8: 1403–1410 (1989).*

* cited by examiner

*Primary Examiner*—Phillip Gambel
(74) *Attorney, Agent, or Firm*—Joan E. Switzer

(57) ABSTRACT

The present invention relates to a counter-receptor, termed CD40CR, for the CD40 B-cell antigen, and to soluble ligands for this receptor, including fusion molecules comprising at least a portion of CD40 protein. It is based, at least in part, on the discovery that a soluble CD40/immunoglobulin fusion protein or antibody specific for gp39 on T cells was able to inhibit helper T-cell mediated B-cell activation by binding to a novel 39 kD protein receptor on helper T-cell membranes. The present invention provides for a substantially purified CD40CR receptor; for soluble ligands of CD40CR, including antibodies as well as fusion molecules comprising at least a portion of CD40 protein; and for methods of controlling B-cell activation which may be especially useful in the treatment of allergy or autoimmune disease, including graft-versus-host disease and rheumatoid arthritis.

12 Claims, 43 Drawing Sheets

Figure 1A:
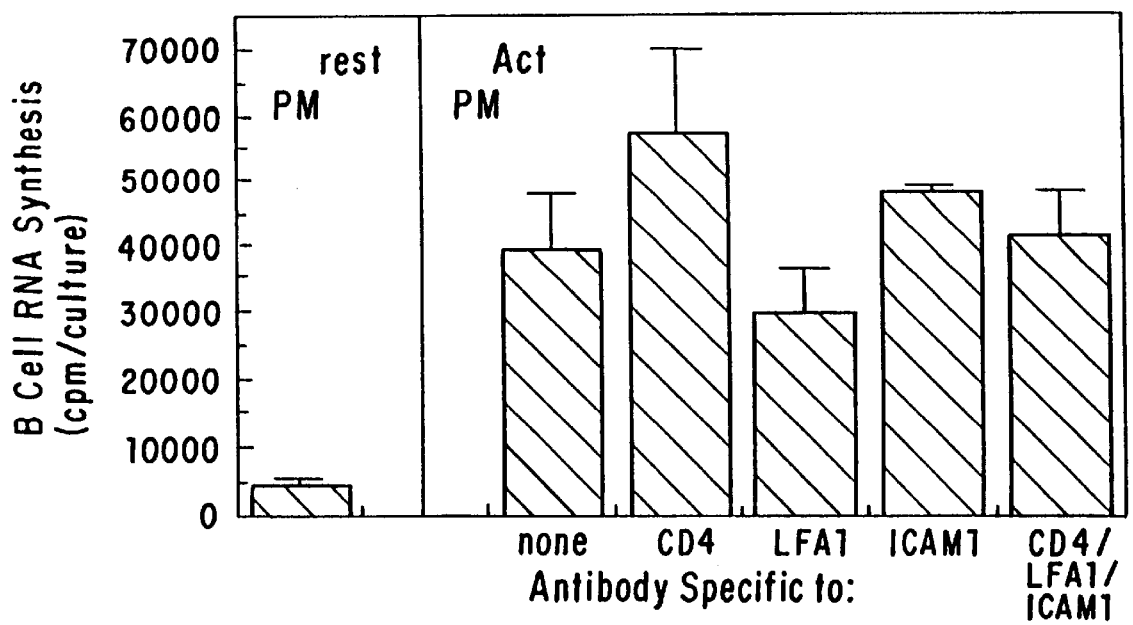

| Staining Ab or Fusion Protein | Blocking Ab | Resting $T_h$ | Activated $T_h$ |
|---|---|---|---|
| CD40 (50 µg/ml) | --- | 4.9 | 56.5 |
| MR1 (50 µg/ml) | --- | 5.7 | 61.8 |
| CD40 (50 µg/ml) | MR1 (50 µg/ml) | 5.0 | 11.7 |
| CD40 " " | MR1 (25 µg/ml) | --- | 20.7 |
| CD40 " " | MR1 (10 µg/ml) | --- | 30.3 |
| CD40 " " | MR1 ( 5 µg/ml) | --- | 49.5 |
| CD40 " " | α-α,β (50 µg/ml) | --- | 63.0 |

```
  1 GCCTCGGCTCGGGCGCCCCAGTGGTCCTCCTCACCTCGGCACATGGTTCGTCTGCCCCTCTGCCAGTGCGTCCTCTGGGGCTGCTGCTGACCGCTGTCCATCCAGAACCACCCACTG
    1                       M  V  R  L  P  L  Q  C  V  L  W  G  C  L  L  T  A  V  H  P  E  P  P  T  A

121 CATGCAGAGAAAAACAGTACCTAATAAACAGTCAGTGCTGTCTTTTGTGCCAGCCAGACAGAAACTGTGACTGCACAGAGTTCACTGAAACGGAATGCCTTCCTGCCGTGAAA
 26  C  R  E  K  Q  Y  L  I  N  S  Q  C  C  S  L  C  Q  P  G  G  Q  K  L  V  S  D  C  T  E  F  T  E  T  E  C  L  P  C  G  G  E  S

241 GCGAATTCCTAGACACCTGGAACAGAGAGGCTTGCCACCAGCACAAATACTGCGACCCCAACCTAGGCTTCCGGGTCCAGCAGAAGGGCACCTCAGCAAACAGACACCATCTGCACCT
 66  E  F  L  D  T  W  N  R  E  T  H  C  H  Q  H  K  Y  C  D  P  N  L  G  L  R  V  Q  Q  K  G  T  S  E  T  D  T  I  C  T  C

361 GTGAAGAAGGCTGCCACTGTAGACGTGAGGCCTGTCCACCGCTCATGCCCGCTCATGTCTACAGGGCTTTCTGATACCATCTGCGAGC
106  E  E  G  W  H  C  T  S  E  A  C  E  S  C  V  L  H  R  S  C  S  P  G  F  G  V  K  Q  I  A  T  G  V  S  D  T  I  C  E  P

481 CCTGCCCAGTCGGCTTCTCTCCAAATGTCATCTGCTTTCGAAAAATGTCACCCTTGGACAAGACTGTGCAACAGCAGCACAAACAGACTGATGTTG
146  C  P  V  G  F  F  S  N  V  S  S  A  F  E  K  C  H  P  W  T  S  C  E  T  K  D  L  V  V  Q  Q  A  G  T  N  K  T  D  V  V
                                 --CHO--                                                                --CHO--

601 TCTGTGGTCCCCAGGATCGGCTGAGAGCCCTGGTGGTCATCCCCATCATCTCTGTTTCCATCCTCTTTGCCATCCTCTTTGCTCTCTTTATCAAAAAGGTGGCCAAGAAGCCAACCAATA
186  C  G  P  Q  D  R  L  R  A  L  V  V  I  P  I  I  F  G  I  L  F  A  I  L  L  V  L  V  F  I  K  K  V  A  K  K  P  T  N  K

721 AGGCCCCCCACCCCAAGCAGGAACCCCCAGGAGATCTTCCTGCTCCAACACTGCTCCAGTGCAGGAGACTTTACATGGATGCCAGCCGGTCACCGGAGG
226  A  P  H  P  K  Q  E  P  Q  E  I  N  F  P  D  D  L  P  G  S  N  T  A  A  P  V  Q  E  T  L  H  G  C  Q  P  V  T  Q  E  D

841 ATGGCAAAGAGAGTCGGCATCTCAGTGCAGGAGCTCAGTGCCAGTGGGCCACGTGGGCAAAACAGGCAGTTGGCCCAGAGAGCCTGGTGCTGCTGCTGCAGGGT
266  G  K  E  S  R  I  S  V  Q  E  R  Q

901 GCAGGCAGAAGCGGGAGCTATGCCCAGTCAGTGCCAGCCCTC
```

FIG.8A

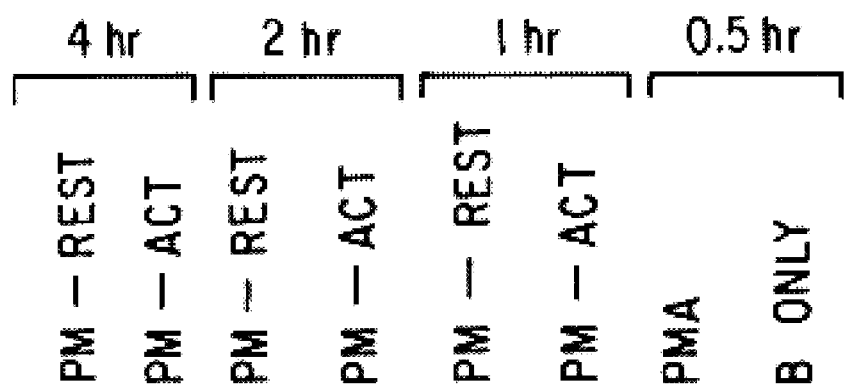
FIG. 24

P-TYR

ERK

INHIBITING B CELL ACTIVATION WITH SOLUBLE CD40 OR FUSION PROTEINS THEREOF

The present application is a continuation-in-part of U.S. patent application Ser. No. 07/835,799, filed Feb. 14, 1992 (abandoned), which has been refiled as Continuation application Ser. No. 08/338,975 on Nov. 14, 1994, each of which is incorporated by reference herein in its entirety.

1. INTRODUCTION

The present invention relates to a counter-receptor, termed CD40CR, (also known as CD40 ligand) for the CD40 B-cell antigen, and to soluble ligands for this receptor, including fusion molecules comprising at least a portion of CD40 protein. It is based, at least in part, on the discovery that a soluble CD40/immunoglobulin fusion protein or antibody specific for gp39 on T cells was able to inhibit helper T-cell mediated B-cell activation by binding to a novel 39 kD protein receptor on helper T-cell membranes. The present invention provides for a substantially purified CD40CR receptor; for soluble ligands of CD40CR, including antibodies as well as fusion molecules comprising at least a portion of CD40 protein; and for methods of controlling B-cell activation which may be especially useful in the treatment of allergy or autoimmune disease, including graft-versus-host disease (GVHD) and rheumatoid arthritis.

2. BACKGROUND OF THE INVENTION

Studies by Mitchison, Benacerraf and Raff first suggested that physical interactions between $T_h$ and B-cells were essential in the development of humoral immune responses. Later studies documented that $T_h$ formed physical conjugates with class II major histocompatibility complex (MHC) compatible, antigen-presenting B-cells (Vitetta et al., (1987) *Immunol. Rev.* 99:193–239) and that it was the B-cells within these conjugates that responded to $T_h$ (Bartlett et al., (1989) *J. Immunol.* 143:1745–1754). With the discovery that $T_h$-derived lymphokines exerted potent growth and differentiative effects on B-cells, it was proposed that soluble factor(s) released in proximity by activated $T_h$ mediated the activation of the interacting B-cell. However, none of the molecularly cloned lymphokines, alone or in combination, manifested the ability to induce B-cell cycle entry. Unlike soluble factors, plasma membrane fractions from activated $T_h$ induced B-cell cycle entry (Hodgkin et al., (1990) *J. Immunol.* 145:2025–2034; Noelle et al., (1991) *J. Immunol.* 146:1118–1124). Studies using purified plasma membrane fractions from activated $T_h$ suggested that a protein expressed on the membrane of activated $T_h$ was responsible for initiating humoral immunity (Noelle et al., (1991) *J. Immunol.* 146:1118–1124; Bartlett et al., (1990) *J. Immunol.* 145:3956–3962).

Purified plasma membranes from activated $T_h$ ($PM^{Act}$) have been used to investigate the nature of this effector function (Hodgkin et al. (1990) *J. Immunol.* 145:2025–2034; Noelle et al., (1991) *J. Immunol.* 146:1118–1124). $PM^{Act}$ from activated $T_h$, but not resting $T_h$ ($PM^{rest}$) expressed an activity that induced B-cell cycle entry in an antigen-nonspecific, class II-unrestricted manner. In addition, it was shown that the activity expressed by $PM^{Act}$ required 4–6 hours of activation, de novo RNA synthesis and was protein in nature (Bartlett et al., (1990) *J. Immunol.* 145:3956–3962).

3. SUMMARY OF THE INVENTION

The present invention relates to a counter-receptor, termed CD40CR, for the CD40 B-cell antigen, and to soluble ligands for this receptor, including fusion molecules comprising at least a portion of CD40 protein. It is based, at least in part, on the discovery that a soluble CD40/immunoglobulin fusion protein was able to inhibit helper T-cell mediated B-cell activation by binding to a novel 39 kD receptor protein (termed "CD40CR" for CD40 counter-receptor) on helper T-cell membranes, and on the discovery that a monoclonal antibody, termed MR1, directed toward this 39 kD receptor was able to inhibit helper T-cell mediated activation of B-cells.

The present invention provides for a substantially purified CD40CR receptor; for soluble ligands of CD40CR, including antibodies as well as fusion molecules comprising at least a portion of CD40 protein; and for methods of controlling B-cell activation.

In particular embodiments of the invention, B-cell activation in a subject may be inhibited by contacting helper T cells of the subject with effective amounts of a soluble ligand of CD40CR. Such inhibition of B-cell activation by interfering with CD40CR of helper T cells may be especially useful in the treatment of allergy or autoimmune disease, including, in particular embodiments, GVHD and rheumatoid arthritis.

One advantage of the present invention is that it enables immune intervention in an aspect of the immune response which is not antigen specific. Many current therapies for allergy include desensitization to particular antigens, and require that each patient be tested in order to identify antigens associated with sensitivity. As a practical matter, exhaustive analysis of a patient's response to each and every potential allergen is virtually impossible. Furthermore, in most autoimmune conditions, the causative antigen is, generally, unknown or even irrelevant to the disease process. The present invention, which relates to the antigen nonspecific CD40/CD40CR interaction, circumvents the need to characterize the antigen associated with allergy or autoimmunity. Therefore, the present invention may be used to particular advantage in the treatment of allergic conditions in which the immunogen is not known, or has multiple components, for example, in hay fever or in procainamide induced lupus. It may also be useful in acute treatment of immune activation, for example, in therapy for anaphylaxis.

3.1. ABBREVIATIONS

| | |
|---|---|
| Ig | immunoglobulin |
| mab | monoclonal antibody |
| ERK | Extracellular Signal Regulated Kinase |
| GαCh Ig | goat anti chicken Ig |
| GαM Ig | goat anti mouse Ig |
| GαRb Ig | goat anti rabbit Ig |
| HRPO | horse radish peroxidase |
| MARCKS | myristoylated alanine rich C-kinase substrate |
| mIg | membrane immunoglobulin |
| NGF | nerve growth factor |
| PAGE | polyacrylamide gel electrophoresis |
| PKA | protein kinase A |
| PKC | protein kinase C |
| PLC | phospholipase C |
| PMA | phorbol myristate acetate |
| $PM^{Act}$ | plasma membranes isolated from anti-CD3 activated $T_h$ |
| $PM^{Act}$ | plasma membranes prepared from activated helper T-cells |
| $PM^{rest}$ | plasma membranes prepared from resting helper T-cells |
| $PM^{rest}$ | plasma membranes isolated from resting |

-continued

3.1. ABBREVIATIONS

| | |
|---|---|
| | $T_h$ |
| PTK | protein tyrosine kinase |
| rIL4 | recombinant interleukin 4 |
| rIL5 | recombinant interleukin 5 |
| SN | supernatant |
| $T_h$ | helper T-cell |
| $T_h1$ | refers to D 1.6, a I-A$^d$-restricted, rabbit immunoglobulin specific clone |
| TNF | tumor necrosis factor |

4. BRIEF DESCRIPTION OF THE DRAWINGS

Figure 1B:
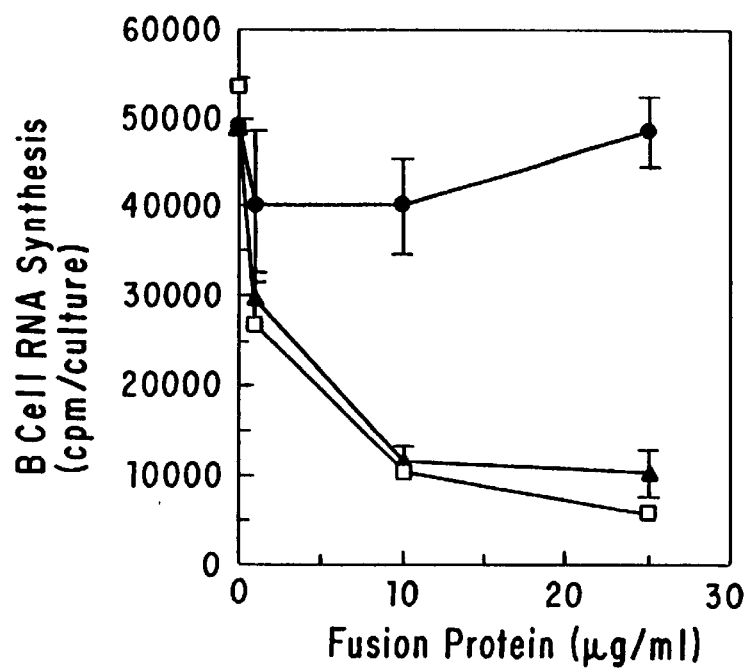
Figure 1C:
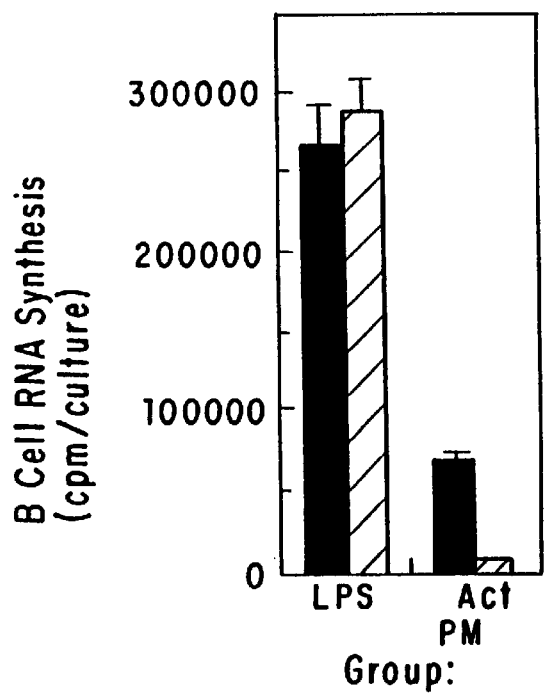

FIGS. 1A–1C Effect of monoclonal antibodies and CD40-Ig on the induction of B-cell RNA synthesis by PM$^{Act}$.

FIG. 1A. Resting B-cells were cultured with PM$^{rest}$ or PM$^{Act}$ from $T_h1$. 25 µg/ml of anti-CD4, anti-LFA-1 or anti-ICAM-1 or a combination of each of these (each at 25 µg/ml) was added to wells containing PM$^{Act}$, and B-cell RNA synthesis was measured by incorporation of [$^3$H]-uridine. B-cell RNA synthesis was assessed from 42 to 48 hours post-culture. Results presented are the arithmetic means of triplicate cultures+/–s.d., and are representative of 5 such experiments.

FIG. 1B. Resting B-cells were cultured with PM$^{Act}$ from $T_h1$ (●, ▲) or $T_h2$ (□). To the $T_h1$ PM$^{Act}$ containing cultures (●, ▲), increasing amounts of CD40-Ig (▲) or control protein CD7E-Ig(●) were added. To the $T_h2$ PM$^{Act}$ containing culture (□), increasing amounts of CD40-Ig were added. B-cell RNA synthesis was assessed from 42 to 48 hours post-culture. Results presented are the arithmetic means of triplicate cultures+/–s.d., and are representative of 3 such experiments.

FIG. 1C. Resting B-cells were cultured with LPS (50 µg/ml) or PM$^{Act}$. To cultures, CD40-Ig (25 µg/ml; hatched) or CD7E-Ig (25 µg/ml; solid) were added. RNA synthesis was determined as described in FIG. 1A. Results presented are the arithmetic mean of triplicate cultures+/–s.d., and are representative of 3 such experiments.

Figure 2A:
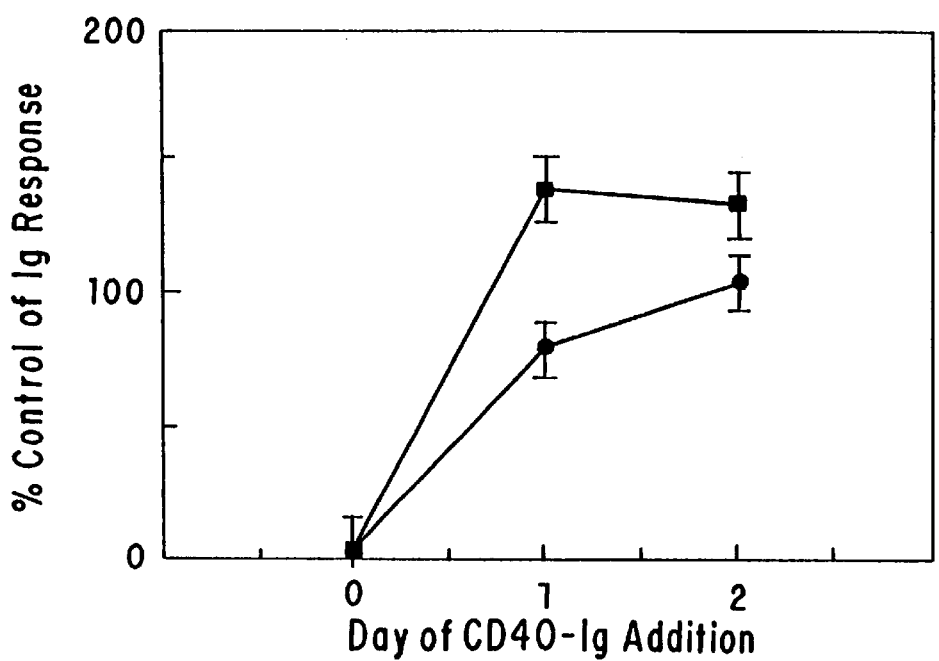
Figure 2B:
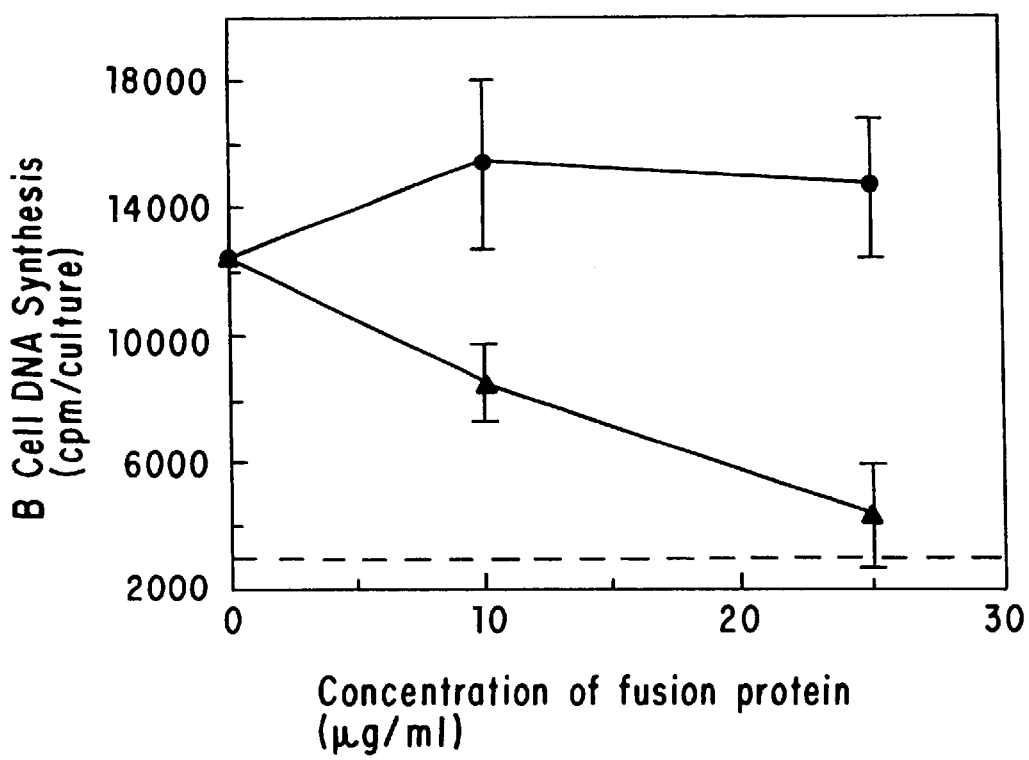

FIGS. 2A–2B. CD40-Ig inhibited B-cell differentiation and proliferation.

FIG 2A. Resting B-cells were cultured with PM$^{Act}$, rIL4 (10 ng/ml) and rIL5 (5 ng/ml). Either at the initiation of culture, or on days 1, 2 or 3 post-initiation of culture, CD40-Ig or CD7E-Ig (25 µg/ml) were added. On day six of culture, SN from individual wells were harvested and quantitated for IgM(■) and IgG,(●) using an anti-isotype specific ELISA, as described in (Noelle et al., (1991) *J. Immunol.* 146:1118–1124). In the presence of PM$^{Act}$, IL4 and IL5, (in the absence of added CD40-Ig) the concentrations of IgM and IgG$_1$ were 4.6 µg/ml and 126 ng/ml, respectively. Cultures which received CD7E-Ig (25 µg/ml) on Day 0 produced 2.4 µg/ml and 89 ng/ml of IgM and IgG$_1$, respectively. In the absence of IL4 and IL5, no IgM or IgG$_1$ was detected. Results are representative of 3 such experiments.

FIG. 2B. $T_h1$ were rested or activated with anti-CD3 for 16 hours, irradiated and cultured (1×10$^4$/well) with resting B-cells (4×10$^4$/culture) in the presence of IL4 (10 ng/ml). Between 0 and 25 µg/ml of CD40-Ig (▲) or CD7E-Ig (●) were added to cultures. From 66–72 hours post-culture, wells were pulsed with 1.0 µCi of [$^3$H]-thymidine and harvested. The dotted line indicates the response of B-cells to resting $T_h$. Results presented are the arithmetic mean of triplicate cultures+/–s.d., and are representative of 2 such experiments.

Figure 3A:
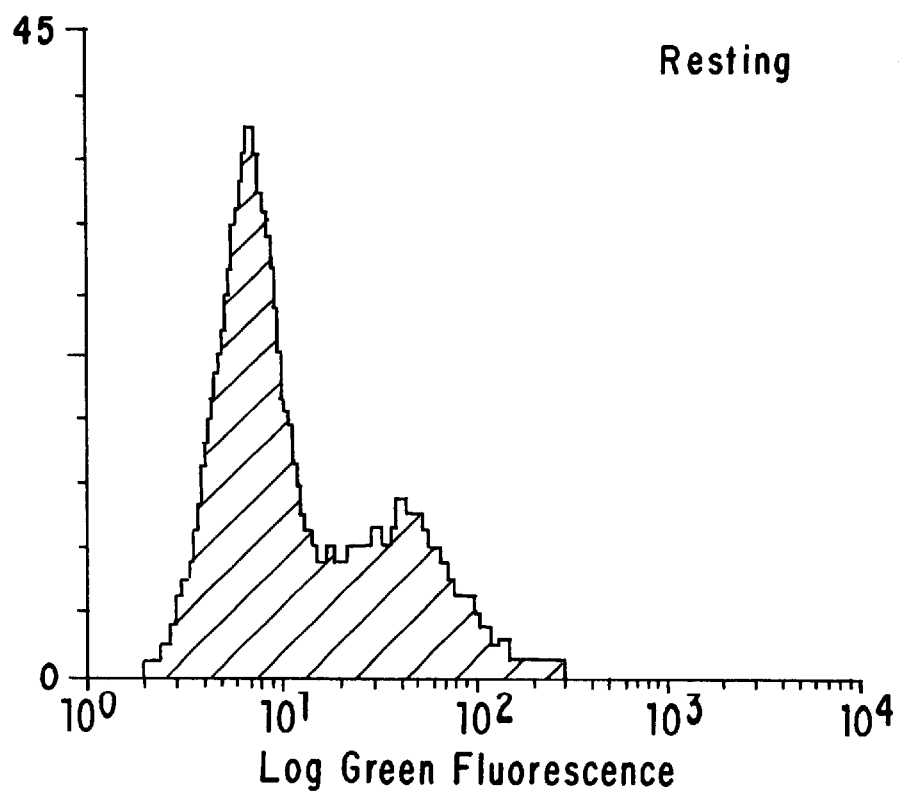
Figure 3B:
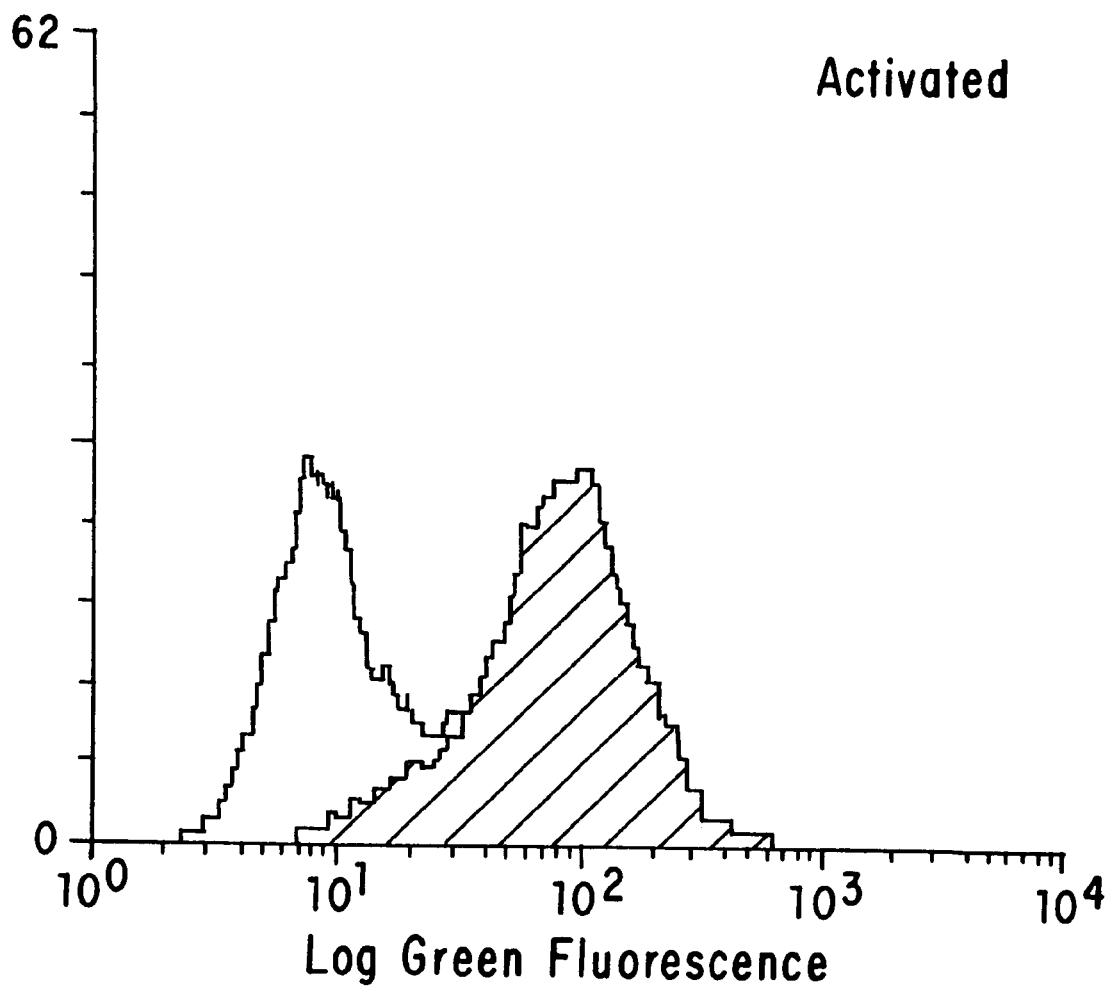

FIGS. 3A–3B. CD40-Ig detected a molecule expressed on activated, but not resting $T_h$. Resting (FIG. 3A) and activated (FIG. 3B) $T_h$ were harvested and incubated with fusion proteins for 20 minutes at 4° C., followed by FITC-conjugated goat anti-hIgG (25 µg/ml). Percentage positive cells and MFI were determined by analysis of at least 5000 cells/sample. Results are representative of 6 such experiments. CD40-Ig binding is indicated by a filled-in profile.

Figure 4:
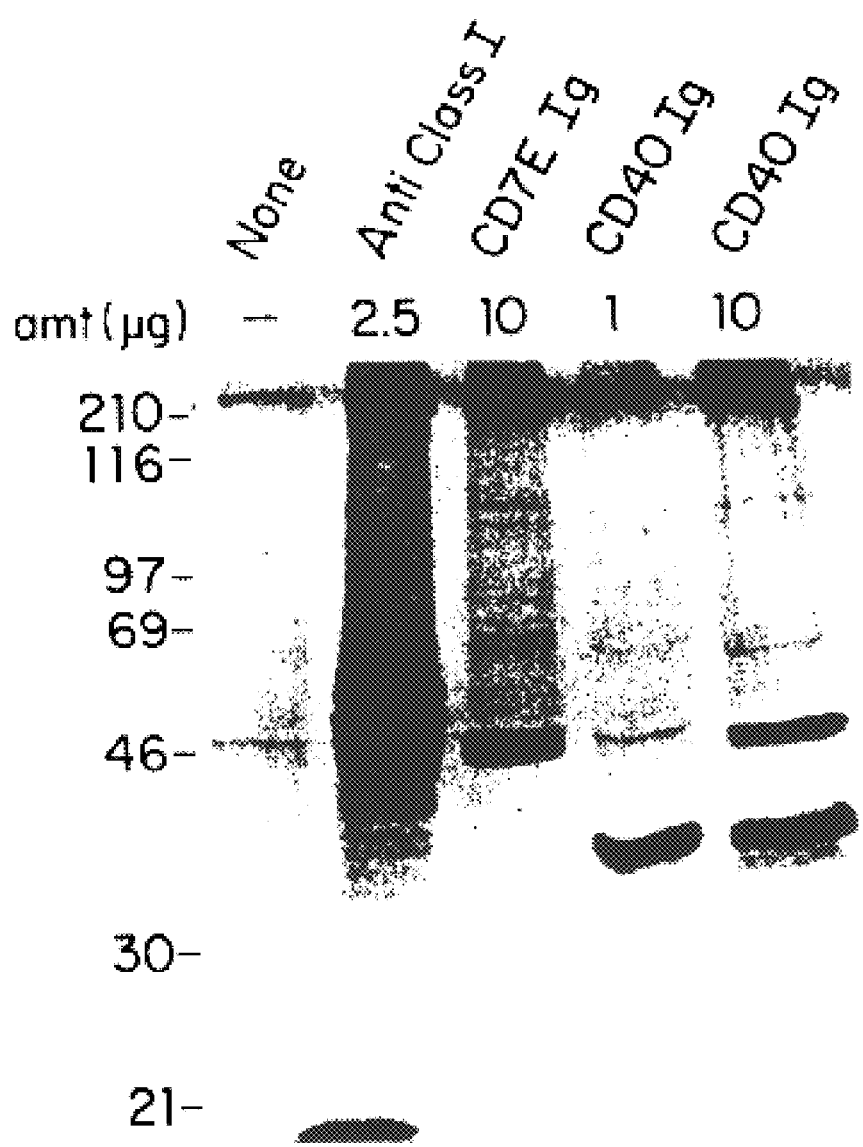

FIG. 4. CD40-Ig immunoprecipitated a 39 kD protein from lysate of activated $T_h1$. $T_h1$ were rested or activated with insolubilized anti-CD3 for 16 hours. [$^{35}$S]-labelled proteins from resting or activated $T_h$ were immunoprecipitated with purified antibodies or fusion proteins (1–10 µg). The gel profile is representative of 3 such experiments.

Figures 5A, 5B:
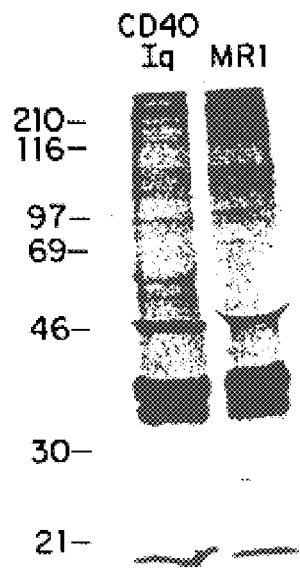

FIGS. 5A–5B. MR1 and CD40-Ig recognized the same molecule expressed on activated $T_h$.

FIG. 5A: Activated $T_h$ were fluorescently stained with MR1 or control Ig. To evaluate if CD40-Ig and MR1 competed for binding to activated $T_h$, graded concentrations of MR1 or control hamster Ig (anti-α/β TCR) were added together with anti-CD40 (20 µg/ml). After incubation for 20 minutes at 4° C., the samples were washed and incubated with FITC-conjugated, mab anti-human IgG$_1$. Results are representative of 3 such experiments.

FIG. 5B: Proteins from [$^{35}$S]-methionine-labelled, activated $T_h$ were immunoprecipitated with MR1 (10 µg/sample) or CD40-Ig (10 µg/sample) and resolved by PAGE and fluorography. Results presented are representative of 2 such experiments.

Figure 6:
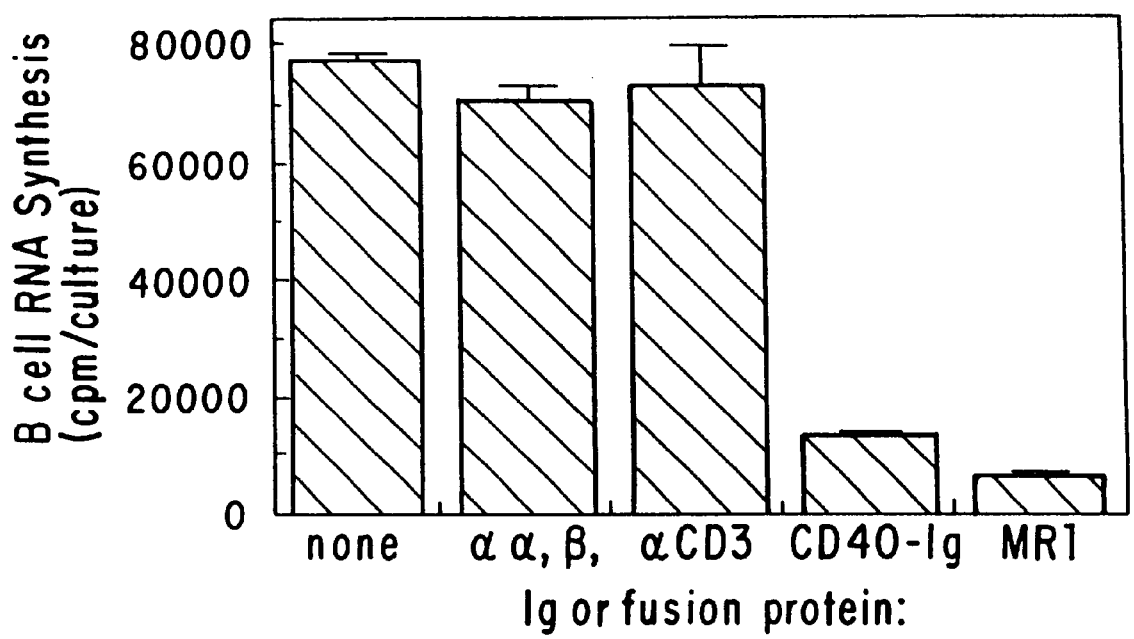

FIG. 6. A monoclonal antibody (mab), specific to the induced 39 Kd $T_h$ membrane protein, inhibited induction of B-cell RNA synthesis by PM$^{Act}$. Resting B-cells and PM$^{Act}$ were cultured with 10 µg/ml each of anti-α/β, anti-CD3, CD40-Ig or MR1. RNA synthesis was determined as described in FIGS. 1A–1C. Results are the arithmetic means of triplicate cultures+/–s.d., and are representative of 3 such experiments.

Figure 7A:
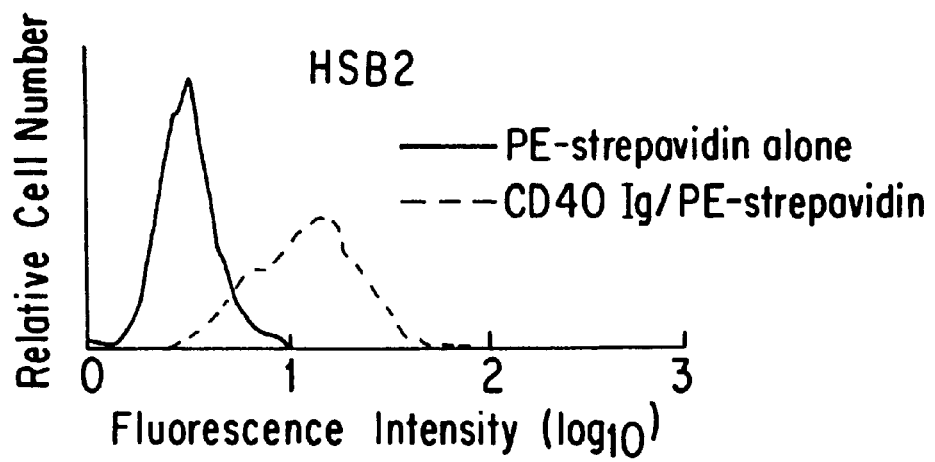
Figure 7B:
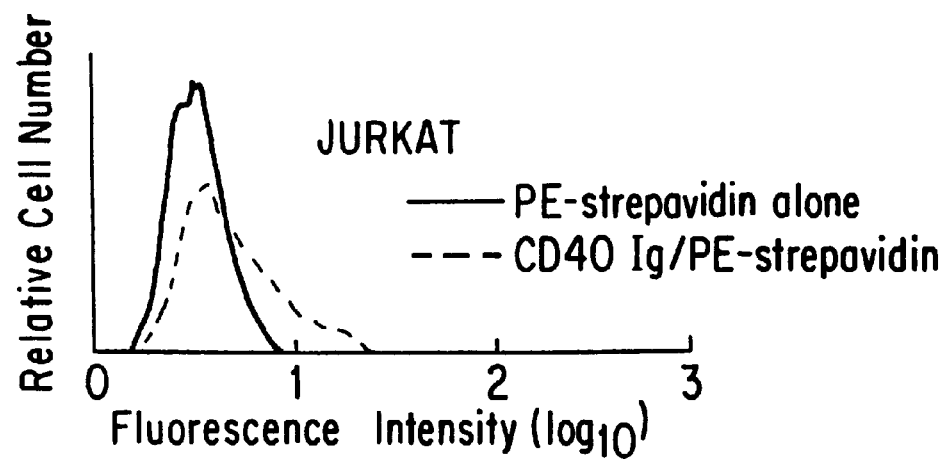
Figure 7C:
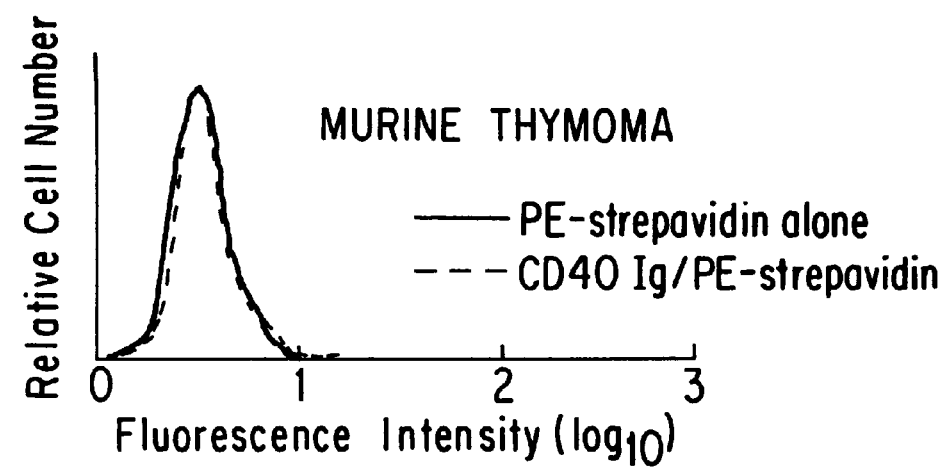

FIGS. 7A–7C. Binding of CD40-Ig to human cell lines. A variety of human T-cell lines were exposed to biotin-labelled CD40-Ig, and binding was evaluated by flow cytometry.

FIGS. 8A–8B.

FIG. 8A: Nucleotide sequence of CD40 cDNA from Stamenkovic et al., (1989) *EMBO J.* 8:1403–1410 (SEQ ID NOS. 1 & 2). The transmembrane region is underscored.

Figure 8B:
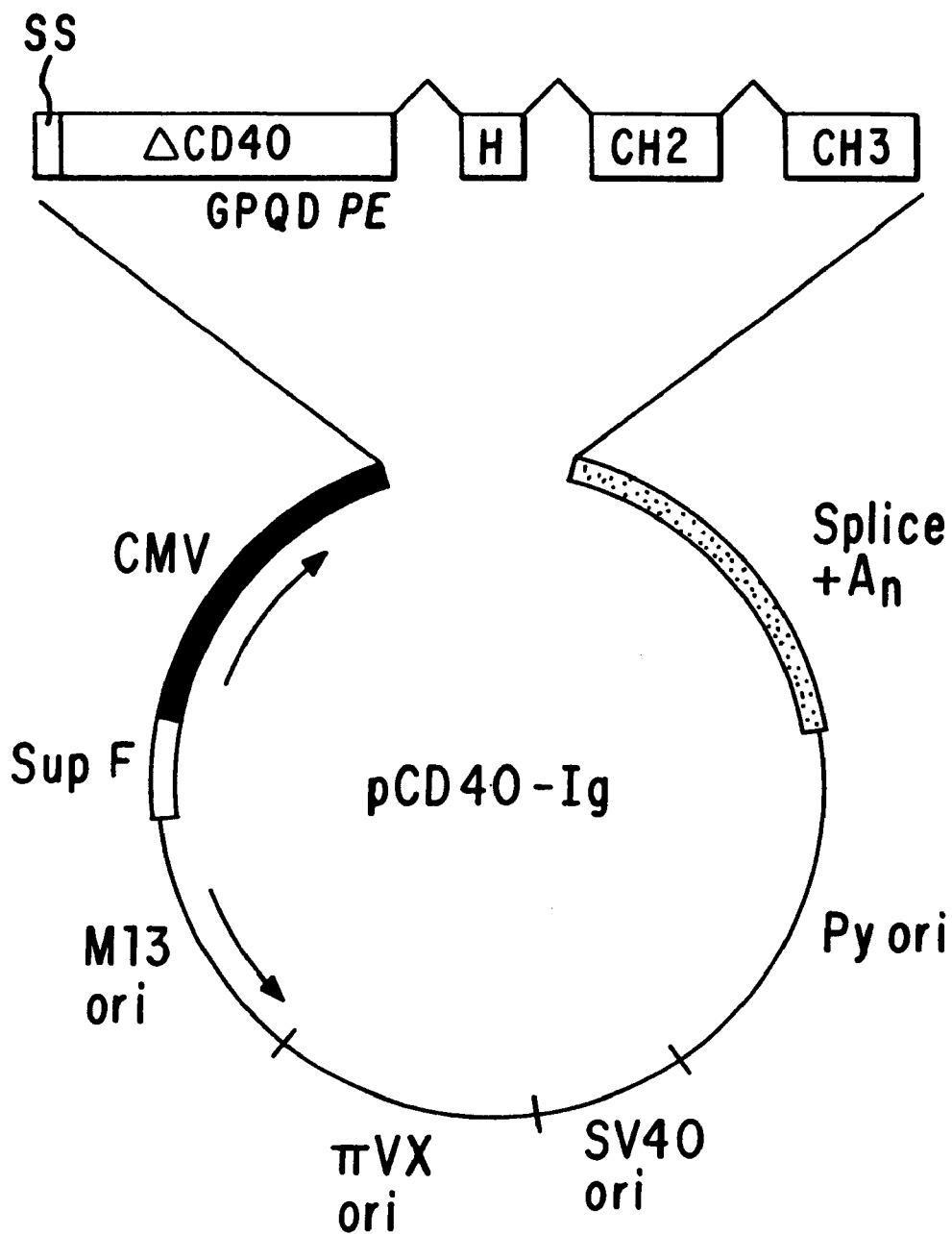

FIG. 8B: Schematic diagram of a plasmid that may be used to express CD40-Ig. The amino acid sequences at the site of fusion of Δ CD40 is shown below the diagrammed portion of CD40.

FIGS. 9A–9D. Immunohistochemical localization and characterization of gp39+ cells in lymphoid organs.

Figure 9A:
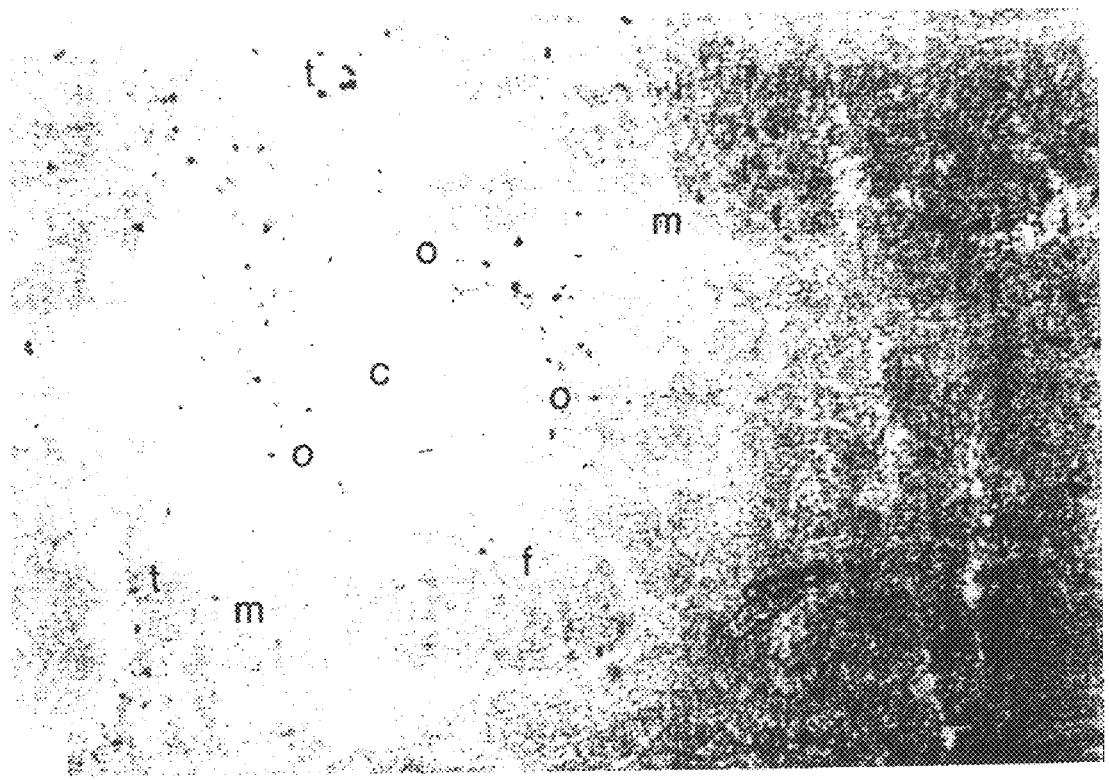

Cryostat sections of murine lymphoid tissue were incubated with specific-conjugates, followed by immunohistochemical revelation. Conjugates and substrates used are indicated between the square brackets. FIG. 9A) 4 days after secondary i.v. immunization with KLH; red stained cells are gp39$^+$ cells localized in outer-PALS (o), around the terminal arteriole (t) and in the follicle (f) of the spleen [MR1+RG7-HRP; AEC].

Figure 9B:
Figure 9C:
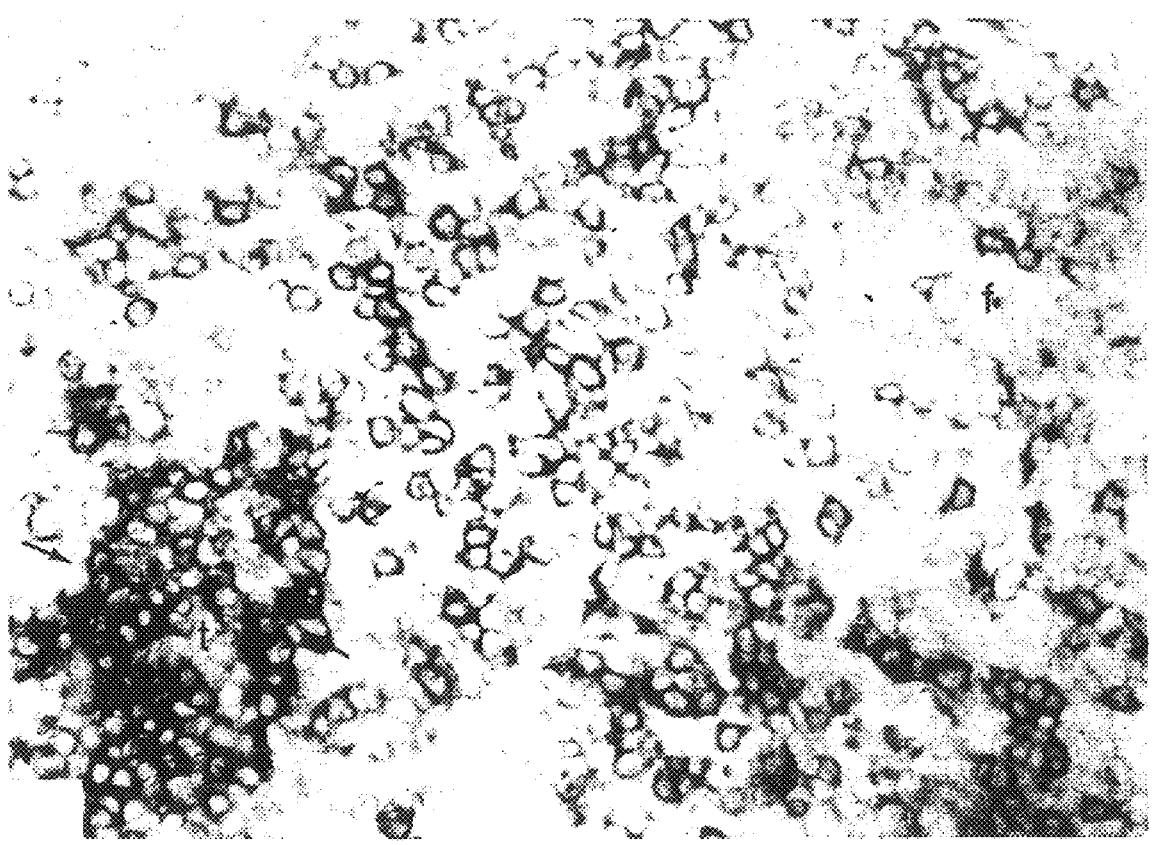

FIG. 9B) cryostat section of lymph node 6 days after secondary f.p. immunization with TNP-KLH; red stained cells are gp39+ cells localized in deep cortex and along the medullary cords. In this section no gp39+ cells are localized in the follicle (f) [MR1+RG7-HRP; AEC]. FIG. 9C) 3 days after KLH immunization; red membrane positive cells are CD4+ cells, while violet double staining cells are CD4+ expressing gp39 (arrow). (Note that CD4+ cells are present in the follicle (f), while CD4+ cells expressing gp39 are found around terminal arterioles (t) and not in the primary follicle (f) [L3T4-HRP, AEC; MR1-AP, Fast blue] FIG. 9D) 4 days after KLH immunization, red stained cells are gp39+ cells, turquoise stained cell are IL-4-PC, whereas violet stained cells are gp39+ cells producing IL-4 (arrows). [MR1-AP, Fast red; 11B11-β-Gal, X-Gal].

Figure 10A:
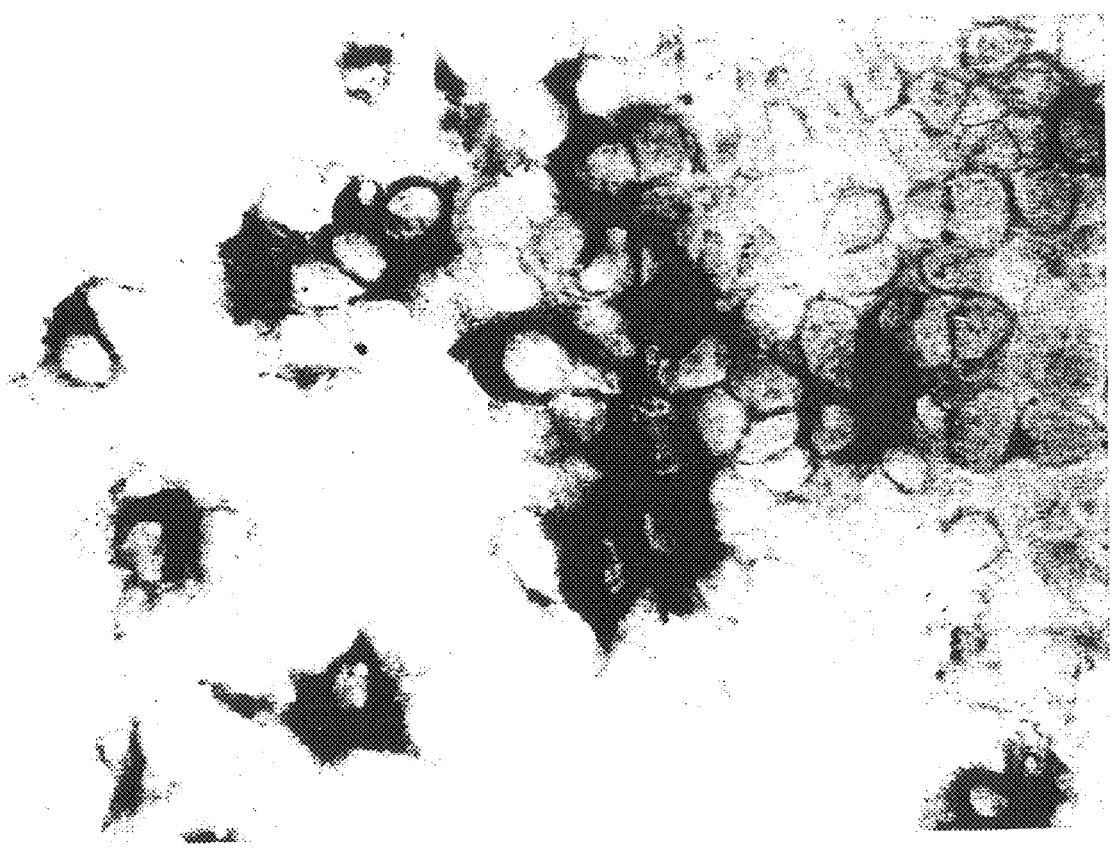
Figure 10B:
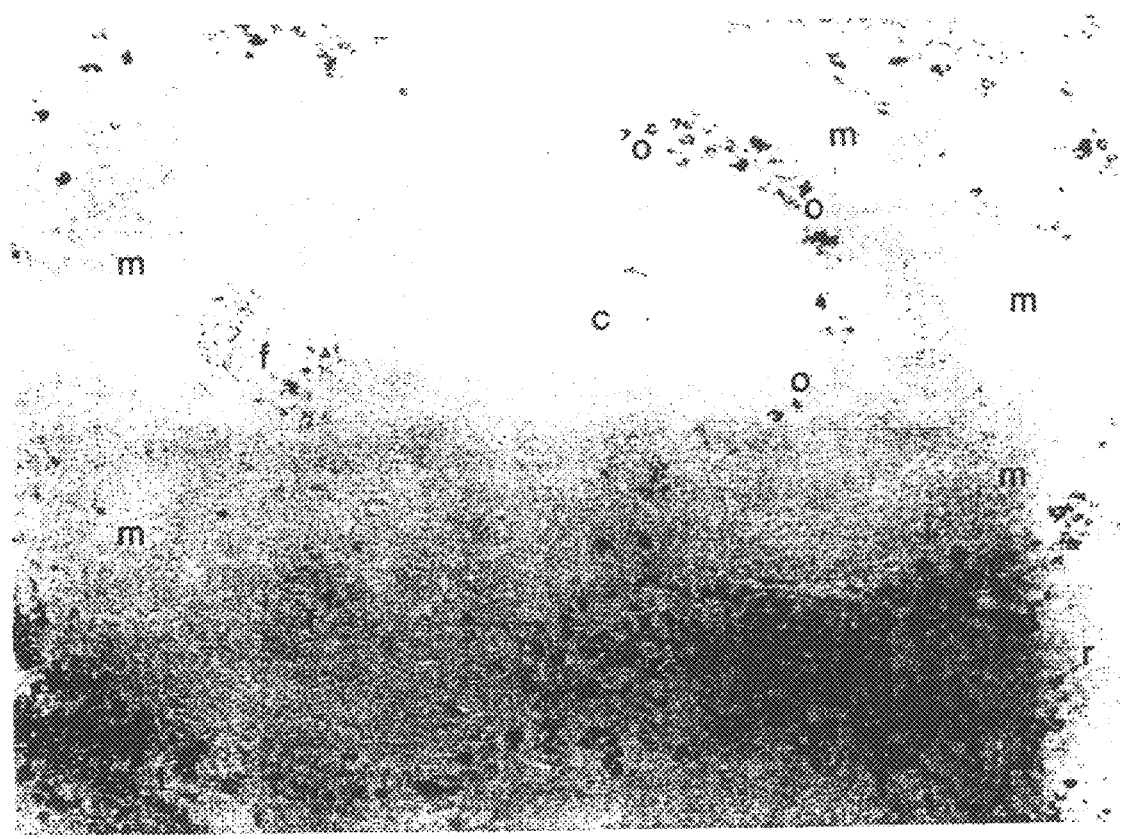

FIGS. 10A–10B. Immunohistochemical visualization of T-B cell interaction in the spleen.

a) Four days after secondary KLH immunization; KLH-AFC, stained red, were found in juxtaposition to gp39+ cells, stained blue [KLH-HRP, AEC; MR1-AP, Fast blue] FIG. 10B) Five days after TNP-Ficoll immunization; gp39+ cells, stained red, and TNP-AFC, stained blue, are found in the same compartments. (Note the gp39+ cells in close conjunction to TNP-AFC in outer-PALS and around TA, but not in follicles and marginal zone. Immune-complexes are found in the follicles) [TNP-AP, Fast blue; MR1+RG7-HRP, AEC]. c=central arteriole, f=follicle, m=marginal zone, o=outer-PALS, r=red pulp, t=lymphocyte sheath around terminal arteriole.

Figure 11A:
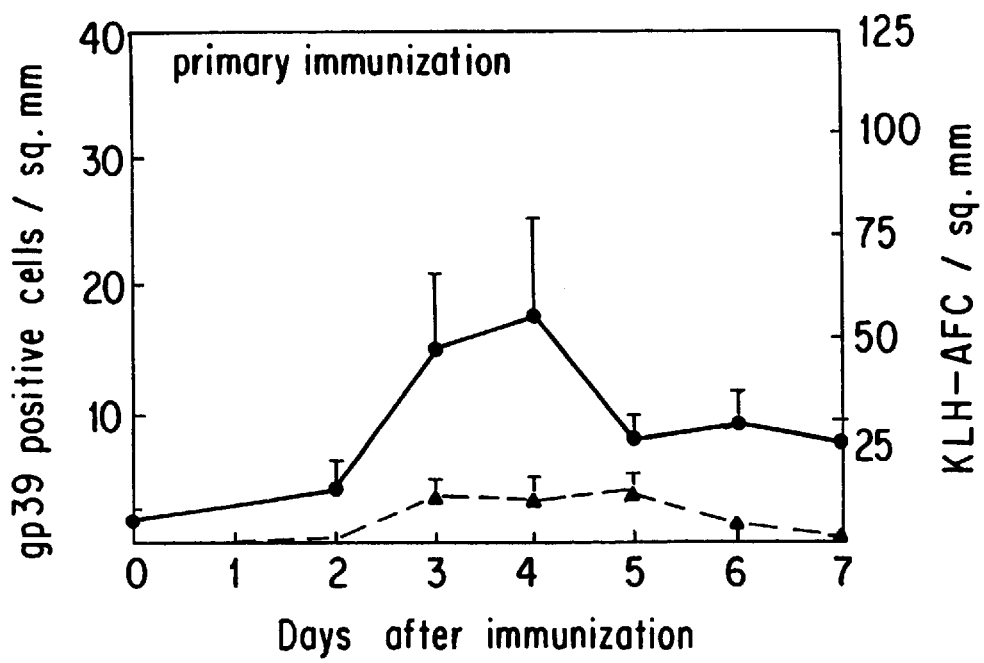
Figure 11B:
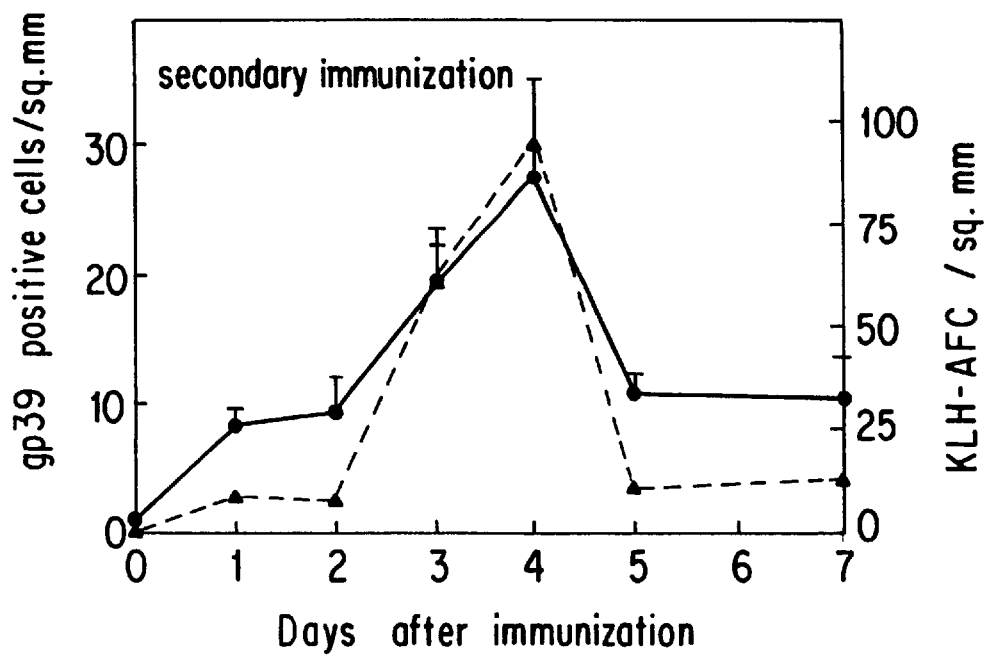

FIGS. 11A–11B. Kinetics of gp39-positive T cells and KLH-AFC after primary and secondary immunization with KLH. BCBA.F1 mice were injected i.v. with 100 μg KLH and sacrificed at the indicated time points. Another group of BCBA.F1 mice was injected with 100 μg of KLH, boosted 16 weeks later with 100 μg KLH i.v. and sacrificed at the indicated time points. Spleens were removed and immunohistochemistry and image analysis was performed as described in Materials and Methods section. Values represent mean±SD of number of positive cells per mm² from three mice. Closed triangles, KLH-AFC; closed circles, gp39-bearing cells.

Figure 12:
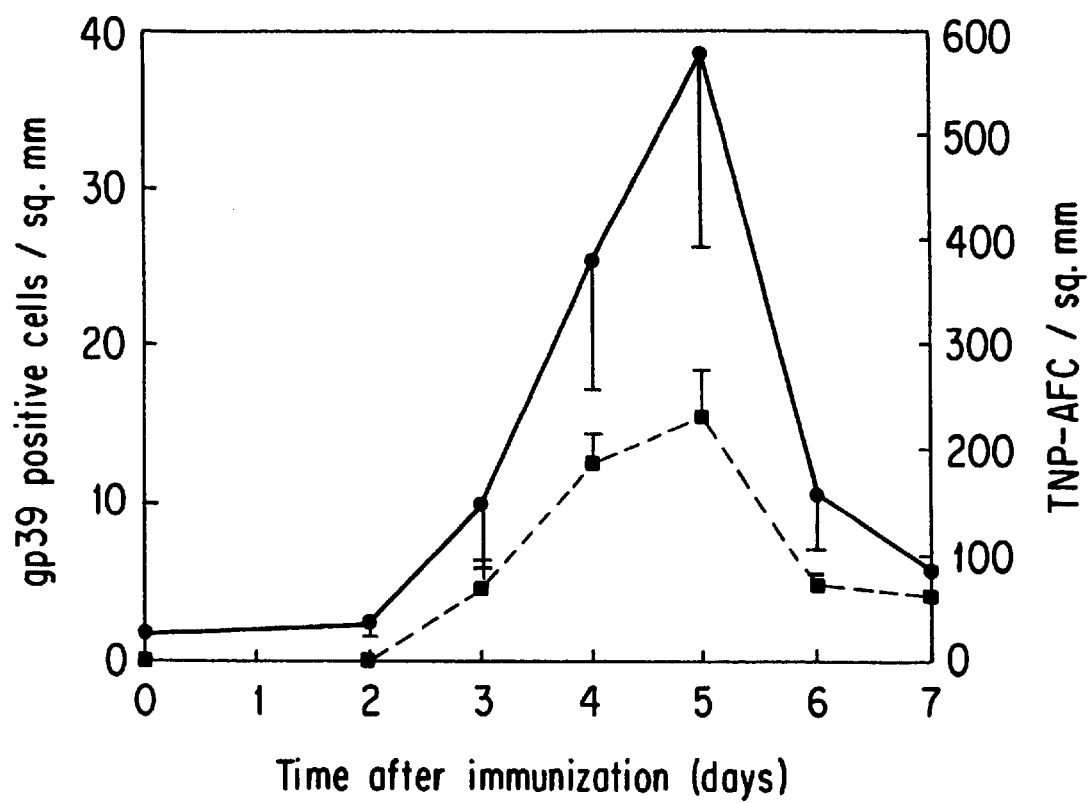

FIG. 12. Kinetics of gp39+ cells and TNP-AFC are superimposable after immunization with TNP-Ficoll.

BCBA.F1 mice were injected i.v. with 20 μg TNP-Ficoll and sacrificed at the indicated time points. Spleens were removed and immunohistochemistry and image analysis was performed as described in the Materials and Methods section. Values represent mean±SD of number of positive cells per mm² from three mice. Closed squares, TNP-AFC; closed circles, gp39-bearing cells.

Figure 13A:
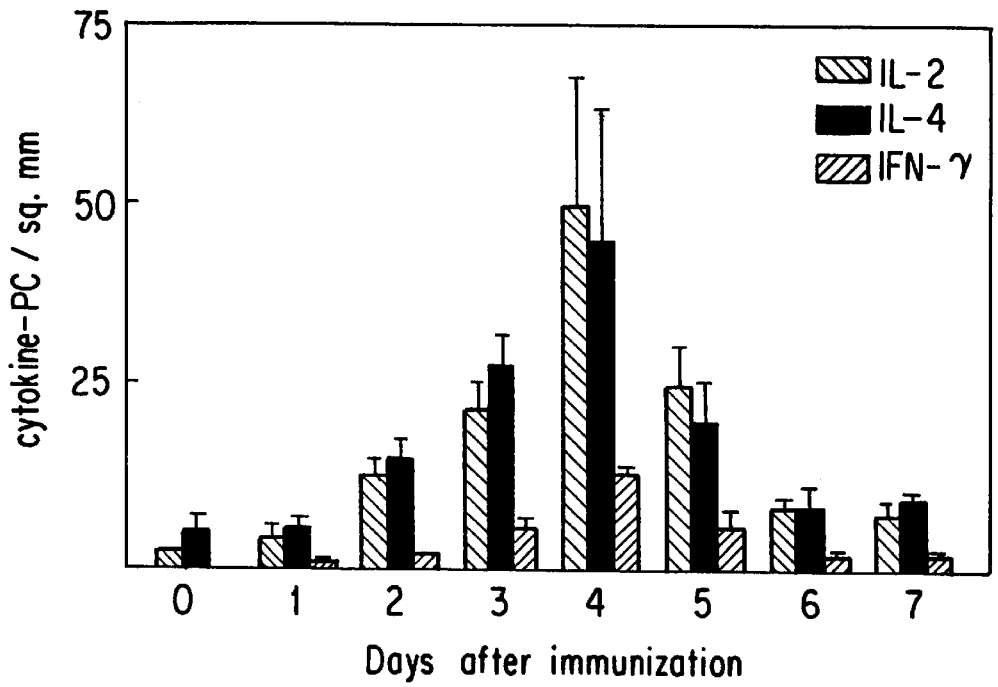
Figure 13B:
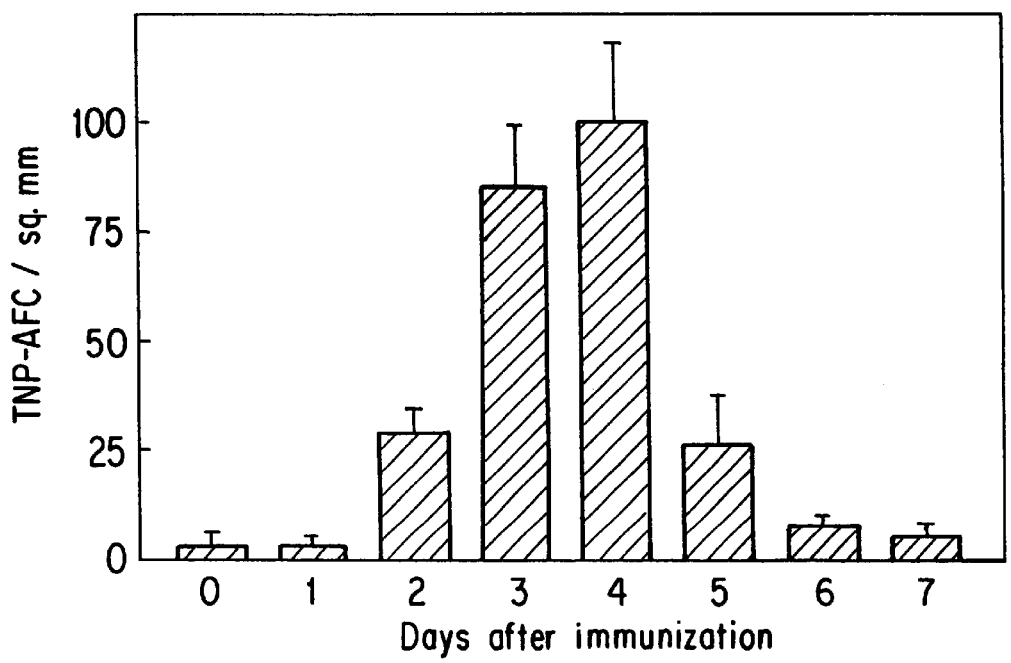

FIGS. 13A–13B. Cytokine-PC and TNP-AFC develop according to similar kinetics after immunization with TNP-KLH.

BCBA.F1 mice were injected i.v. with 100 μg TNP-KLH and sacrificed at the indicated time points. Spleens were removed and immunohistochemical demonstration of IL-2, IL-4, IFN-γ-PC and TNP-AFC was performed as described in Materials and Methods section. Values represent mean±SD of number of positive cells per mm² from three mice.

Figure 14:
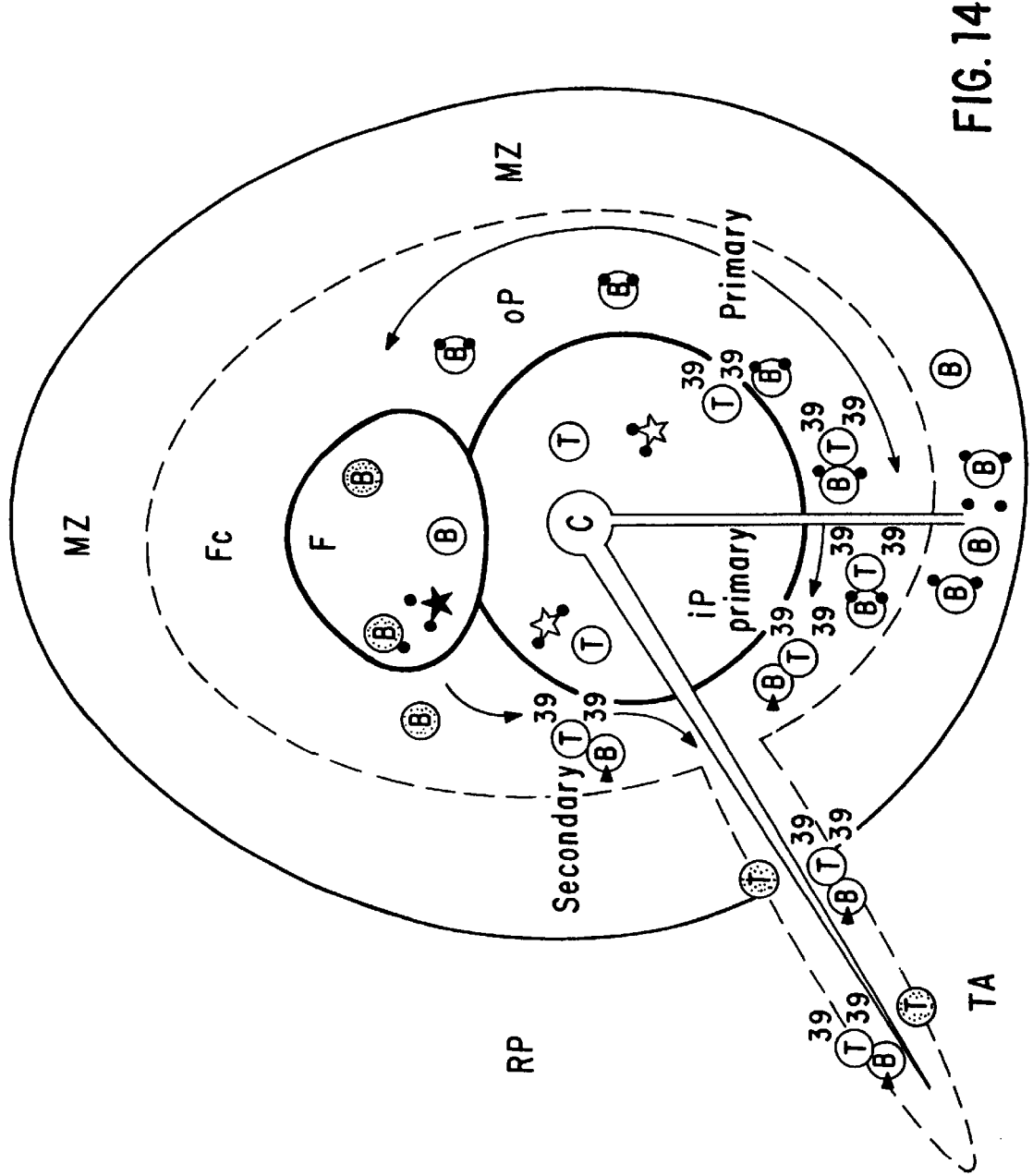

FIG. 14. Schematic representation of the activation and migration of T and B cells in the spleen during the TD immune response. Arrows indicate migration of B and T cells in the spleen. C=central arteriole, ip=inner-PALS, F=follicle, Fc=follicle corona, MZ=marginal zone, iP=inner-PALS, oP=outer-PALS, R=red pulp, S=sinus, ta=lymphocyte sheath around terminal arteriole.·=antigen, Ⓑ=resting B cell, Ⓑ=memory B cell, Ⓑ=differentiating antigen-specific B cell, xⒷ=antibody-forming B cell, Ⓣ=resting T cell, Ⓣ=activated antigen-specific T cell (gp39 positive), Ⓣ=cytokine-producing T cell, ★=FDC, ☆=IDC.

Figure 15A:
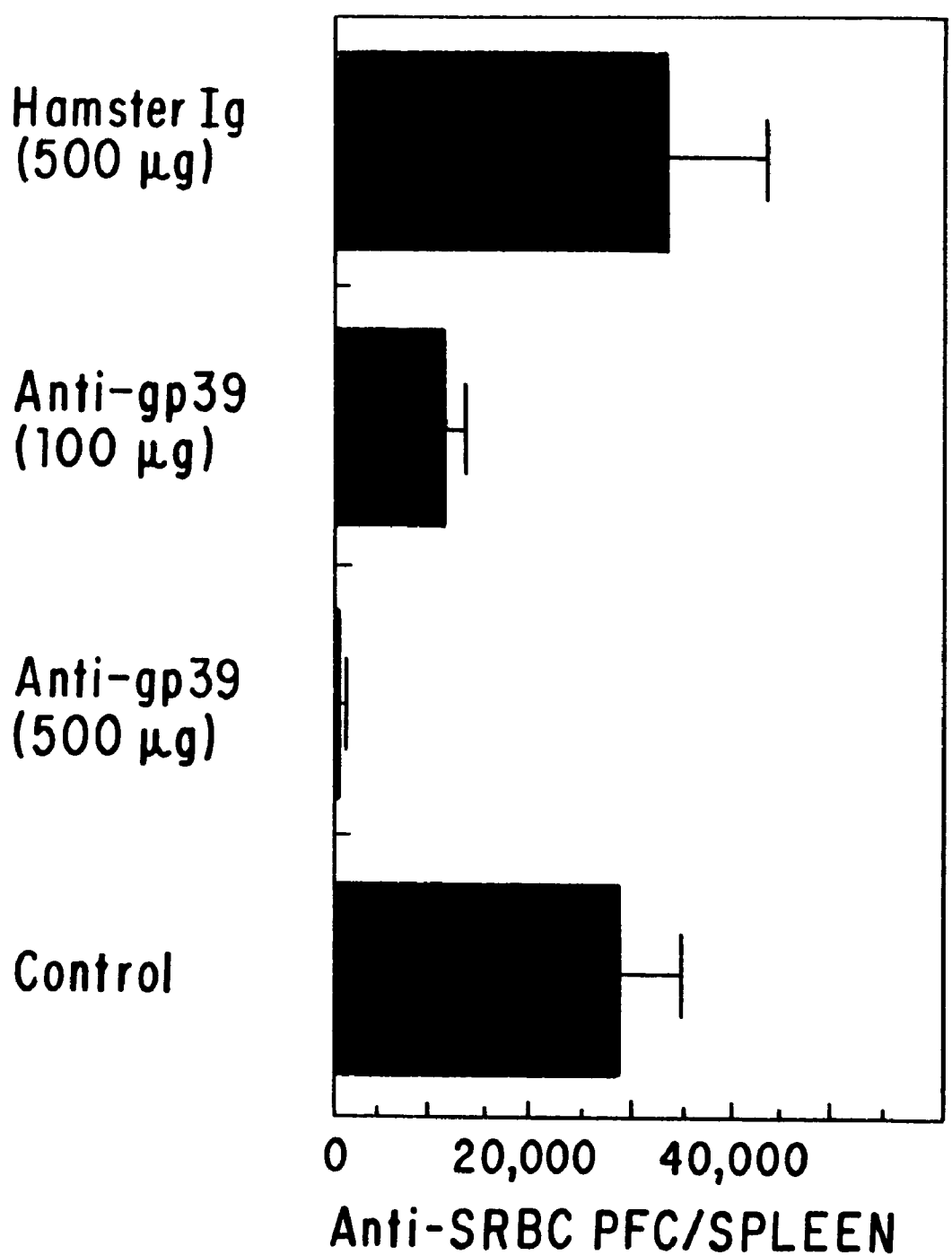

FIG. 15A. Anti-gp39 inhibits the generation of primary anti-SRBC PFC.

Mice (3/group) were administered 200 μl of 1.0% SRBC i.v. on d0. On d0, d2, and d4 mice were given either 100 or 500 μg of purified MR1 (hamster anti-murine gp39, purified from ascites by DEAE HPLC) or 500 μg of purified hamster Ig, i.p. The control group consists of mice receiving the immunization, but no antibody treatment. Spleens were removed from the mice on d5 and the number of direct (IgM) anti-SRBC PFC was determined by a modification of the Jerne plaque assay. The data is representative of 3 such experiments.

Figure 15B:
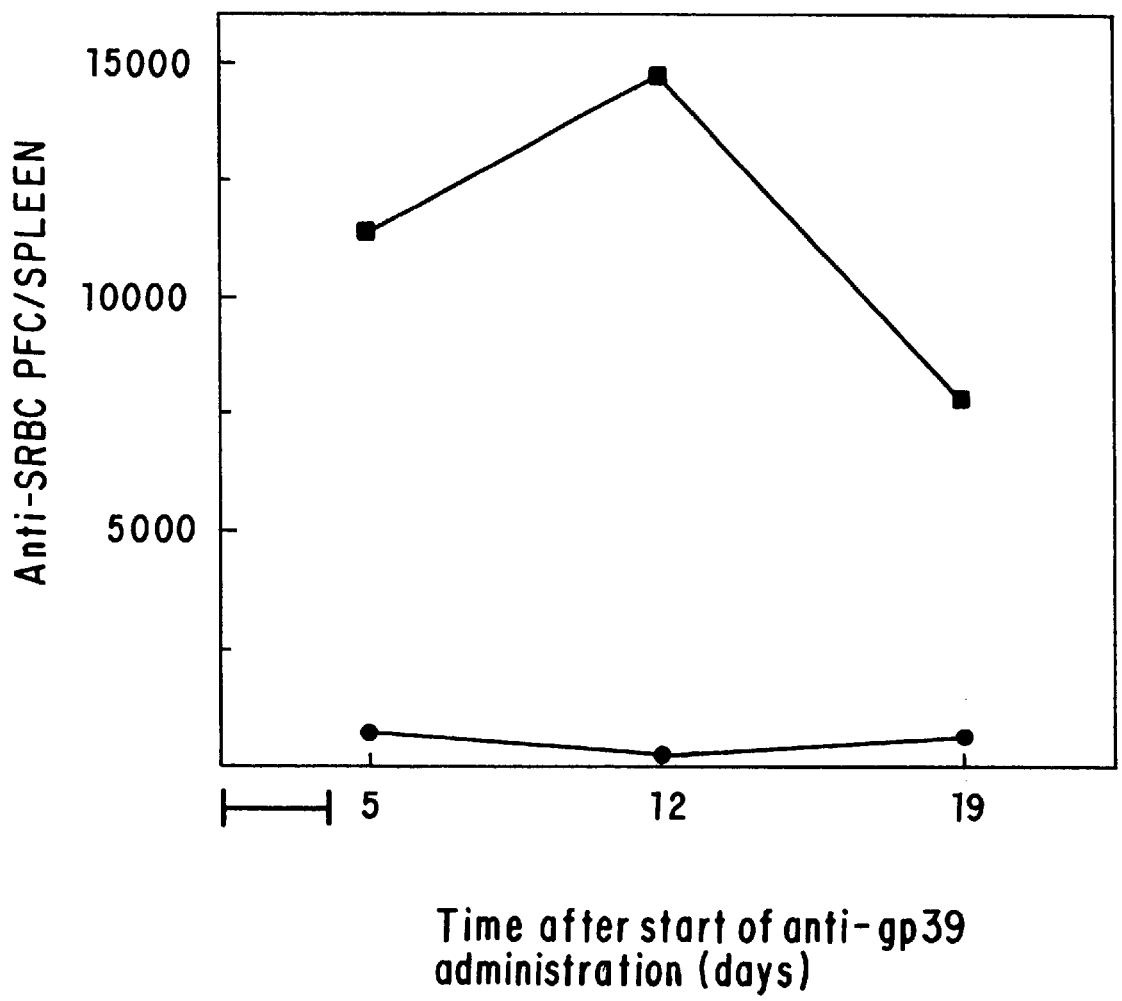

FIG. 15B. Prolonged immune suppression of primary anti-SRBC responses is induced by the administration of anti-gp39.

Mice (3/group) were immunized with SRBC (200 μl of 1.0% SRBC, i.v.) and on d0, d2 and d4, received 250 μg of anti-gp39 (●) or 250 μg hamster Ig (■), i.p. The time of antibody administration is indicated by the black bar. The anti-SRBC PFC response was determined on d5 post-immunization. Additional mice were challenged with antigen (0.2 ml of 1.0% SRBC i.v.) 7 d or 14 d after initial antigen immunization and anti-gp39 administration. The anti-SRBC PFC was then assayed 5 d later. The results are representative of three similar experiments.

Figure 16A:
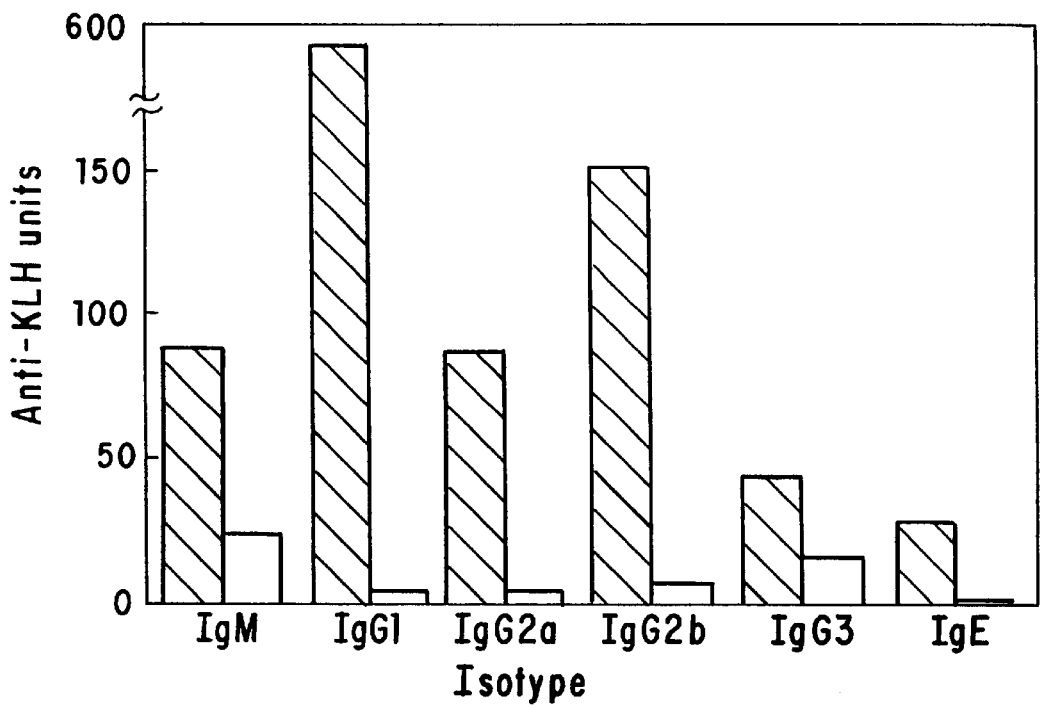
Figure 16B:
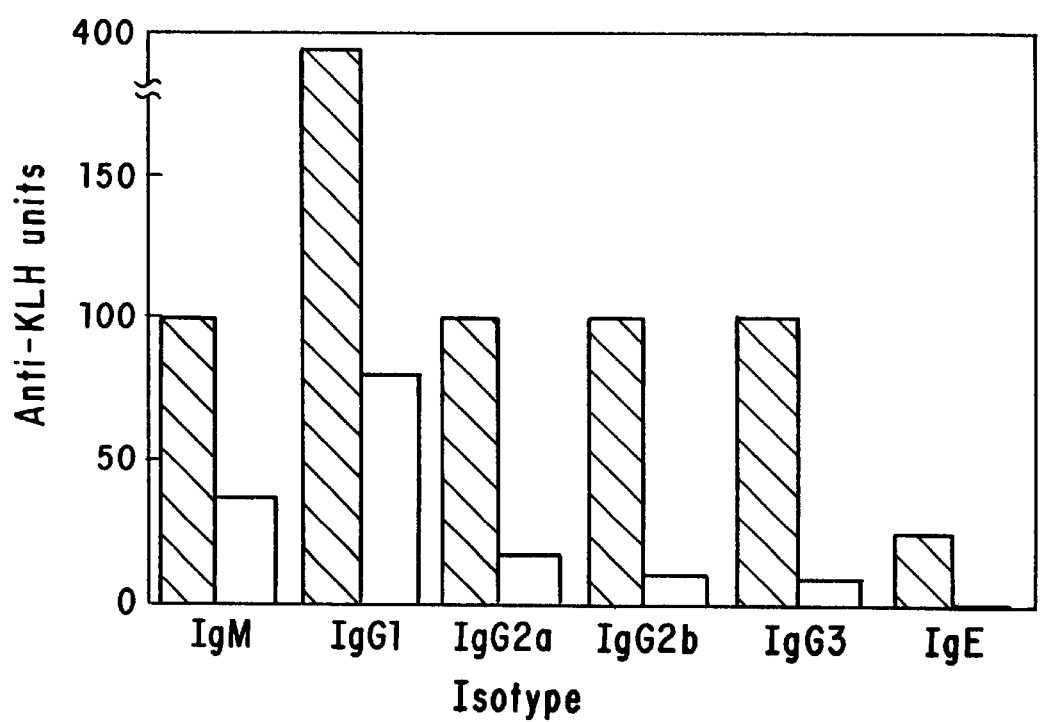

FIGS. 16A–16B. Anti-gp39 inhibits the generation of secondary anti-KLH antibody responses.

Mice (3/group) were immunized with KLH in CFA (50 μg/mouse i.v.) Three months after immunization, mice were given a soluble booster with 10 μg of KLH (i.v.). On d0, d2 and d4, immune mice received 250 μg of anti-gp39 i.p. (open bars) or 250 μg HIg (hashed bars). Serum from individual mice was collected on d7 (FIG. 16A) or d14 (FIG. 16B) post-antigenic challenge, pooled and levels of anti-KLH antibodies were determined using isotype specific ELISAs. Units represent arbitrary values based on the titration curve of a standard immune serum. All experimental groups were titered from 1:100 to 1:100,000 and the titer ascertained based on multiple point analysis. The levels of anti-KLH antibodies in unchallenged controls were below detection. The standard errors within each group were always less than 10%. These results are representative of three such experiments.

Figure 17A:
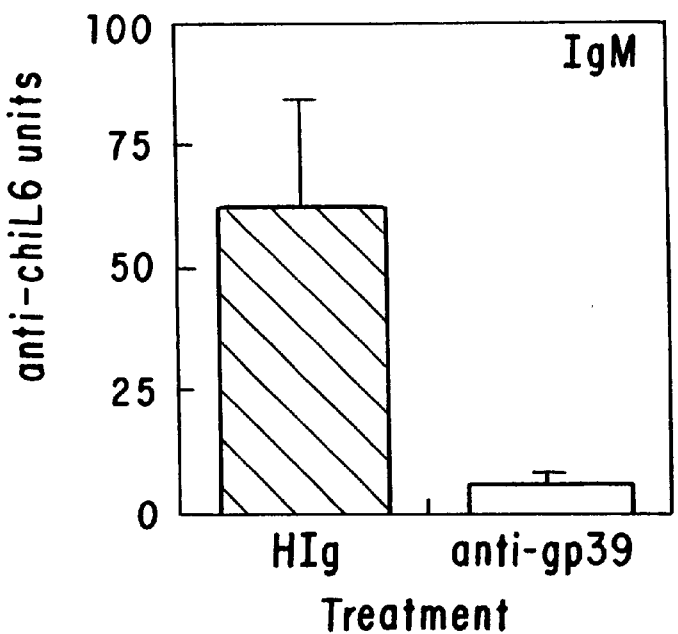
Figure 17B:
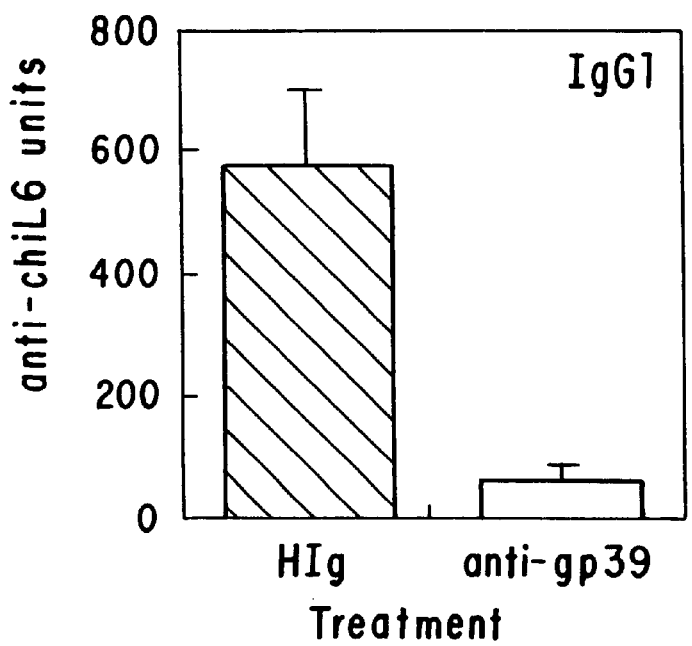

FIGS. 17A–17B. Anti-gp39 inhibits the generation of primary and secondary antibody responses to heterologous immunoglobulins.

Mice (3/group) were immunized i.p. with 100 μg Chi-L6 absorbed on alum. On d0, d2 and d4, immune mice received 250 μg of anti-gp39 i.p. (open bars) or 250 μg HIg (hashed bars). Serum from individual mice was collected on d7 after initial immunization (for IgM; FIG. 17A) or antigenic challenge (for $IgG_1$; FIG. 17B). The levels of anti-Chi-L6 IgM and $IgG_1$ antibodies were determined using antigen specific ELISAs. Units represent arbitrary values based on the titration curve or a standard immune serum. All experimental groups were titered from 1:100 to 1:100,000 and the titer ascertained based on multiple point analysis. The levels of anti-Chi-L6 antibodies in unchallenged controls were below detection. The results are representative of two separate experiments.

Figure 18A:
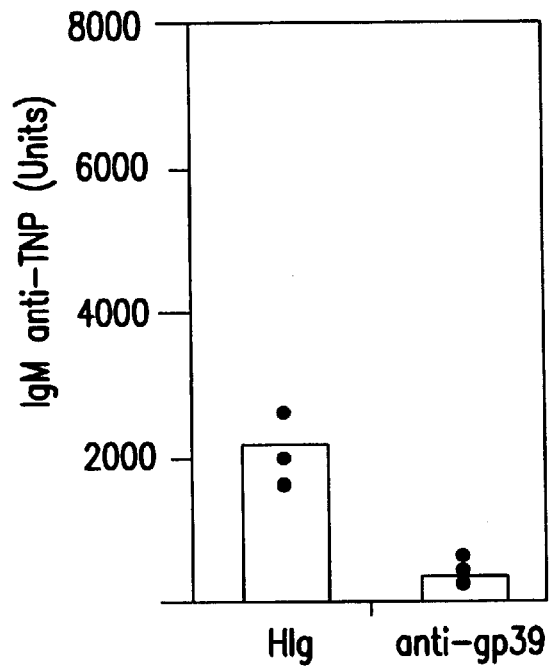
Figure 18B:
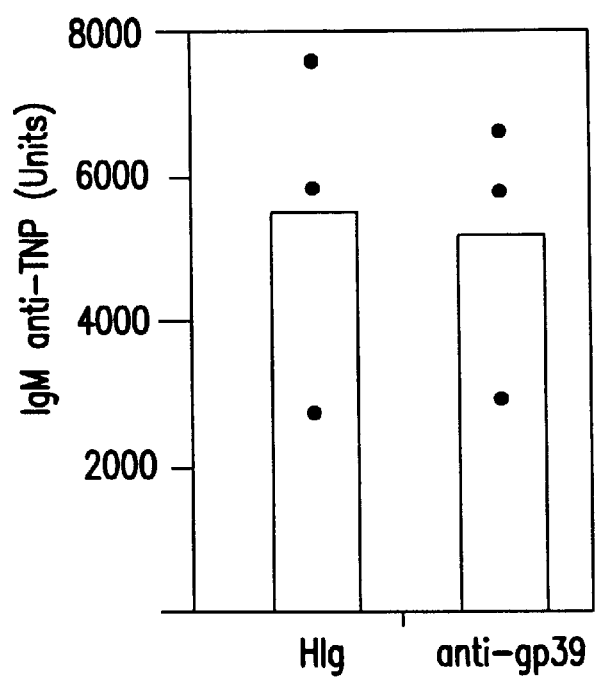

FIGS. 18A–18B. Anti-gp39 administration does not inhibit the generation of primary antibody responses to TNP-Ficoll.

FIG. 18A. Mice (3/group) were immunized with 200 82 1 1% TNP-SRBC i.v. On d0, d2, and d4 mice received 250 μg anti-gp39 or HIg. On d6 mice were bled and the IgM anti-TNP antibody titers determined by $TNP_{16}$-BSA ELISA. FIG. 18B. Mice (3/group) were immunized with 25 μg TNP-Ficoll i.v. On d0, d2, and d4 mice received 250 μg anti-gp39 or HIg. On d6 mice were bled and the IgM anti-TNP antibody titers determined by $TNP_{16}$-BSA ELISA. Units represent arbitrary values based on the titration curve or a standard immune serum. All experimental groups were titered from 1:100 to 1:100,000 and the titer ascertained based on multiple point analysis. The anti-TNP titer of nonimmune mice was 390 units. The results are representative of two separate experiments.

Figure 19:
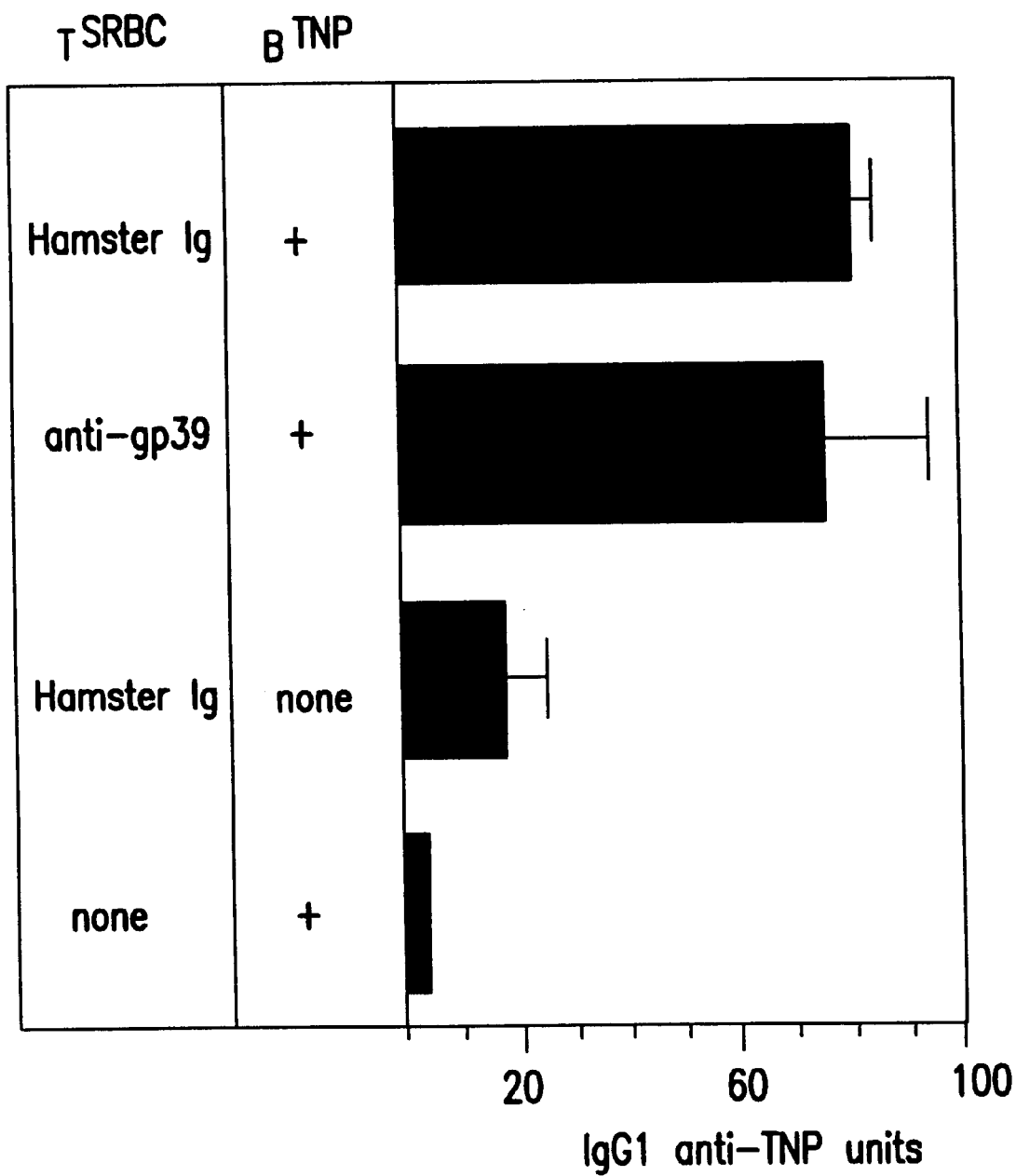

FIG. 19. Anti-gp 39 administration does not functionally delete SRBC-specific $T_h$.

Mice were immunized with SRBC (200 μl of 1.0% SRBC i.v.) and administered anti-gp39 or HIg (on d0, d2, d4; 250 μg/d). On d7, the spleens were removed and transferred (i.v., 50×10$^6$/mouse) into irradiated recipients (600 rads) with/without 50×10$^6$ spleen cells from TNP-KLH primed (KLH/CFA 50 μg, i.v.) mice as a source of immune B cells. At the time of transfer, mice were also immunized with TNP-SRBC (200 μl of 1.0% TNP/SRBC). Serum IgG, anti-TNP titers were ascertained on d6 post-transfer using a $TNP_2$-BSA ELISA. Units represent arbitrary values based on the titration curve of a standard immune serum. All experimental groups were titered from 1:100 to 1:100,000 and the titer ascertained based on multiple point analysis. The data are representative of two such experiments.

Figures 20A, 20B:
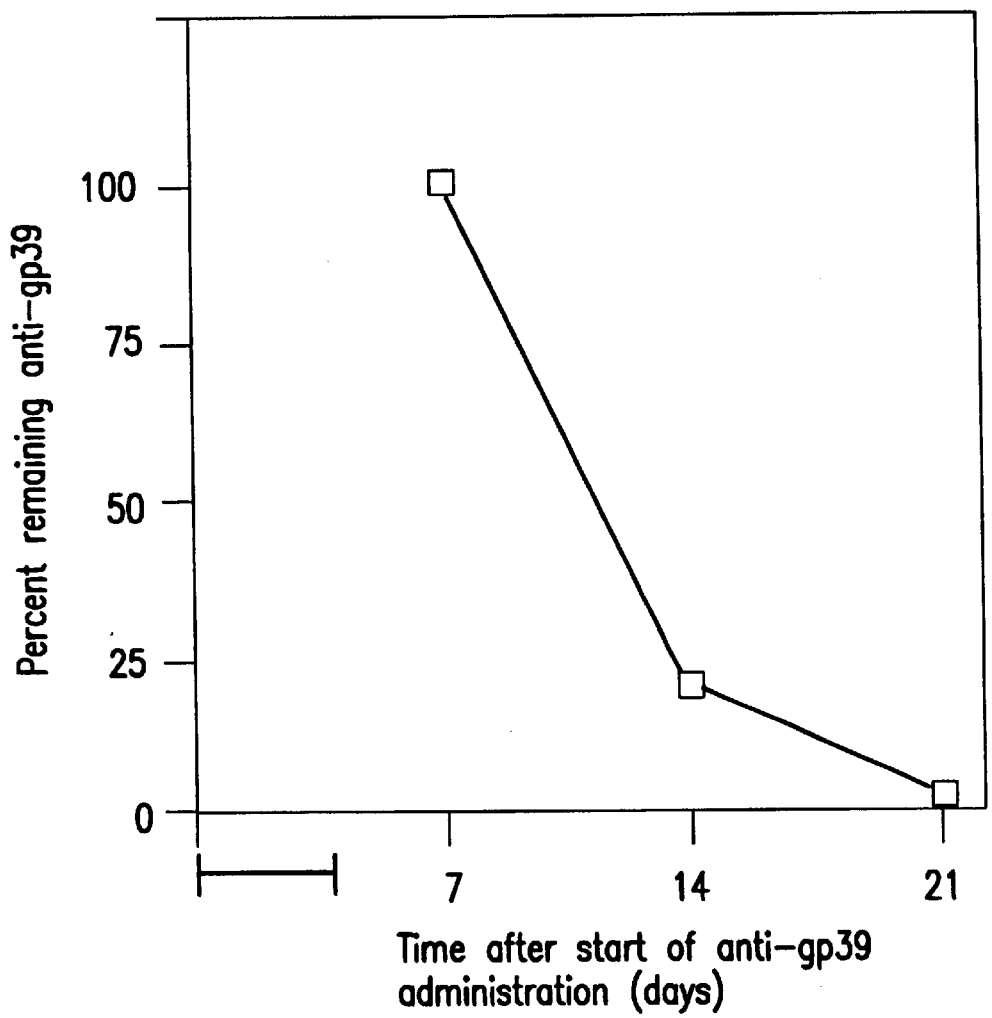

FIGS. 20A–20B. In vivo clearance of hamster anti-gp39.

Mice were administered 3×250 μg of anti-gp39 on d0, d2 and d4. On d7, d14 and d21 the amount of remaining anti-gp39 was determined as follows: FIG. 20A. Serum (1.5 μg) was electrophoresed under non-reducing conditions, transferred to nitrocellulose and blotted with HRPO-conjugated RG7 (mouse anti-hamster κ chain), followed by chemiluminescent detection. Areas of the blot corresponding to 150–165 kDa were scanned and digitized. FIG. 20B. Titrations of serum were used to stain activated $T_h1$ to determine the amount of biologically active anti-gp39 present in the serum. Activated $T_h1$ were stained with titrations of serum followed by FITC-anti-hamster κ chain (RG7). The percent anti-gp39 remaining in serum was deduced based on a standard curve of Mean Fluorescence Intensity (MFI) vs serum concentration, using d7 as 100%. The time of antibody administration is indicated by the black bar. The results are representative of two such experiments.

Figure 21A:
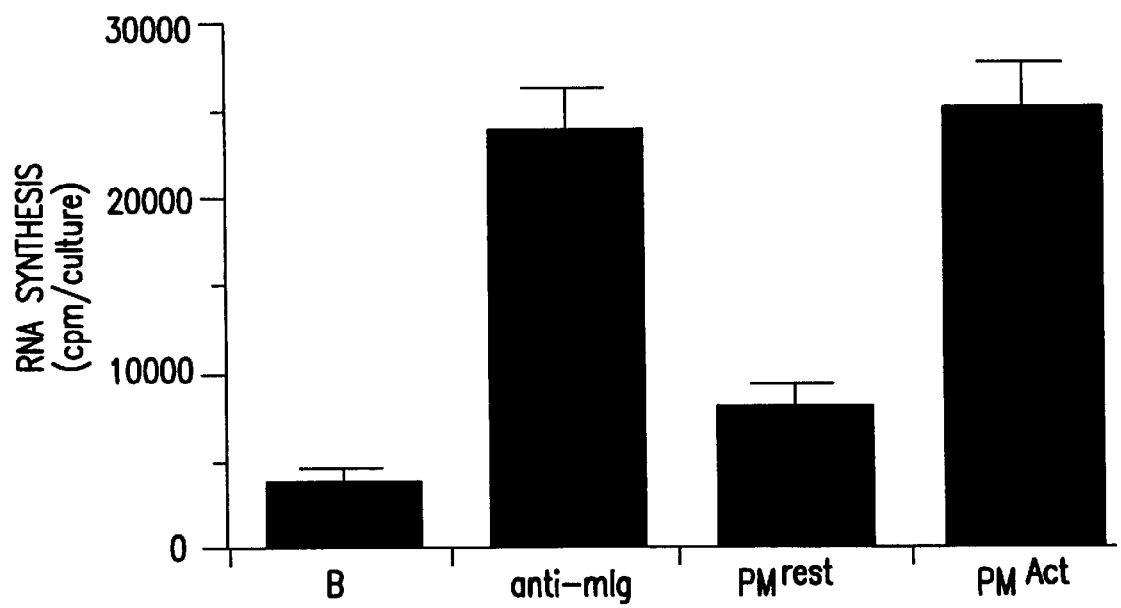
Figure 21B:
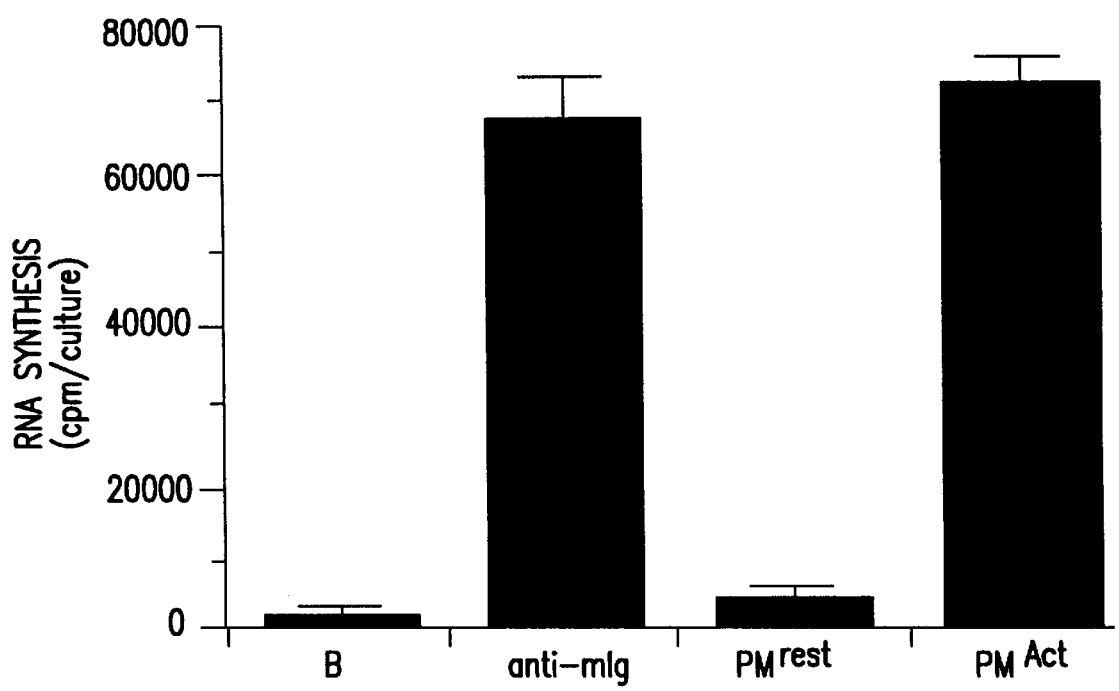

FIGS. 21A–21B. $PM^{Act}$ drive B cell cycle entry.

Murine resting B cells (3×10$^4$/well) were cultured alone or with $PM^{rest}$ (2 μg/well), $PM^{Act}$ (2 μg/well), or anti-mIg (GαM IgG F(ab')$_2$; 50 μg/ml) in a final volume of 50 μl for (FIG. 21A) 8 hours or (FIG. 21B) 24 hours at 37° C. Wells were pulsed with 5 μCi/well of $^3$H-Udr for 2 hours, harvested and processed for liquid scintillation spectroscopy. Results are reported as cpm/culture, with standard error, and are an average of 5 such experiments.

Figure 22:
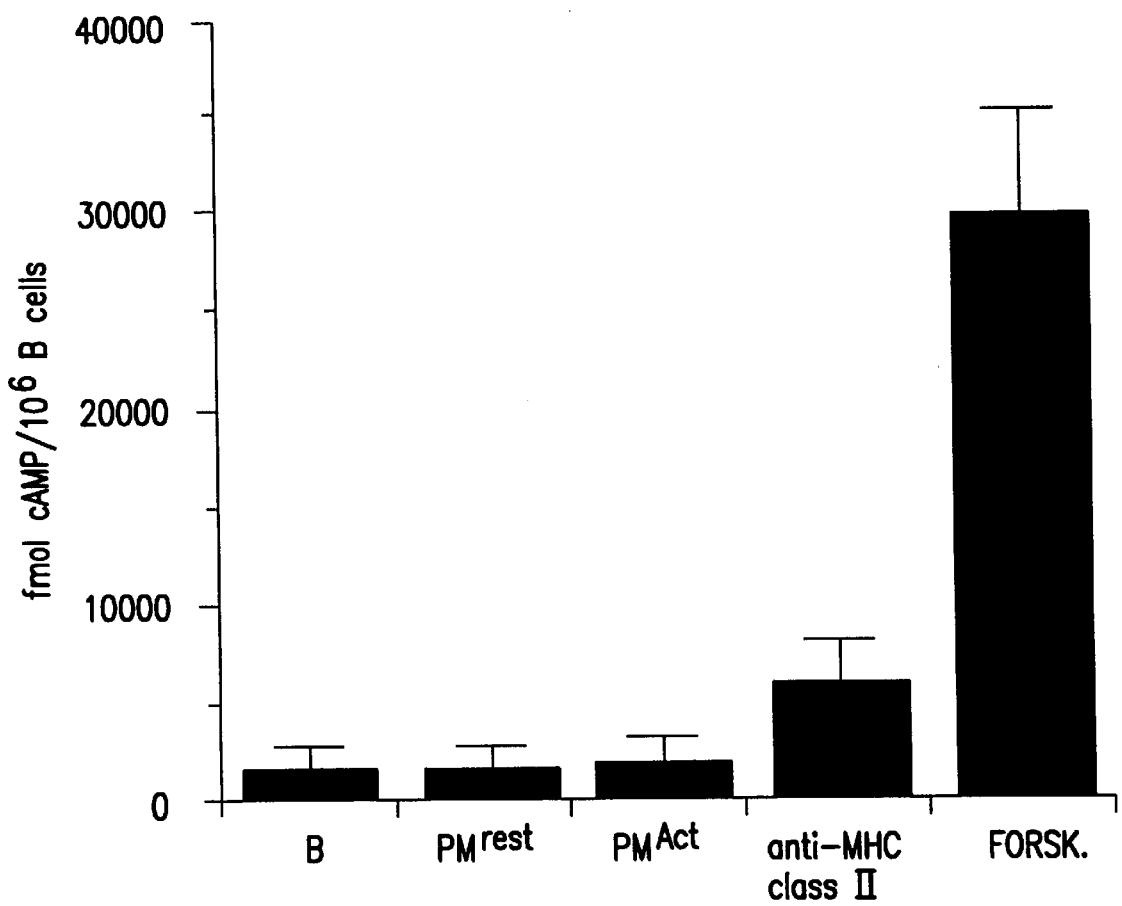

FIG. 22. Measurement of $cAMP_i$ during $T_h$ dependent B cell activation.

Murine resting B cells (10$^6$ cells/sample) were cultured alone (denoted B) or with $PM^{rest}$ (10 μg/sample), $PM^{Act}$ (10 μg/sample), anti-MHC class II (M5; 50 μg/ml) or forskolin (50 μM) in a final volume of 100 μl for 15 minutes at 37° C. At the appropriate time, cells were analyzed for cAMP content by RIA as described in Methods and Materials. Results are reported as fmol cAMP/10$^6$ B cells, with standard error, and are an average of 3 such experiments.

Figure 23:
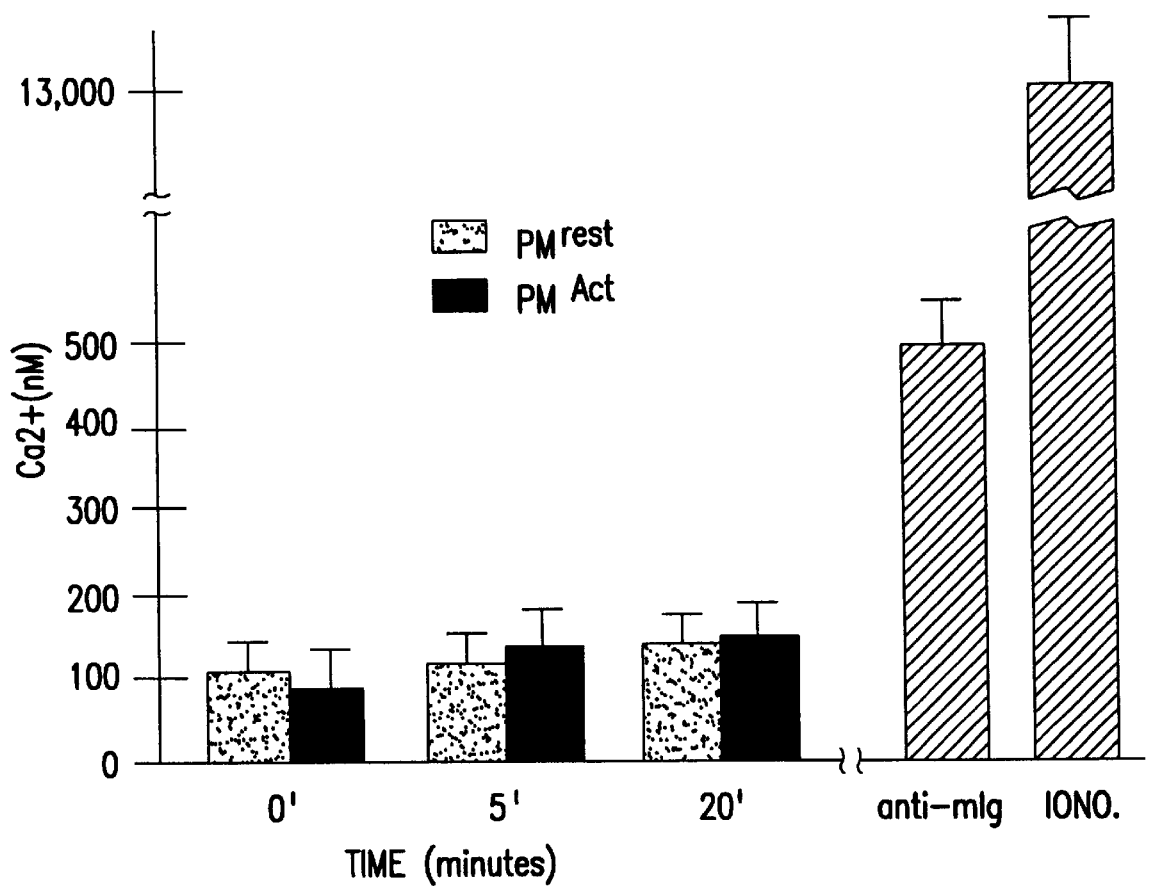

FIG. 23. $PM^{Act}$ do not stimulate an increase in B cell $Ca^{2+}_i$.

Murine resting B cells (10$^7$/ml) were loaded with Indo-1 (5 μM) for 30 minutes at 37° C. Cells were aliquoted at 10$^6$/sample and maintained at 37° C. until FACS analysis. During analysis, $PM^{rest}$ (10 μg/sample), $PM^{Act}$ (10 μg/sample), anti-mIg (50 μg/ml) and ionomycin (5 μM) were added in a final volume of 100 μl and Indo-1 fluorescence was monitored over time. Results are reported as nM calcium, with standard error, and are an average of 3 such experiments.

FIG. 24. $PM^{Act}$ do not induce the phosphorylation of MARCKS in B cells.

Murine resting B cells (10$^7$ cells/ml) were labeled with $^{32}$P-orthophosphate (0.5 μCi/ml) for 1 hour at 37° C. Cells were aliquoted (5×10$^5$/sample) and then cultured alone or with $PM^{Rest}$ (10 μg/sample, $PM^{Act}$ (10 μg/sample or PMA (50 μg/ml) in a final volume of 100 μl for various time points at 37° C. Cells were lysed and immunoprecipitated with an anti-MARCKS antiserum as described in Methods and Materials. Samples were analyzed through electrophoresis and autoradiography. The photograph shown is a representative example of 10 such experiments with the autoradiogram exposed for 18 hours at −80° C.

Figure 25:
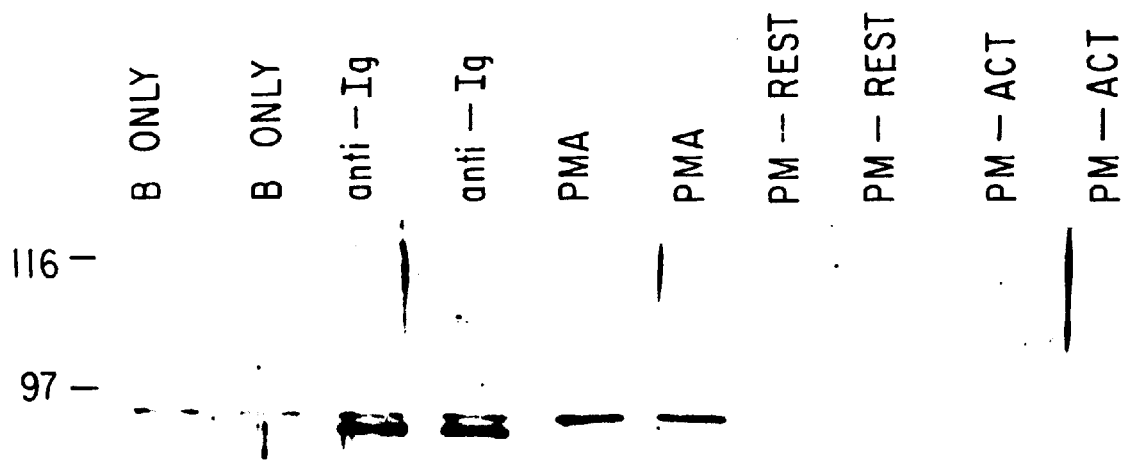

FIG. 25. $PM^{Act}$ do not induce PKC translocation in B cells.

Murine resting B cells (5×10$^5$/sample) were cultured with $PM^{Rest}$ (10 μg/sample, $PM^{Act}$ (10 μg/sample in a final volume of 100 μl for 30 minutes at 37° C. In addition, cells were cultured alone or with anti-mIg (GαM IgG F(ab')$_2$; 50 μg/ml) or PMA (100 ng/ml) in a final volume of 100 μl for 5 minutes at 37° C. Cells were then permeabilized, electrophoresed, and probed with an anti-PKC polyclonal antibody. The photograph shown, including membrane fractions only, is a representative example of 8 such experiments and was exposed for 10 minutes.

Figures 26A, 26B:
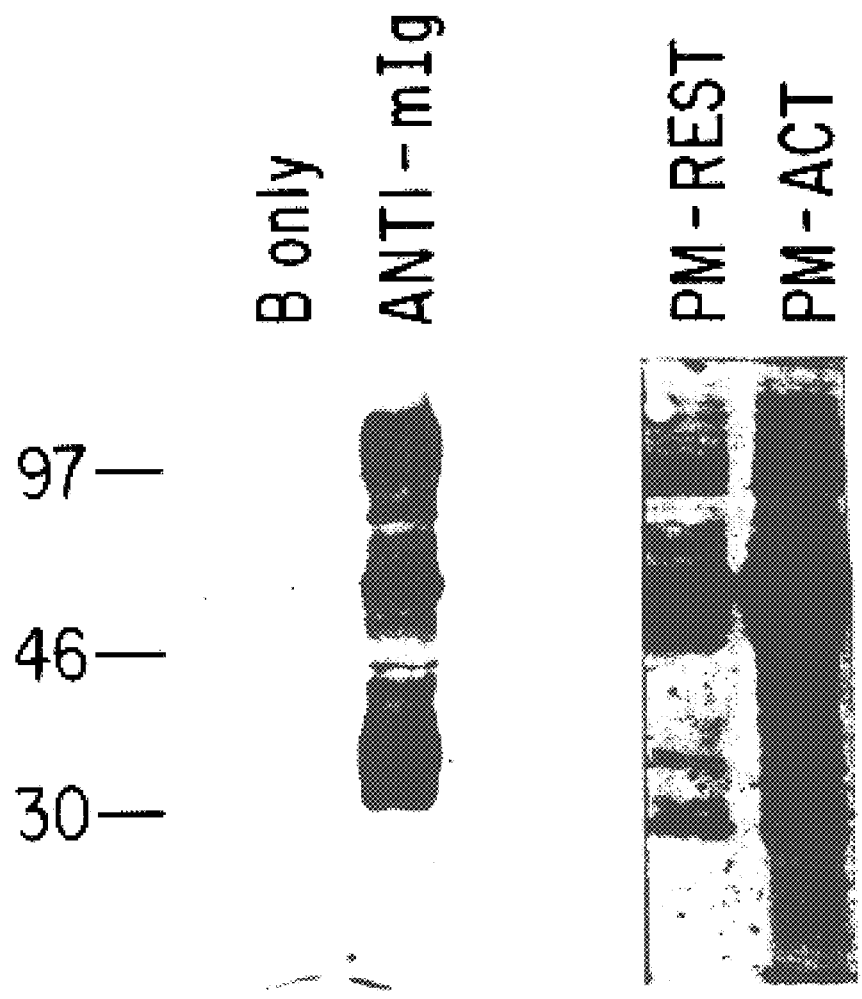

FIGS. 26A–26B. Induction of tyrosine phosphorylation during $T_h$-dependent B cell activation.

Murine resting B cells (5×10$^5$/sample) were prewarmed for 30 minutes at 37° C. FIG. 26A. Cells were then cultured in the presence and absence of anti-mIg (GαM IgG F(ab')$_2$; 50 μg/ml) in a final volume of 100 μl for 15 minutes at 37° C. Cells were lysed, lysates were electrophoresed, and the blot was probed with an anti-phosphotyrosine monoclonal antibody. The photograph shown is a representative example of 10 such experiments and was exposed for 30 seconds. FIG. 26B. Cells were cultured with $PM^{rest}$ (10 μg/sample) or $PM^{Act}$ (10 μg/sample) in a final volume of 100 μl for 1 hour at 37° C. and prepared, as described above. The photograph shown is a representative example of 10 such experiments and was exposed for 10 minutes.

Figure 27A:
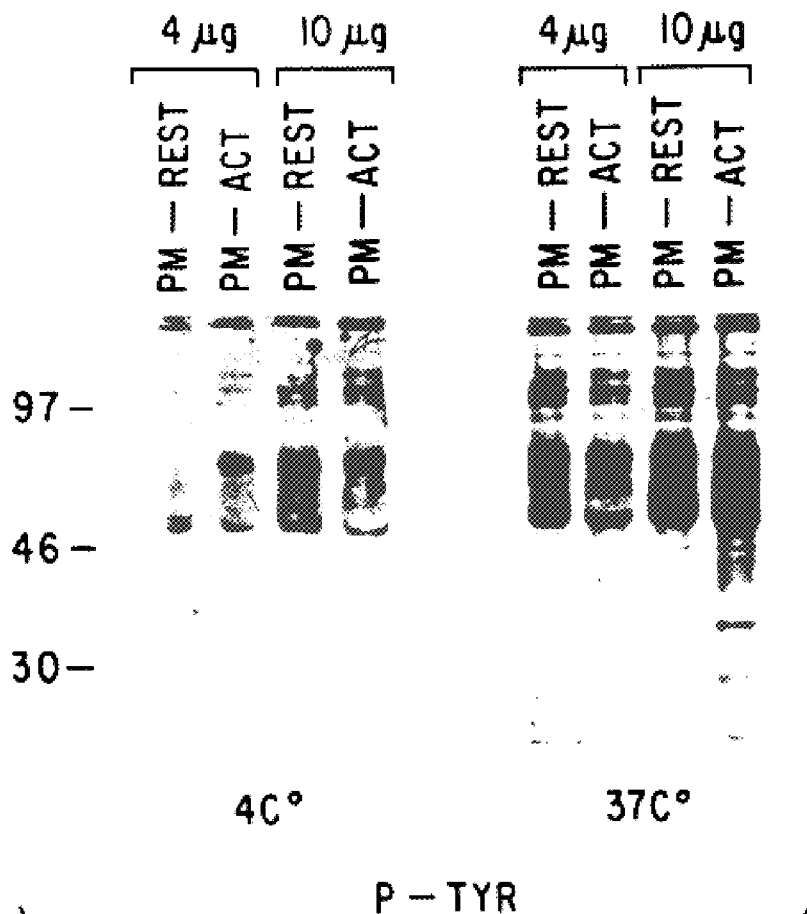
Figure 27B:
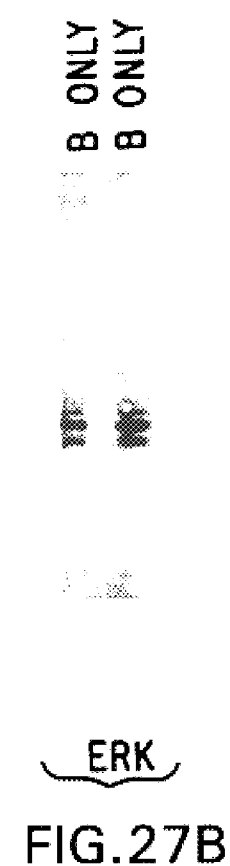

FIGS. 27A–27B. Tyrosine phosphorylation is an active event.

Murine resting B cells (5×10$^5$/sample) were preincubated for 30 minutes at 4° C. (Left panel) or 37° C. (Middle panel). Cells were then cultured with P$^{rest}$ (4 or 10 μg/sample) or PM$^{Act}$ (4 or 10 μg/sample) in a final volume of 100 μl for 1 hour at 4° C. or 37° C. Cells were lysed, electrophoresed, and probed with an anti-phosphotyrosine monoclonal antibody (FIG. 27A). The photograph shown is a representative example of 12 such experiments and was exposed for 10 minutes. Murine resting B cells were lysed, electrophoresed and probed with an anti-ERK polyclonal antiserum as described in Methods and Materials (Right panel FIG. 27B). The photograph shown is a representative example of 12 such experiments and was exposed for 5 minutes.

Figure 28:
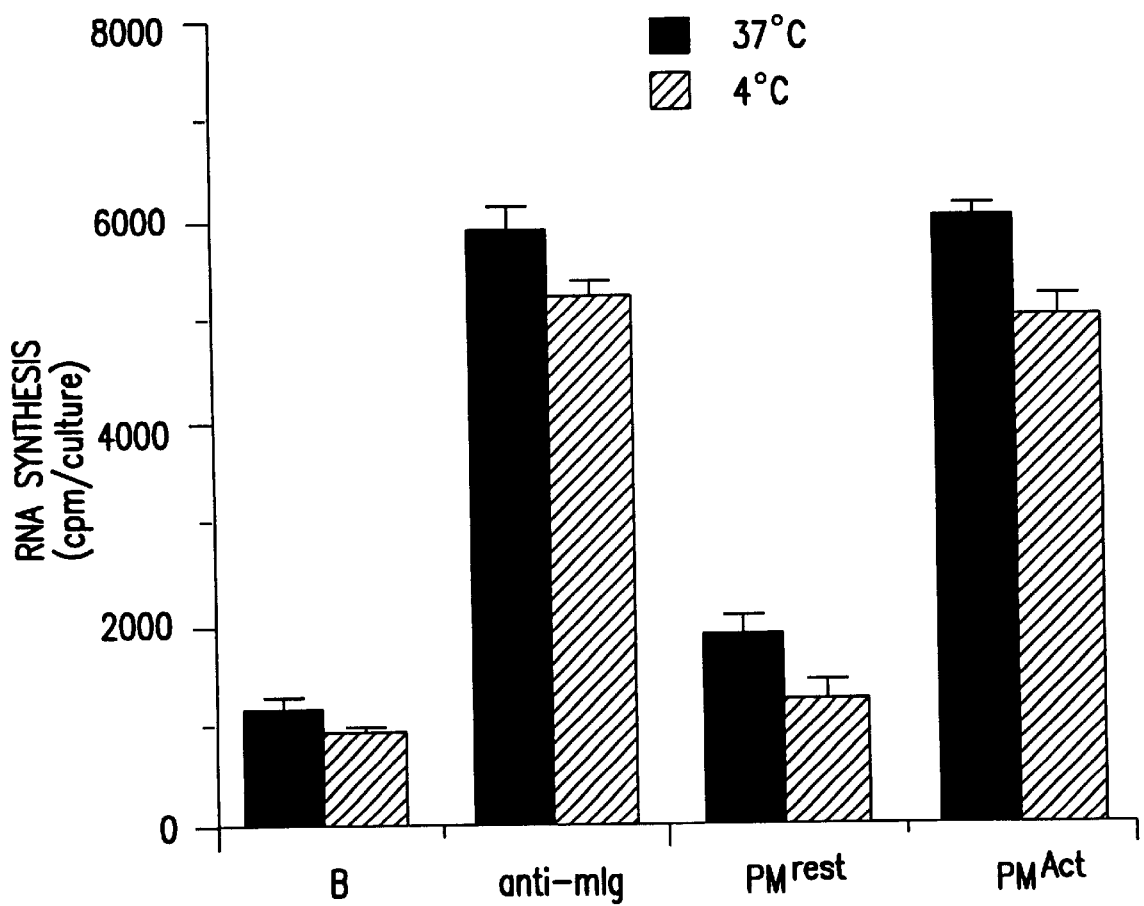

FIG. 28. PM$^{Act}$ binding is not inhibited at 4° C. as measured by enhanced B cell cycle entry.

Murine resting B cells (5×10$^5$/sample) were preincubated for 30 minutes at 4° C. or 37° C. Cells were then cultured with PM$^{rest}$ (10 μg/sample) or PM$^{Act}$ (10 μg/sample) in a final volume of 50 μl for 1 hour at 4° C. or 37° C. In addition, B cells were cultured alone or with anti-mIg (GαM IgG F(ab')$_2$; 50 μg/ml) in a final volume of 50 μl for 15 minutes at 4° C. or 37° C. B Cells were then washed three times and RNA synthesis was measured. These results are reported as cpm/culture, with standard error, and are an average of 3 such experiments.

Figure 29:
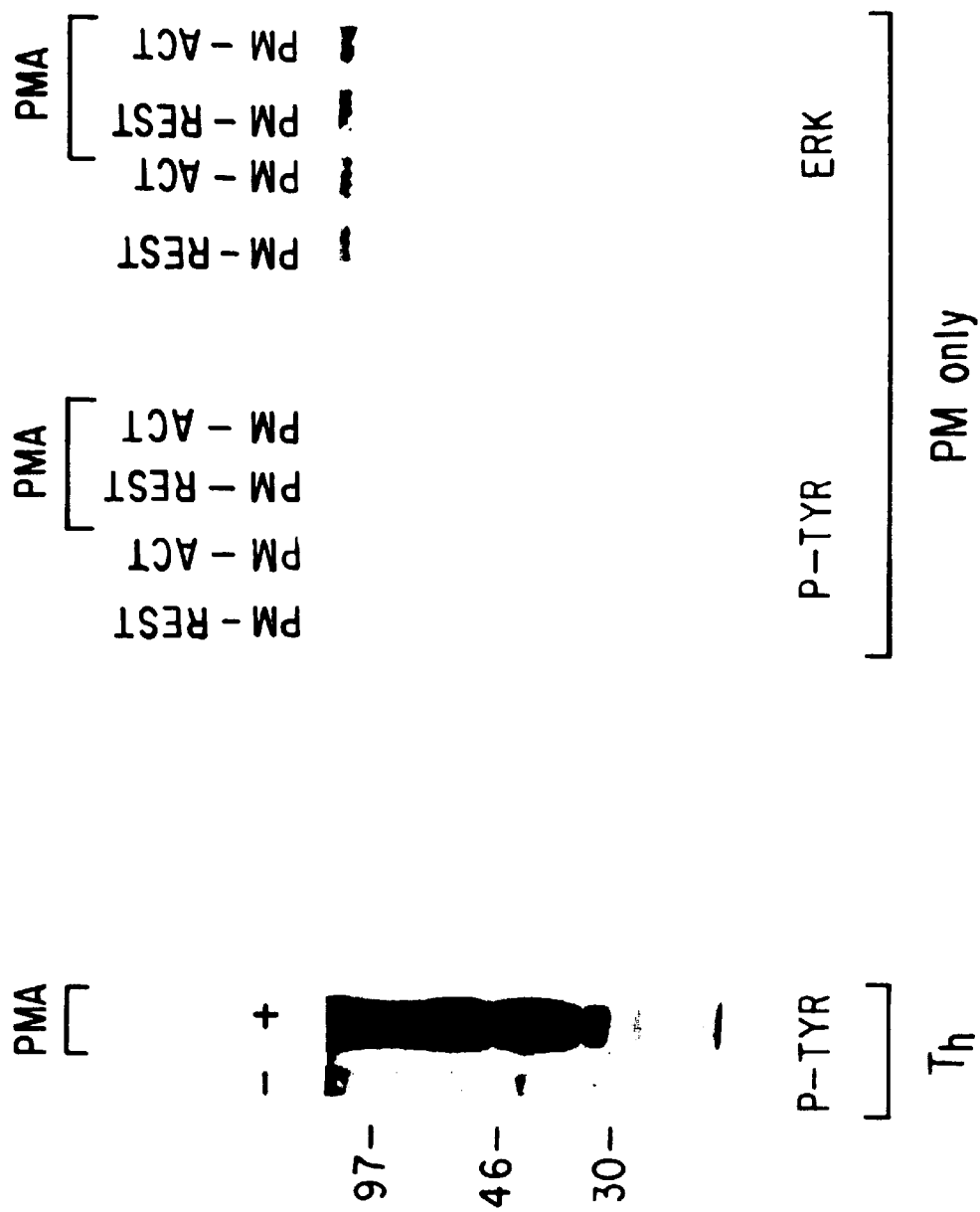

FIGS. 29A–29B. Lack of detectable tyrosine phosphorylation in PM$^{Act}$ stimulated with PMA.

PM$^{rest}$ (10 μg/sample), PM$^{Act}$ (10 μg/sample) (FIG. 29B) or T$_h$ (5×10$^5$/sample) (FIG. 29A) were incubated in the presence and absence of PMA (100 ng/ml) in a final volume of 25 μl for 5 minutes at 37° C. Samples were then prepared for electrophoresis and probed with an anti-phosphotyrosine monoclonal antibody. The photograph shown is a representative example of 3 such experiments and was exposed for 45 minutes. This PMA/PM$^{Act}$ phosphotyrosine blot (FIG. 29B) was stripped and reprobed with an anti-ERK polyclonal antiserum as described above. Molecular weight standards are the same as in FIG. 29A; ERK I has a molecular weight of 43 kd. The photograph shown is a representative example of 3 such experiments and was exposed for 10 minutes.

Figure 30:
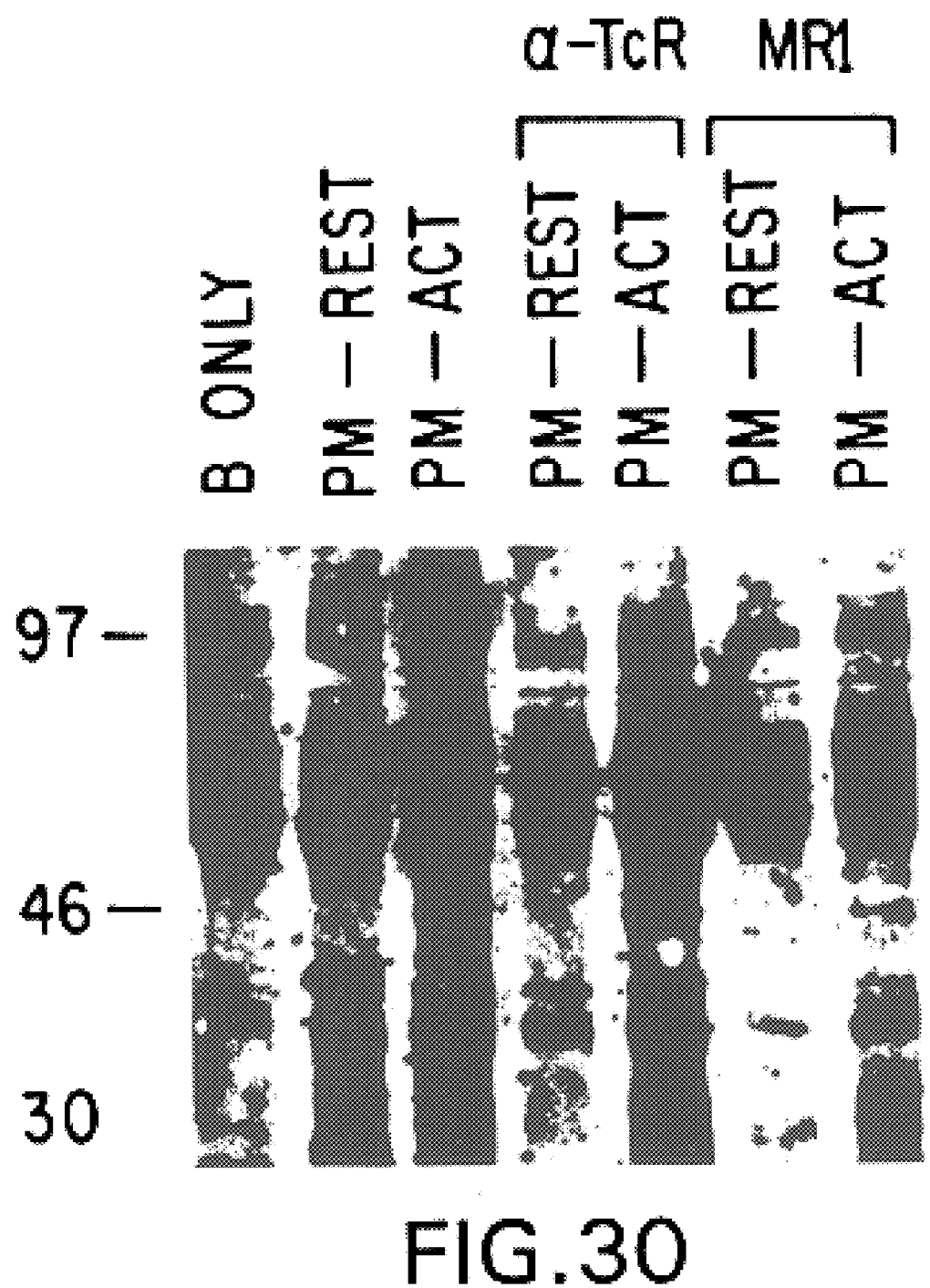

FIG. 30. Anti-gp39 inhibits PM$^{Act}$ induced tyrosine phosphorylation in B cells.

Murine resting B cells (5×10$^5$/sample) were prewarmed for 30 minutes at 37° C. Cells were then cultured alone or with PM$^{rest}$ (10 μg/sample) or PM$^{Act}$ (10 μg/sample) which had been preincubated with anti-gp39, MR1, (50 μg/ml) or anti-TcR (50 μg/ml) in a final volume of 50 μl for 30 minutes at 4° C. Cultures were incubated in a final volume of 100 μl for 1 hour at 37° C. Cells were prepared for electrophoresis and probed with an anti-phosphotyrosine monoclonal antibody. The photograph shown is a representative example of 3 such experiments and was exposed for 10 minutes.

Figures 31A, 31B:
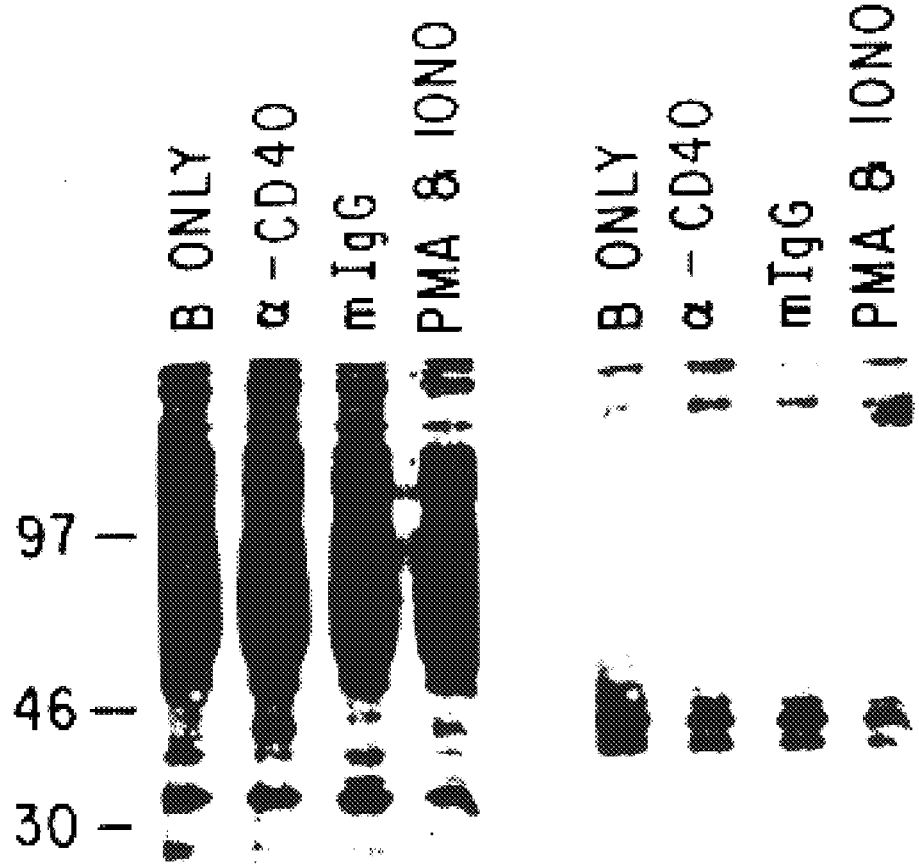

FIGS. 31A–31B. Anti-CD40 induces a phosphotyrosine profile in human B cells.

Human B cells (5×10$^5$/sample) were prewarmed for 30 minutes at 37° C. Cells were then cultured with anti-CD40 (1 μg/ml), mIgG (1 μg/ml or PMA (100 ng/ml) plus ionomycin (75 ng/ml) in a final volume of 100 μl for 5 minutes at 37° C. Cells were lysed, electrophoresed and probed with an anti-photyrosine monoclonal antibody (FIG. 31A). The photograph shown is a representative example of 3 such experiments and was exposed for 30 minutes. This anti-CD40/human B cell phosphotyrosine blot was stripped and reprobed with an anti-ERK polyclonal antiserum as described above (FIG. 31B). The photograph shown is a representative example of 3 such experiments and was exposed for 10 minutes.

Figure 32:
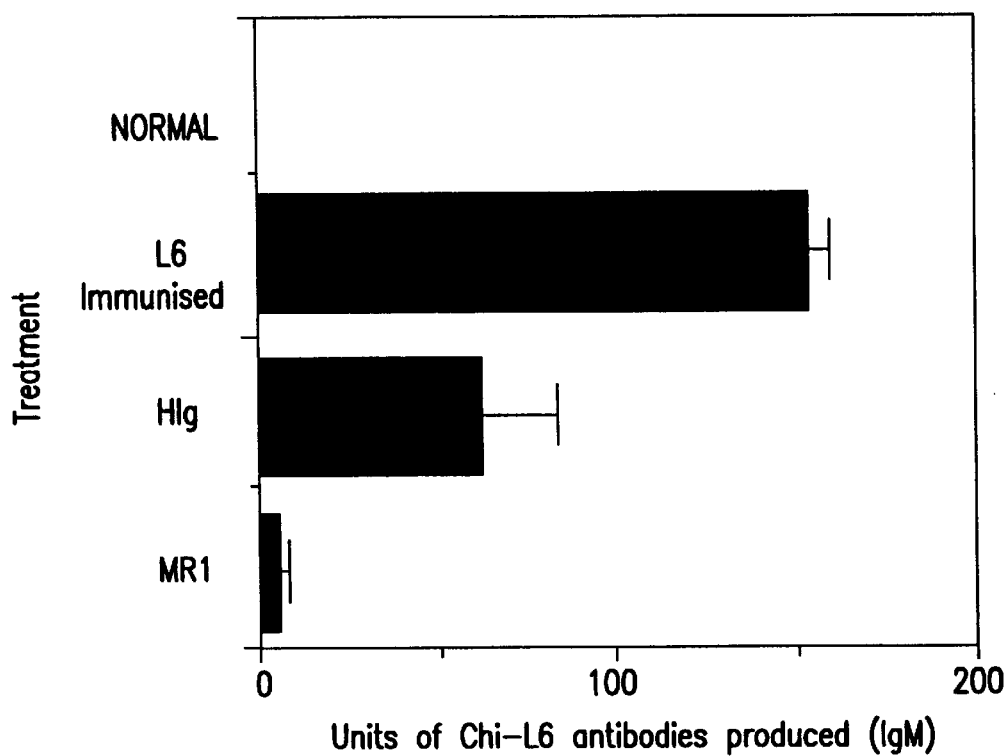

FIG. 32. Effect of MR1 treatment on the primary immune response to Chi-L6.

Figure 33:
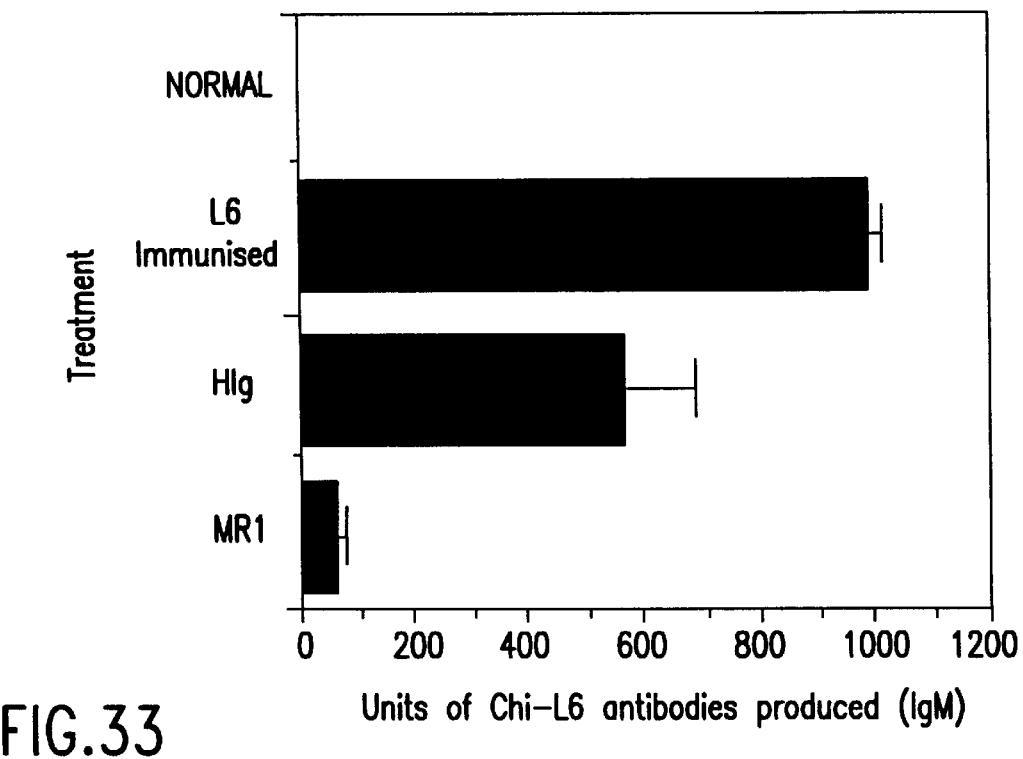

FIG. 33. Effect of MR1 treatment on the secondary immune response to Chi-L6.

Figure 34A:
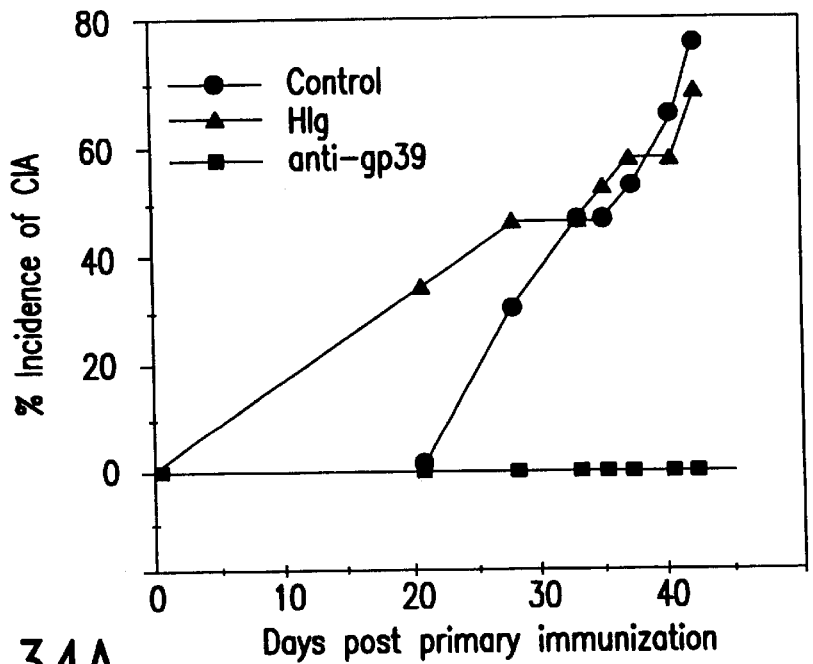
Figure 34B:
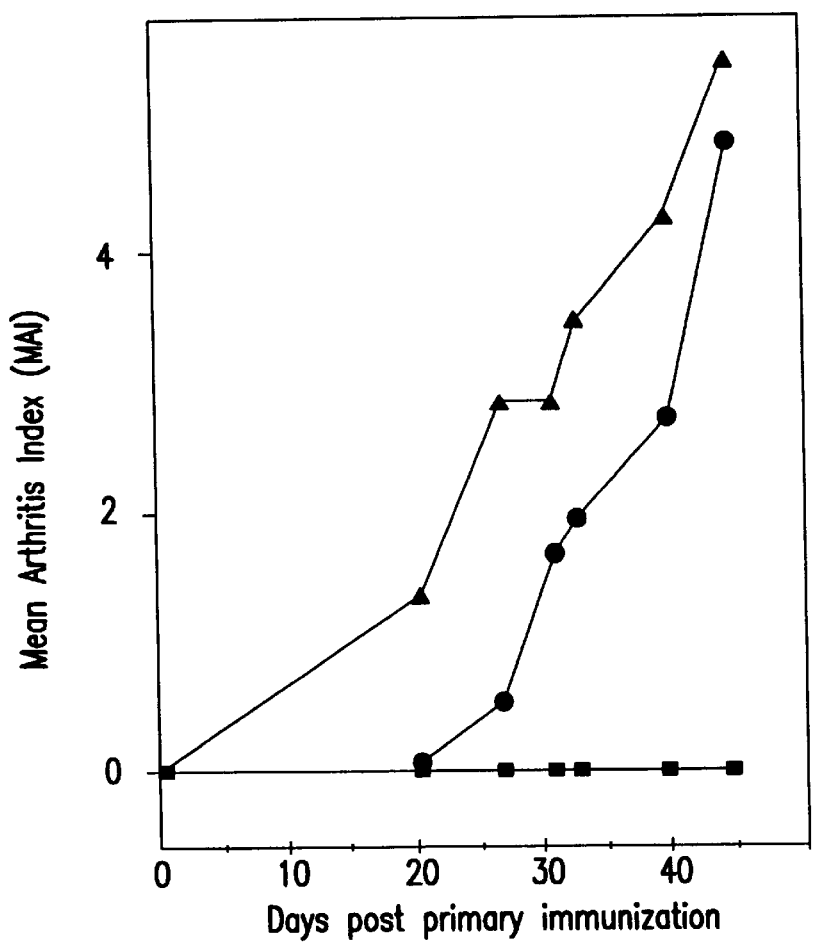

FIGS. 34A–34B. Anti-gp39 treatment prevented the occurrence of CIA.

FIG. 34A Male DBA/1J mice 6 weeks of age were anesthetized and immunized with chick CII emulsified in a complete adjuvant prepared by combining Freund's incomplete adjuvant (Difco) and 2 mg/ml *Mycobacterium tuberculosis* (Ministry of Agriculture and Fisheries, Weybridge, Surrey, England). CII (200 μg) was injected in a single intradermal site at the base of the tail and then challenged with soluble CII (100 μg) 21 days later. The mAb to gp39 antibody (MR1) is a hamster mAb to mouse gp39. Antibody treatment (DEAE purified MR1 and HIg) was initiated 7 days after the primary immunization and maintained throughout the study (250 μg per mouse every 4 days). Mice (8 mice per group) were then routinely monitored for the development of clinical symptoms of CIA by inspection of distal joint inflammation. FIG. 34B. Anti-gp39-treatment inhibits the severity of CIA. Arthritic index (0 to 4) was determined by monitoring both hind and forepaws and scored by a subjective scale with 4 being intense swelling and erythema. Mean Arthritis Index (MAI) was then determined by summation of the total score of each joint in each group of mice and dividing by the total animals in each group: control mice (●) HIg-treated mice (▲) and anti-gp39-treated mice (■). These results are representative of two such experiments.

Figure 35:
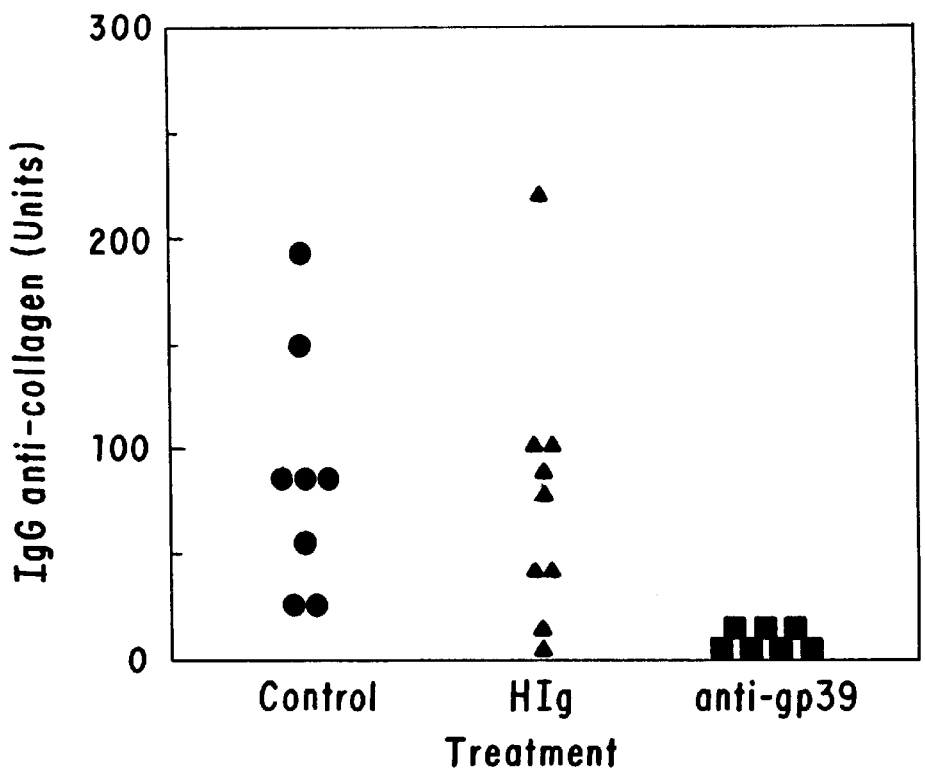

FIG. 35. Anti-gp39 inhibits the secondary humoral immune response to CII.

Serum samples were analyzed for the presence of mouse CII-reactive IgG. Each well of a polyvinyl microtiter plate was coated overnight at 4° C. with 100 μl of 5 μg/ml of chick CII and then blocked at incubation with PBS containing 1% FCS and 0.02% azide. After washing, a 100 μl aliquot of each serum, diluted in PBS, was added and the plates were incubated for 2 hours at 37° C., washed again, and incubated for a further 2 hours with 100 μl of alkaline phosphatase conjugated goat anti-mouse IgG$_1$ (Southern Biotechnology Inc., Birmingham Ala.). Plates were thoroughly washed and phosphatase substrate (Sigma Diagnostics, St. Louis, Mo.) added resulting in the appropriate color change. Readings were determined by an ELISA reader (Dynatech Laboratories, Inc.) at an absorbance of 410 nm. IgG, anti-CII was quantitated based on a standard curve generated using a hyperimmune antisera to CII. Values are represented in arbitrary units. Titers of antibody were determined for control mice (●) HIg-treated mice (▲) and anti-gp39-treated mice (■).

Figure 36:
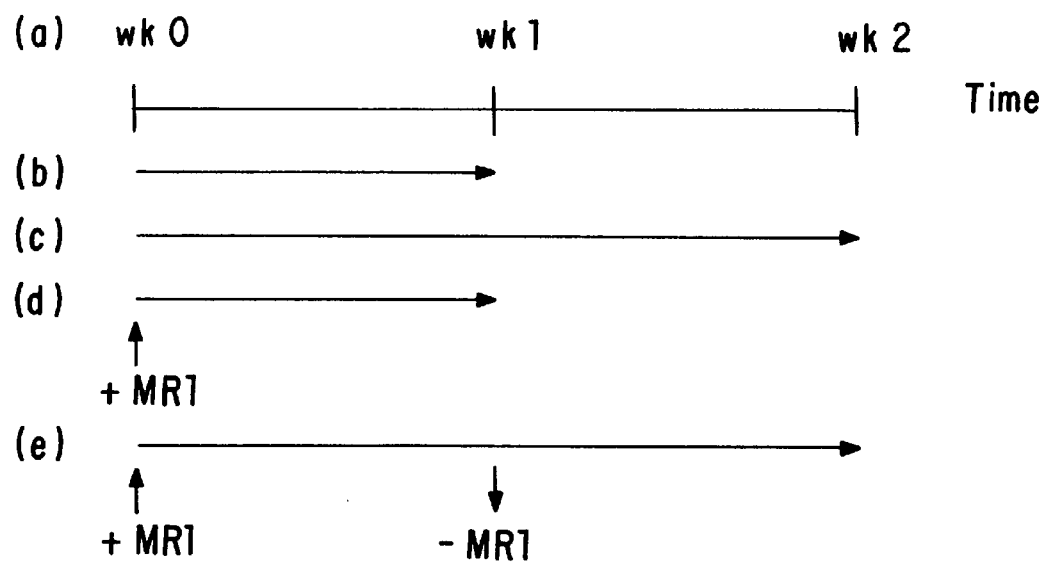

FIG. 36. Time course indicating the induction of GVHD and the administration of anti-gp39.

(a) normal F1 recipients (B6D2F1), (b) mice induced with GVHD for 1 wk, (c) mice induced with GVHD for 2 wks, (d) mice induced with GVHD for 1 wk while undergoing MR1 treatment and (e) mice induced with 2 wk GVHD but only treated with the antibody for the first week of the disease.

Figure 37:
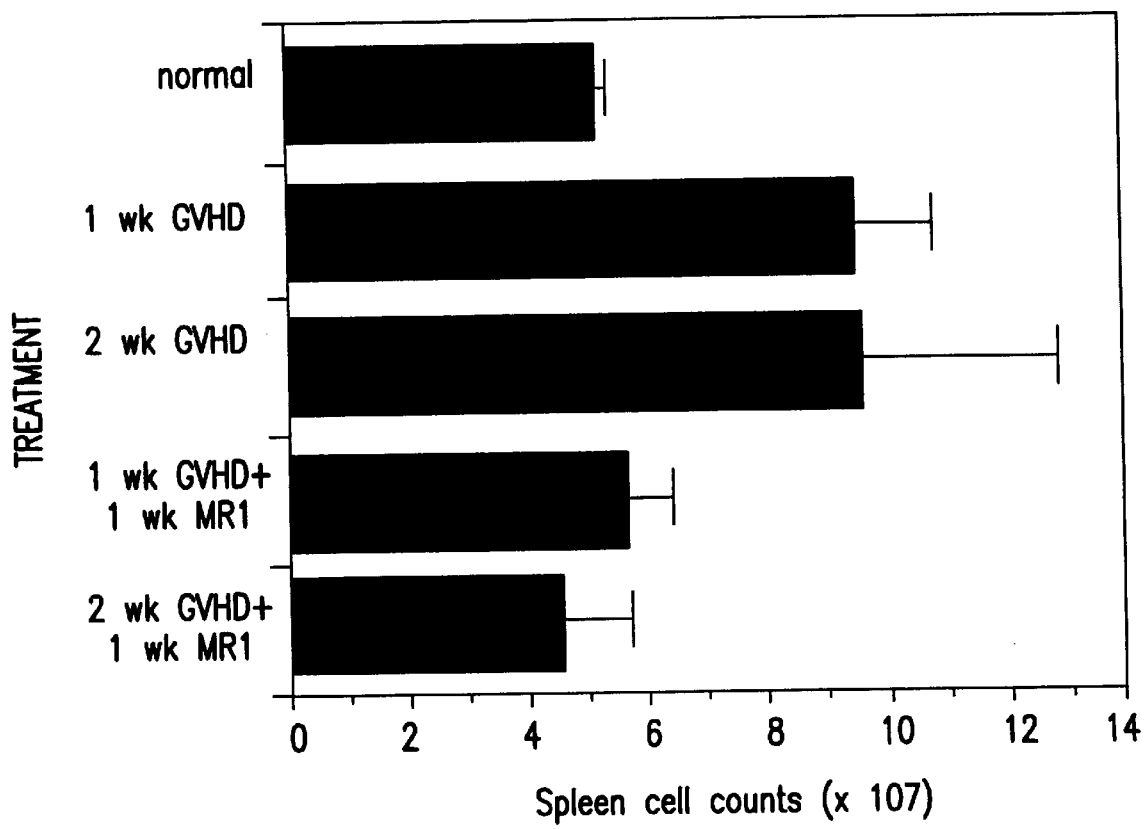

FIG. 37. Indicator for splenomegaly in GVHD-induced mice.

Spleen cell counts obtained from normal mice (B6D2F$_1$), 1 and 2 week GVHD induced mice and mice induced with GVHD while being treated with anti-gp39 antibody (MR1) (250 µl/ml) for 1 week and then terminated for a further 7 days.

Figure 38A:
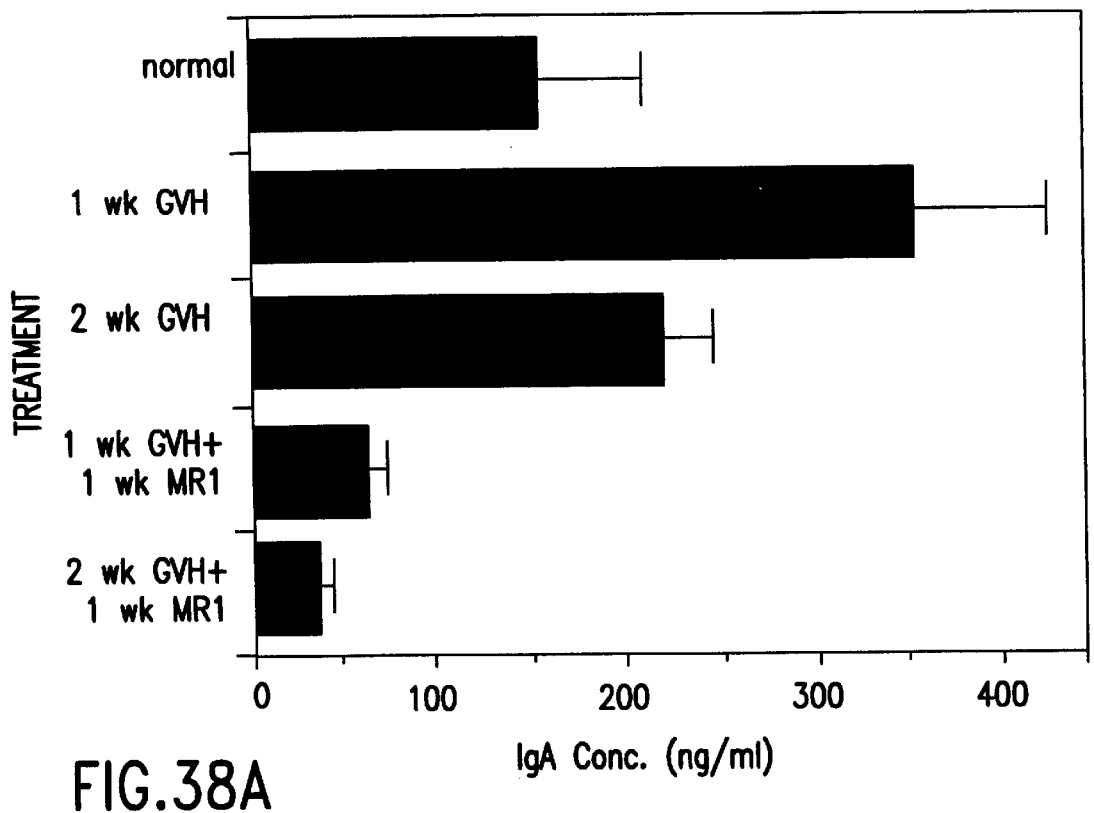

FIG. 38A. Hyperimmunoglobulin production in GVHD-induced mice and inhibition by anti-gp39.

Concentrations of IgA were obtained by culturing of spleen cells and performing ELISA assays on the supernatants.

Figure 38B:
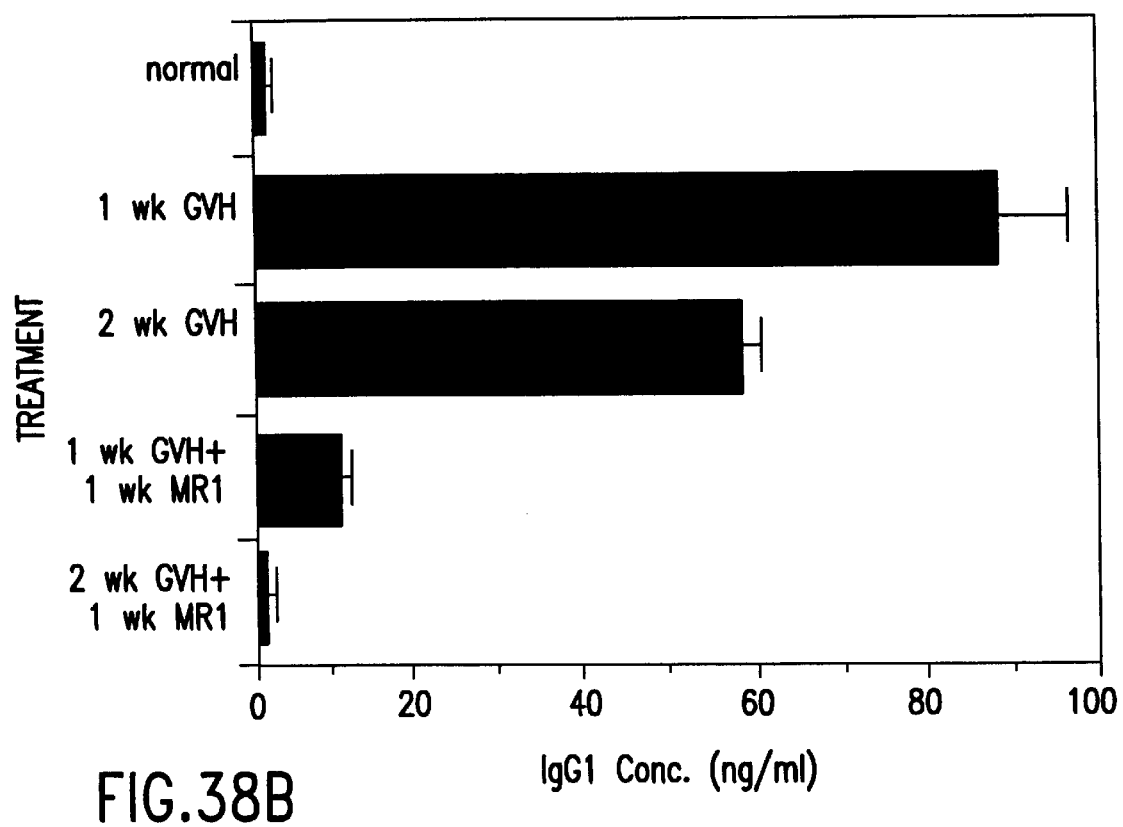

FIG. 38B. Hyperimmunoglobulin production in GVHD-induced mice and inhibition by anti-gp39.

Concentrations of IgG1 were obtained by culturing of spleen cells and performing ELISA assays on the supernatants.

5. DETAILED DESCRIPTION OF THE INVENTION

The present invention provides for substantially purified CD40CR; for soluble ligands of CD40CR, including antibodies as well as fusion molecules comprising CD40; and for methods of controlling B-cell activation.

For purposes of clarity of disclosure, and not by way of limitation, the detailed description of the invention is divided into the following subsections:

(i) ligands that bind to CD40CR;
(ii) methods used to characterize CD40CR;
(iii) preparation of purified CD40CR;
(iv) uses of ligands that bind to CD40CR; and
(v) uses of CD40CR.

5.1. Ligands That Bind to CD40CR

The present invention provides for soluble ligands of CD40CR, including (i) fusion molecules comprising at least a portion of CD40 protein and (ii) antibodies or antibody fragments.

The term "soluble," as used herein, indicates that the ligands of the invention are not permanently associated with a cell plasma membrane. Soluble ligands of the invention may, however, be affixed to a non-cellular solid support, including a lipid, protein, or carbohydrate molecule, a bead, a vesicle, a magnetic particle, a fiber, etc. or may be enclosed within an implant or vesicle.

The ability of such a ligand to bind to CD40CR may be confirmed by demonstrating that the ligand binds to the same protein as CD40-Ig (infra) or MR1 (infra).

The ligands of the invention may be comprised in pharmaceutical compositions together with a suitable carrier.

5.1.1. Fusion Molecules

The present invention provides for soluble fusion molecules that are ligands of CD40CR. Such fusion molecules comprise at least a portion of CD40 protein attached to a second molecule. The portion of CD40 preferably lacks the CD40 transmembrane domain. A portion of CD40 protein which may be used according to the invention is defined as any portion which is able to bind to CD40CR, for example, such a portion may be shown to bind to the same protein as MR1 or CD40-Ig.

Second molecules which may be used include peptides and proteins, lipids, and carbohydrates, and, in preferred embodiments of the invention, may be an immunoglobulin molecule, or portion thereof (such as an Fv, Fab, F(ab')$_2$, or Fab' fragment) or CD8, or another adhesion molecule, such as B7. The second molecule may be derived from either a non-human or a human source, or may be chimeric. The second molecule may also be an enzyme, toxin, growth factor, lymphokine, antiproliferative agent, alkylating agent, antimetabolite, antibiotic, vinca alkaloid, platinum coordinated complex, radioisotope, or a fluorescent compound.

The fusion molecules of the invention may be produced by chemical synthesis or, preferably, by recombinant DNA techniques.

For example, a nucleic acid sequence encoding at least a portion of CD40 protein may be combined with a nucleic acid sequence encoding a second molecule in a suitable expression vector, and then expressed in a prokaryotic or, preferably, eukaryotic expression system, such as a yeast, baculovirus, or mammalian expression system, including transgenic animals.

Alternatively, at least a portion of CD40 protein may be expressed using recombinant DNA techniques and then may be chemically conjugated to a second molecule.

Fusion molecules comprising CD40 may be purified from preparative mixtures using electrophoretic techniques or affinity chromatography using ligand that binds to either CD40 or to the second molecule. Ligands that bind to CD40 include, but are not limited to, anti-CD40 antibodies such as G28-5, as produced by the hybridoma having accession number HB9110 and deposited with the American Type Culture Collection, and CD40CR, described more fully in sections 5.2 and 5.3, infra. If the second molecule is an immunoglobulin or immunoglobulin fragment, an affinity column comprising anti-immunoglobulin antibody may be used; if the second molecule comprises an F$_c$ fragment, a protein A column may be used.

According to a preferred embodiment of the invention, a portion of CD40 may be produced using a nucleic acid sequence that encodes a CD40 protein that is truncated upstream from the transmembrane domain. Such a nucleic acid sequence may be prepared by digesting a plasmid containing a cDNA encoding CD40 antigen, such as that described in Stamenkovic et al., (1989), *EMBO J.* 8:1403–1410, with PstI (P) and Sau 3A (S3) restriction enzymes. The resulting P/S3 fragment may be subcloned into the same plasmid digested with P and Bam HI (B), to produce a truncated CD40 gene (see FIG. 8B).

In particular, nonlimiting, embodiments of the invention, an expression vector used to produce ligands containing at least a portion of CD40 as well as immunoglobulin sequence may preferably comprise (i) a virally-derived origin of replication, a bacterial origin of replication, a bacterial selectable marker, and eukaryotic promoter and enhancer sequences separated from DNA sequences encoding an immunoglobulin constant region by restriction endonuclease sites which allow subcloning of DNA sequences encoding at least a portion of CD40, followed by a polyadenylation signal sequence (see FIG. 8B.).

In a specific embodiment of the invention, the truncated CD40 gene may be subcloned into an immunoglobulin fusion plasmid, such as that described in Aruffo et al., 1990, *Cell* 61:1303–1313, using an Mlu I and B digest, to form plasmid pCD40-Ig, which encodes the fusion molecule CD40-Ig (see FIG. 8B). CD40-Ig fusion protein may then be produced by transfecting the pCD40-Ig plasmid into COS cells to form a transient expression system. CD40-Ig produced may be collected from the COS cell supernatant and purified by protein A column chromatography as described in Aruffo et al., 1990, *Cell* 161:1303–1313.

5.1.2. Antibodies

The soluble ligands of the invention may comprise antibody molecules, monoclonal antibody molecules, or fragments of these antibody molecules which contain an antigen combining site that binds to CD40CR. Such ligands may further comprise a second molecule which may be a protein, lipid, carbohydrate, enzyme, toxin, growth factor, lymphokine, antiproliferative agent, alkylating agent, antimetabolite, antibiotic, vinca alkaloid, platinum coordinated complex, radioisotope, or a fluorescent compound and may be linked to the antibody molecule or fragment.

Where the ligand is a monoclonal antibody, or a fragment thereof, the monoclonal antibody can be prepared against CD40CR using any technique which provides for the production of antibody molecules by continuous cell lines in culture. For example, the hybridoma technique originally developed by Kohler and Milstein (1975, Nature 256:495–497) as well as other techniques which have more recently become available, such as the human B-cell hybridoma technique (Kozbar et al., 1983, Immunology Today 4:72) and EBV-hybridoma technique to produce human monoclonal antibodies (Cole et al., 1985, Monoclonal Antibodies and Cancer Therapy, Alan R. Liss, Inc., pp. 77–96) and the like are within the scope of the present invention.

Antibody fragments which contain the idiotype of the molecule could be generated by known techniques. For example, such fragments include but are not limited to: the $F(ab')_2$ fragment which can be generated by treating the antibody molecule with pepsin; the Fab' fragments which can be generated by reducing the disulfide bridges of the $F(ab')_2$ fragment; the $F(ab')_2$ fragment which can be generated by treating the antibody molecule with papain; and the 2Fab or Fab fragments which can be generated by treating the antibody molecule with papain and a reducing agent to reduce the disulfide bridges.

The present invention also provides for chimeric antibodies produced by techniques known in the art, such as those set forth in Morrison et al., (1984) *Proc. Natl. Acad. Sci. U.S.A.* 81:6851–6855 or European Patent Application No. 85305604.2, publication No. 0173494 by Morrison et al., published Mar. 5, 1986.

Immunogen for the production of antibodies may be any source that contains CD40CR. For example, activated $T_h$ may be used as an immunogen. Alternatively, substantially purified CD40CR, prepared as set forth in section 5.3, infra, may be used. If activated $T_h$ are used as immunogen, antiserum may be tested for reactivity against activated but not resting $T_h$ cells.

In a preferred embodiment of the invention, the soluble ligand is the MR1 monoclonal antibody. The following method was used to produce the MR1 monoclonal antibody, and may be used to generate other antibodies directed toward CD40CR.

Hamsters were immunized intraperitoneally with 5–10$^6$ activated $T_h1$ cells (D1.6) at weekly intervals for six weeks. When the serum titer against murine $T_h1$ was greater than about 1:10,000, cell fusions were performed with polyethylene glycol using immune hamster splenocytes and NSI. SN from wells containing growing hybridomas were screened by flow cytometry on resting and activated $T_h1$. One particular hybridoma, which produced a mab that selectively recognized activated $T_h$, was further tested and subdloned to derive MR1. MR1 was produced in ascites and purified by ion exchange HPLC.

The present invention also provides for ligands comprising monoclonal antibodies, and fragments thereof that are capable of competitively inhibiting the binding of MR1 to its target antigen or CD40-Ig to its receptor.

5.2. Methods Used to Characterize CD40CR

CD40CR may be characterized by (i) its ability to bind CD40, fusion molecules comprising at least a portion of CD40, and antibodies such as MR1; (ii) its functional characteristic of being able to stimulate B-cell cycle entry, proliferation, and differentiation; and (iii) its cellular distribution.

5.2.1. Ability to Bind Ligands

CD40CR may be characterized by its ability to bind to ligands such as CD40, fusion molecules comprising CD40, and antibodies directed toward CD40CR.

As discussed in greater detail infra, several techniques were used to characterize CD40CR. For example, CD40-Ig and MR1 were shown to recognize the same 39 kD molecule. Both CD40-Ig and MR1 were found to immunoprecipitate a 39 kD protein from radiolabelled $T_h$ lysates (FIG. 5B). Further, immunoprecipitation of the 39 kD protein with CD40-Ig removed the antigen recognized by MR1 from $T_h$ lysates.

5.2.2. Ability to Stimulate B-Cells

CD40CR may also be characterized by its ability to stimulate B-cell cycle entry, proliferation, and differentiation.

For example, plasma membrane (PM) from activated ($PM^{Act}$) but not resting ($PM^{rest}$) $T_h$ cells was found to induce B-cell RNA synthesis (FIG. 1a); this induction, indicative of B-cell activation, was not affected by antibodies such as anti-LFA-1, anti-CD4, anti-ICAM-1. CD40-Ig or MR1, however, were found to be able to inhibit $PM^{Act}$-induced B-cell activation, as shown in FIG. 1B and FIG. 6.

The induction of B-cell activation may be measured by techniques such as [$^3$H]-uridine incorporation into RNA (as B-cells differentiate, RNA synthesis increases), or by [$^3$H]-thymidine incorporation, which measures DNA synthesis associated with cell proliferation. For optimal measurement of the effect of CD40CR on B-cell proliferation, interleukin-4 (IL-4) may be added to the culture medium at a concentration of about 10 ng/ml.

Alternatively, B-cell activation may be measured as a function of immunoglobulin secretion. For example, CD40CR, in substantially purified form, or as present in PM, or otherwise, may be added to resting B-cells together with IL-4 (10 ng/ml) and IL-5 (5 ng/ml). After three days of culture, an additional volume of culture medium may be added. On day 6 of culture, supernatant (SN) from individual cultures may be harvested and quantitated for IgM and $IG_1$ as described in Noelle et al., (1991) *J. Immunol.* 146:1118–1124.

5.2.3. Cellular Distribution

CD40CR may also be characterized by its cellular distribution. For example, CD40-Ig was observed to bind to activated, but not resting $T_h1$, as assessed by flow cytometry (FIGS. 3A–3B). Furthermore, CD40-Ig was observed to bind to Jurkat cells, HSB2 cells, and activated T-cells from human peripheral blood, but did not appear to bind significantly to CEM cells, HPBALL cells, or murine thymoma cells.

For example, and not by way of limitation, the presence of CD40CR on a particular cell type ("test cells") may be evaluated by flow cytometry as follows. Test cells may be tested in parallel with resting (negative control) and activated (positive control) $T_h$ cells. All cells may be incubated at a concentration of about $1\times10^5$ cells/50 µl with ligand (e.g. CD40-Ig or MR1) for 20 minutes at 4° C., followed by FITC-conjugated anti-ligand antibody. Propidium iodide may be added to all samples to a final concentration of 2 µg/ml. Flow cytometric analysis may then be performed, for example on a BD FACSCAN. After positive gating of cells by forward versus side scatter, and by red negativity (for propidium iodide exclusion), and the log green fluorescence of viable cells may be ascertained.

5.3. Preparation of Purified CD40CR

The present invention provides for substantially purified CD40CR. Such CD40CR may be prepared from cells bearing CD40CR, such as activated helper T-cells, Jurkat, and HSB2 cells, by the following method.

Plasma membranes may be prepared from appropriate cells, such as activated $T_h1$ cells, by discontinuous sucrose gradient sedimentation, as described in Noelle et al., 1991, J. Immunol. 146:1118–1124. CD40CR may then be isolated by dissociating the crude membrane extract with mild detergent, and then performing size exclusion chromatography followed by either affinity chromatography using appropriate ligands (e.g. MR1 or CD40-Ig) bound to a solid support, immunoprecipitation (e.g. by CD40-Ig or MR1), and/or gel electrophoresis.

The resulting protein may be expected to have a molecular weight of about 39 kD.

The present invention provides for a soluble CD40CR (i.e. cell-free) which may be comprised in pharmaceutical compositions together with a suitable carrier. It further provides for CD40CR which is linked to a second molecule which may be a peptide, protein, lipid, carbohydrate, enzyme, toxin, growth factor, lymphokine, antiproliferative agent, alkylating agent, antimetabolite, antibiotic, vinca alkaloid, platinum coordinated complex, radioisotope, or a fluorescent compound.

The present invention further provides for substantially purified CD40CR which has been prepared by chemical synthesis or recombinant DNA techniques. For example, the gene for CD40CR may be isolated by inserting cDNA prepared from activated helper T-cells into the λgt10 expression system, and then screening with MR1 or CD40-Ig binding to identify CD40CR-expressing clones. Alternatively, cDNA prepared from activated helper T-cells may be transfected into COS cells, the supernatants of which may be screened with MR1 or CD40-Ig to identify CD40CR producers. The gene for CD40CR may be then used to express CD40CR using expression systems known in the art.

5.4. Uses of Ligands That Bind to CD40CR

The present invention provides for methods of controlling B-cell activation that utilize ligands that bind to CD40CR. In particular, it provides for a method of inhibiting B-cell activation comprising exposing a mixture of B-cells and $T_h$ cells to an effective concentration of ligand that binds to CD40CR. Ligands that may be used are described supra in section 5.1. The method of the invention may be practiced in vitro or in vivo. An effective concentration refers to a concentration of a ligand that inhibits B-cell activation, measured by any technique known in the art (including those set forth in section 5.2, supra) by at least about 30 percent, and preferably by about 75 percent. According to a preferred, specific, non-limiting embodiment of the invention, CD40-Ig may be used as ligand, in which case an effective concentration may be at least about 10 µg/ml. In another specific, nonlimiting embodiment of the invention, the monoclonal antibody MR1 may be used, in which case an effective concentration may be at least about 10 µg/ml. If the method is practiced in vivo, an effective concentration of ligand may refer to plasma concentration of ligand or to a local concentration. For example, it may be desirable to inhibit B-cell activation in a localized area in order to limit the effects on the immune system as a whole.

In particular embodiments, the invention provides for a method of treating a subject suffering from a disorder associated with B-cell activation, comprising administering to the subject a therapeutic amount of ligand that binds to CD40CR. A subject may be a non-human or, preferably, a human animal.

Disorders associated with B-cell activation include, but are not limited to, allergy (including anaphylaxis); autoimmune conditions (see Section 12, infra, which demonstrates the effectiveness of CD40CR ligand in a murine model of rheumatoid arthritis) including drug induced lupus, systemic lupus erythematosus, adult rheumatoid arthritis, juvenile rheumatoid arthritis, scleroderma, Sjogren's Syndrome, etc.; and viral diseases that involve B-cells, including Epstein-Barr infection, and retroviral infection including infection with a human immunodeficiency virus.

Because it has been suggested that B-cell activation is associated with the induction of human immunodeficiency virus replication from latency, it may be desirable to administer the ligands of the invention to HIV positive individuals who have not yet developed AIDS or ARC.

The present invention further provides for methods comprising administering an effective amount of CD40CR ligand to reduce a primary and/or secondary humoral immune response to thymus dependent antigen, which methods do not substantially alter the humoral response to thymus-independent type II antigens, (see Section 9, infra). In specific, nonlimiting embodiments, the CD40CR ligand may be a monoclonal antibody administered to a human subject at a dose between 0.1 mg and 20 mg/kg body weight. It is important to note that, as shown in Section 9, CD40CR ligand has been demonstrated to prevent primary and secondary humoral responses to heterologous antibody preparations, thereby improving the therapeutic potential of such heterologous antibody preparations in patient treatment by permitting repeated administration of heterologous antibody without invoking substantial humoral immunity.

In additional embodiments of the invention, CD40CR ligand may be used to prevent or ameliorate graft versus host disease in a subject in need of such treatment. Accordingly, the invention provides for methods of inhibiting graft versus host disease in a subject in need of such treatment comprising an effective amount of CD40CR ligand to a subject in need of such treatment. See Sections 11 and 13 for data demonstrating that anti-gp39 antibody was able to inhibit grafted T cells from inducing host B cell activation.

Ligands may be administered, in a suitable pharmaceutical carrier, by any method known in the art, including intravenous, intraperitoneal, subcutaneous, intrathecal, intraarticular or intramuscular injection, and oral, intranasal, intraocular and rectal administration, and may be comprised in microspheres, liposomes, and/or sustained release implants.

A therapeutic amount of ligand is defined as an amount which significantly diminishes the deleterious clinical effects of B-cell activation, and may vary among ligands used and conditions treated. If CD40-Ig is used, therapeutic concentration may be about 10 µg/ml either systemically (plasma concentration) or locally. If MR1 is used, a therapeutic concentration may be about 10 µg/ml either systemically (plasma concentration) or locally.

In a further embodiment of the invention, the above methods may utilize a ligand comprising a toxin or antimetabolite such that $T_h$ cells are killed or damaged and B-cell activation is decreased as a result of $T_h$ cell destruction.

The ligands of the invention may also be used to label activated T cells, a technique which may be useful in the diagnosis of T cell disorders. To this end, ligand comprising an enzyme, radioisotope, fluorescent compound or other detectable label may be exposed to T cells in vitro or in vivo and the amount of binding may be quantitated.

The ligands of the invention may also be used to deliver substances, e.g. growth factors, to activated T-cells.

5.5. Uses of CD40CR

The present invention provides for methods of controlling B-cell activation that utilize CD40CR or a molecule comprising CD40CR, prepared as described in section 5.3, supra. In particular, it provides for a method of promoting B-cell activation comprising exposing B-cells to an effective concentration of CD40CR. The method may be practiced in vivo or in vitro. An effective concentration refers to a concentration of receptor that induces B-cell activation, measured by any technique known in the art (including those set forth in section 5.3, supra) by at least about 30 percent. In specific, nonlimiting embodiments of the invention, the concentration of CD40CR may be about 10 µg/ml locally or systemically.

In particular embodiments, the invention provides for a method of treating a subject suffering from an immunodeficiency disorder associated with diminished humoral immunity, comprising administering to the subject a therapeutic amount of CD40CR. A subject may be a non-human or, preferably, a human animal.

Immunodeficiency disorders associated with diminished humoral immunity include acquired immunodeficiency syndrome, immunodeficiency associated with malignancy or cachexia, iatrogenic immunodeficiency caused, for example, by chemotherapy or radiation therapy, as well as genetic disorders involving humoral immunity.

CD40CR may be administered,in a suitable pharmaceutical carrier, by any method known in the art, including intravenous, intraperitoneal, subcutaneous, intrathecal, intraarticular, or intramuscular injection, and oral,intranasal, intraocular, and rectal administration and may be comprised in microspheres, liposomes, and/or sustained release implants.

A therapeutic amount of CD40CR for CD40 is defined as that amount which increases immunoglobulin production by at least about 30 percent.

In a further embodiment, CD40CR may be conjugated to a toxin, and then administered to a subject under circumstances in which it would be preferable to destroy B-cells that express CD40. Examples of such circumstances include patients receiving organ transplants or suffering from multiple myeloma or another B-cell malignancy,or from autoimmune disease.

CD40CR may also be used to label B-cells expressing CD40, a technique which may be useful in the diagnosis of B-cell disorders. To this end, receptor linked to an enzyme, radioisotope, fluorescent compound or other detectable label may be exposed to B-cells in vivo or in vitro and the amount of binding may be quantitated.

CD40CR may also be used to deliver molecules that are linked to it to B-cells.

6. EXAMPLE

A Novel Receptor, CD40CR, on Activated Helper T-Cells Binds CD40 and Transduces the Signal for Cognate Activation of B-Cells

6.1. Materials and Methods

6.1.1. Animals

Female DBA/2J mice (Jackson Laboratories, Bar Harbor, Me.) were used for the preparation of filler cells to support the growth of $T_h$ clones and in the preparation of resting B-cells.

6.1.2. Helper T-Cell Clones ($T_h$)

D1.6, a I-$A^d$-restricted, rabbit Ig-specific $T_h1$ clone (Kurt-Jones et al., (1987) *J Exp Med* 166:1774–1787) was obtained from Dr. David Parker, University of Mass. at Worcester. D1.6 will be referred to herein as $T_h1$.

6.1.3. Activation of $T_h$ by Anti-CD3

$T_h1$ were cultured ($8\times10^6$/well) in cluster wells (6 well, Corning, N.Y.) coated with 40 µg/4 ml of PBS/well with anti-CD3 for 16 hours, as described in (Noelle et al., (1991) *J. Immunol.* 146:1118–1124).

6.1.4. Preparation of $T_h$ Plasma Membranes

Plasma membranes were prepared by discontinuous sucrose gradient sedimentation, as described in (Noelle et al., (1991) *J. Immunol.* 146:1118–1124).

6.1.5. Preparation of Resting B-Cells

Resting splenic B-cells were prepared by sedimentation on discontinuous Percoll gradients, as described in (Defranco et al., (1982) *J. Exp. Med.* 155:1523). Cells isolated from the 70–75% (density of 1.087–1.097) Percoll interface were typically >95% mIg$^+$, had a uniform, low degree of near forward light scatter and were unresponsive to Con A.

6.1.6. Antibodies

The following mabs were purified by ion exchange HPLC from ascites fluid of mice which had been irradiated and bone marrow reconstituted: anti-CD3:145-2C11 (Leo et al., (1987) *Proc. Natl. Acad. Sci. USA* 84:1374–1378); anti-α, β:H57-597; anti-CD4: GK1.5 (Wilde et al., (1983) *J. Immunol.* 131:2178–2183); anti-ICAM:YN1/1.7.4 (Prieto et al., (1989) *Eur. J. Immunol.* 19:1551–1557); anti-LFA-1: FD441.8 (Sarmiento et al, (1982) *Immunol. Rev.* 68:135); and anti-rat/hamster κ chain:RG-7 (Springer, (1982) *Hybrid.* 1:257–273).

6.1.7. Preparation of the CD40 Recombinant Globulin (CD40-Ig)

The CD40 fusion protein was prepared by digesting a plasmid containing a cDNA encoding the CD40 antigen (Stamenkovic and Seed, (1989) *EMBO J.* 8:1403–1410) with the restriction enzyme Pst I (P) and Sau 3A (S3). This P/S3 fragment was subcloned into the same plasmid digested with P and Bam H1 (B). This allowed the preparation of the CD40Δ which encoded a CD40 protein truncated upstream from the transmembrane domain. The DNA fragment encoding a CD40Δ was then subcloned into the immunoglobulin fusion plasmid (Aruffo et al. (1990), *Cell.* 61:1303–1313) using a MluI and B digest. The CD40-Ig fusion protein was produced by transient transfection in COS cells and purified on a protein A column as described in (Aruffo et al., (1990) *Cell.* 61:1303–1313).

6.1.8. Lymphokines

Interleukin 4 (IL4): Recombinant mouse IL4 was generously provided by Drs. C. Maliszewski and K. Grabstein, Immunex Corporation, Seattle, Wash.

Interleukin 5 (IL5): Recombinant mouse IL5 was purchased from R&D Research, Sarrento, Calif.

6.1.9. Induction of B-cell RNA Synthesis by Activated $T_h$ Plasma Membranes $3 \times 10^4$ resting B-cells were cultured in 50 μl of cRPMI in A/2 microtiter wells (Costar, Cambridge, Mass.). To these wells, 0.5 μg of $T_h 1$ or $T_h 2$ membrane protein was added. From 42–48 hrs, wells were pulsed with 2.5 μCi of $^3$H-uridine (New England Nuclear, Boston Mass.), harvested, and the radioactivity determined by liquid scintillation spectroscopy. The results were expressed as cpm/culture +/−s.d.

6.1.10. Induction of B-Cell Immunoglobulin Secretion by Activated $T_h$ Plasma Membranes and Lymphokines Resting B-cells were cultured as described above. To culture wells, 0.5 μg of $T_h 1$ membrane protein, IL4 (10 ng/ml) and IL5 (5 ng/ml) were added. On day three of culture, an additional 50 μl of cRPMI was added. On day six of culture, SN from individual wells were harvested and quantitated for IgM and $IgG_1$, as described in (Noelle et al., (1991) *J. Immunol.* 146:1118–1124).

6.1.11. Induction of B-cell Proliferation by Activated $T_h$ and IL4

$4 \times 10^4$ resting B-cells were cultured in 50 μl of cRPMI in A/2 microtiter wells (Costar, Cambridge, Mass.). To these wells, $1 \times 10^4$ resting or activated, irradiated (500 rads) $T_h 1$ and IL4 (10 ng/ml) were added. On day three of culture, wells were pulsed with 1 μCi of $^3$H thymidine, as described in (Noelle et al., (1991) *J. Immunol.* 146:1118–1124).

6.1.12. Production of Monoclonal Antibodies Specific to Membrane Proteins Induced on Activated $T_h 1$ Hamsters were immunized intraperitoneally with 5–10× $10^6$ activated $T_h 1$ (D1.6) at weekly intervals for six weeks. When the serum titer against murine $T_h 1$ was greater than 1:10,000, cell fusions were performed with polyethylene glycol using immune hamster splenocytes and NS1. SN from wells containing growing hybridomas were screened by flow cytometry on resting and activated $T_h 1$. One particular hybridoma, which produced a mab that selectively recognized activated $T_h$, was further tested and subcloned to derive MR1. MR1 was produced in ascites and purified by ion exchange HPLC.

6.1.13. Flow Cytofluorometric Analysis of Activation Molecules Expressed on $T_h$ Resting and activated $T_h$ (16 hours with anti-CD3) were harvested and incubated at $1 \times 10^5$ cells/50 μl with fusion protein for 20 minutes at 4° C., followed by FITC-conjugated goat anti-human (h)IgG (25 μg/ml; Southern Biotechnology, Birmingham, Ala.). To all samples, propidium iodide was added at final concentration of 2 μg/ml. Flow cytofluorometric analysis was performed on a BD FACSCAN. After positive gating of cells by forward versus side scatter, and by red negativity (for propidium iodide exclusion), the log green fluorescence of viable cells is was ascertained. At least 5,000 viable cells were analyzed for the determination of percent positive cells and MFI. Staining with MR1 employed FITC-conjugated RG7, a mouse anti-rat/hamster κ chain mab.

6.1.14. Biosynthetic Labelling, Immunoprecipitation, SDS-PAGE and Fluorography $T_h 1$ were rested or activated with insolubilized anti-CD3 for 16 hrs. Proteins from resting and activated $T_h$ ($20 \times 10^6$/ml) were labelled with 1 mCi of [$^{35}$S]-methionine/cysteine for one hour, at which time they were washed twice in RPMI/10% FCS and the cell pellet was lysed in extraction buffer, as described (Noelle et al., (1986) *J. Immunol.* 137:1718–1726). Purified antibodies or fusion proteins (1–10 μg) were added to 500 μl of lysate ($5 \times 10^6$ cell equivalents) at 4° C. for 16 hours. At that time, the lysates were transferred to tubes containing 50 μl of packed Protein A-sepharose. The pelleted Protein A-Sepharose was resuspended and tubes were incubated at 4° C. for 1 hr with agitation. The samples were then washed 3× with high stringency wash buffer. The pelleted protein A-Sepharose was resuspended in 30 μl of SDS sample buffer and run on a 10% polyacrylamide gel. After running the gel, the gel was fixed and fluorography performed.

6.2. Results

6.2.1. Effect of Monoclonal Antibodies on the Induction of B-Cell RNA Synthesis by $PM^{Act}$ In order to define the cell surface molecules that mediated the induction of B-cell cycle entry by $PM^{Act}$, mabs to $T_h$ membrane proteins were added to cultures of PMAOt and B-cells. $PM^{Act}$ induced B-cell RNA synthesis eight-fold over that observed with $PM^{rest}$ (FIG. 1). The addition of anti-LFA-1, anti-CD4, anti-ICAM-1, alone, or in combination, did not inhibit the induction of B-cell RNA synthesis by $PM^{Act}$.

6.2.2. CD40-Ig Inhibited $T_h$-Induced B-cell Cycle Entry, Differentiation and Proliferation In the human system, it had been shown that anti-CD40 mab induced B-cell proliferation (Clark and Lane, (1991) *Ann. Rev. Immunol.* 9:97–127) thereby implicating CD40 as an important triggering molecule for B-cells. To determine if CD40 was involved in the induction of B-cell RNA synthesis by $PM^{Act}$, a soluble fusion protein of the extracellular domains of human CD40 and the $F_c$ domain of human $IgG_1$ (CD40-Ig) was added to cultures of $PM^{Act}$ and B-cells. $PM^{Act}$ derived from $T_h 1$ and $T_h 2$ were prepared and used to stimulate B-cell RNA synthesis. The addition of CD40-Ig to culture caused a dose-dependent inhibition of B-cell RNA synthesis that was induced by $PM^{Act}$ from $T_h 1$ and $T_h 2$ (FIG. 1B). Half-maximal inhibition of B-cell RNA synthesis induced by PM$^{Act}$ from T$_h$1 and T$_h$2 was about 5 μg/ml CD40-Ig. A CD7E-Ig fusion protein (Damle and Aruffo, (1991) *Proc. Natl. Acad. Sci. USA* 88:6403–6407) was without effect even when used at 25 μg/ml.

To investigate whether CD40-Ig inhibited the activation of B-cells by T-independent activators, B-cells were cultured in the presence of LPS and CD40-Ig. On day 2, RNA synthesis was assessed (FIG. 1C). CD40-Ig was ineffective at inhibiting B-cell activation by LPS, yet inhibited the response of B-cells to PM$^{Act}$.

In the presence of PM$^{Act}$, IL4 and IL5, B-cells polyclonally differentiated to produce Ig (Hodgkin et al., (1990) *J. Immunol.* 145:2025–2034; Noelle et al., (1991) *J. Immunol.* 146:1118–1124). To evaluate the requirements for CD40 signalling in this process, CD40-Ig was added at the initiation of culture, or on subsequent days of culture. The addition of CD40-Ig (FIG. 2A) at the initiation of culture inhibited greater than 95% of polyclonal IgM and IgG$_1$ production compared to control levels in its absence. In contrast, the addition of CD40-Ig on day 1 and 2 of culture showed little, if any, inhibitory effect on IgM and IgG$_1$ production. These data indicated that after 24 hours, signalling via CD40 is no longer essential for the differentiation of B-cells to Ig secretion.

Data thus far indicated that CD40 was implicated in the activation of B-cells by PM$^{Act}$. Studies were performed in order to ensure that CD40 was also involved in the activation of B-cells by intact, viable, activated T$_h$. T$_h$1 were activated for 16 hours with insolubilized anti-CD3, harvested and irradiated. The irradiated T$_h$1 were cultured with B-cells in the presence of IL4 and B-cell proliferation was determined on day 3 of culture. An exogenous source of IL4 was required to achieve B-cell proliferation with T$_h$1, because T$_h$1 do not produce IL4 (Noelle et al., (1989) *J. Immunol.* 143:1807–1814). CD40-Ig inhibited the induction of B-cell proliferation by irradiated T$_h$ in a dose-dependent manner, similar to that observed with PM$^{Act}$ (FIG. 2B). The negative control, CD7E-Ig, exerted no appreciable effect.

6.2.3. CD40-Ig Detected a Molecule Expressed on Activated, but not Resting T$_h$ To investigate whether activated T$_h$1 express is a binding protein for CD40, resting and activated (16 hours) T$_h$1 were stained with CD40-Ig or CD7E-Ig, followed by FITC-anti-HIgG. Binding of CD40-Ig was assessed by flow cytometry (FIGS. 3A–3B). T$_h$1 that were activated for 16 hours with anti-CD3, but not resting T$_h$1, stained 56% positive with CD40-Ig, but not with the control CD7E-Ig. To identify the CD40-Ig binding protein, T$_h$1 proteins were biosynthetically labelled with [$^{35}$S]-methionine/cysteine and proteins immunoprecipitated with CD40-Ig or CD7E-Ig. The immunoprecipitated proteins were resolved by SDS-PAGE and fluorography (FIG. 4). A prominent band with an apparent molecular weight of 39 kD immunoprecipitated in a dose-dependent manner with 1 and 10 μg of CD40/sample. As controls, anti-class I mab immunoprecipitated bands at 55 kD and a low molecular weight band, β2 microglobulin. In the absence of mab, no prominent bands were visible. A 39 kd band was also immunoprecipitated from activated T$_h$ that were vectorially labelled with $^{125}$I, confirming that the 39 kD protein was a membrane protein.

6.2.4. Monoclonal Antibody MR1, Specific to 39 Kd T$_h$ Membrane Protein, Inhibited the Induction of B-Cell RNA Synthesis by PM$^{Act}$ Mabs specific to antigens selectively expressed on activated versus resting T$_h$ were developed to identify T$_h$ molecule(s) responsible for the T$_h$ effector phase activity. One such mab, MR1, recognized an antigen that was selectively expressed on activated T$_h$1. To investigate whether MR1 and CD40-Ig recognized the same molecule, flow cytometry and blocking studies were performed. CD40-Ig and MR1 stained approximately 56% and 61%, respectively, of activated, but not resting Th FIG. 5A. MR1, but not another hamster anti-T cell mab, anti-α/β TCR, blocked the staining of activated T$_h$1 with CD40-Ig, in a dose-dependent manner. These data suggested that CD40-Ig and MR1 recognized overlapping or identical epitopes on the 39 kD Th protein. To further demonstrate that CD40-Ig and MR1 recognized the same molecule, the antigen that bound MR1 was identified by immunoprecipitation of proteins from radiolabelled Th lysates. Both CD40-Ig and MR1 immunoprecipitated a 39 kD protein (FIG. 5B). Finally, immunoprecipitation of the 39 kD protein with CD40-Ig removed the antigen recognized by MR1 from radiolabelled lysates of activated T$_h$ supporting the tenet that the MR1 antigen and the CD40 binding protein were identical.

Functional studies were performed with MR1 to address whether this mab neutralized the activity expressed by PM$^{Act}$. PM$^{Act}$ and B-cells were cultured alone, or in the presence of hamster mabs or CD40-Ig. Two hamster mabs, anti-α/β TCR and α-CD3 did not inhibit the activation of resting B-cells by PM$^{Act}$. In contrast, MR1 or CD40-Ig inhibited B-cell activation (FIG. 6).

6.3. Discussion

The data show that blocking of prominent T$_h$ surface molecules (LFA-1, CD4, ICAM-1, CD3, α,β TCR) with mabs did not impede the capacity of activated T$_h$ to induce B-cell cycle entry. In contrast, CD40-Ig or a maB specific to the CD40 binding protein, blocked T$_h$-dependent B-cell activation in a dose-dependent manner. Furthermore, the CD40 binding protein was identified as a 39 kD protein that is selectively expressed on the membranes of activated, but not resting T$_h$. Both CD40-Ig and a mab specific to the 39 kD CD40 binding protein blocked B-cell activation by PM$^{Act}$.

Although a number of membrane proteins have been implicated in T$_h$-dependent B-cell signalling, evidence presented herein dismisses the contribution of some molecules (LFA-1, CD4, CD3, α,β TCR, ICAM-1) and implicates CD40 as the B-cell receptor for cognate signalling by T$_h$. Data show that CD40-Ig and a mab specific to the CD40 binding protein inhibits T$_h$-dependent B-cell activation.

The ligand for CD40 is a 39 Kd protein that is expressed on activated, but not resting T$_h$. Biochemical studies indicate that the 39 kD protein is a single chain molecule since electrophoretic migration was not influenced by reducing agents. Based on the functional studies presented in this study, both activated T$_h$1 and T$_h$2 express the 39 kD CD40 binding protein. This is consistent with the functional studies that show both T$_h$1 and T$_h$2 induce B-cell cycle entry. In an attempt to further characterize the 39 kD protein, cDNA encoding CD proteins in the MW range of 39 kD (CD 53, CD27 and CD69) were transiently transfected into COS cells and the cells were tested for CD40-Ig binding. None of the transfected COS cells expressed proteins that bound CD40-Ig. It is therefore suspected that the 39 kD protein is not one of these CD proteins.

The biochemical basis for signal transduction between T$_h$ and B-cells has been elusive. The identification of CD40 as the signal transducing molecule for T cell help focusses attention on specific biochemical pathways known to be coupled to the CD40 molecule. CD40 is a member of the nerve growth factor receptor (NGFR) family by virtue of the presence of four cysteine-rich motifs in its extracellular region. Signaling through CD40 by mab has been shown (Uckun et al., (1991) *J. Biol. Chem.* 266:17478–17485) to involve the activation of tyrosine kinases resulting in the increased production of inositol trisphosphate and the activation of at least four distinct serine/threonine kinases. Based on information obtained from signaling through other members of the NGF receptor family, it is anticipated that interaction between activated $T_h$ and B will result in many of the same biochemical processes.

7. EXAMPLE

Binding of CD40 Ig to Human T-Cell Lines

For immunofluorescence binding studies, CD40 Ig fusion protein was conjugated with biotin using biotin-succinimide (Sigma). Flow cytometry analysis was then performed by tow-step staining using phycoerythrin (PE)-strepavidin (Bectin-Dickinson) with a Coulter Epics C instrument. Representative results of screening multiple T cell lines is presented below. The Jurkat and HSB2 cell lines were found to bind specifically, whereas other T cell lines including CEM, HPBALL, and murine thymoma did not bind the CD40 Ig fusion protein (FIGS. 7A–7C).

8. EXAMPLE

In Vivo Expression of CD40 Ligand, Cytokines and Antibody Production Delineates Sites of Cognate T-B Cell Interactions Interactions between T cells and B cells have a central role in the development of antibody responses. Upon activation, $T_h$ cells express the ligand for CD40, gp39, which is essential for $T_h$ cell dependent B cell activation. The cytokines produced by activated $T_h$ cells have a regulatory role in B cell differentiation. In this study, immunohistochemical techniques were used to investigate the in vivo time course and localization of gp39-expression and cytokine-production in relation to specific antibody production.

8.1. Materials and Methods

8.1.1. Animals

BCBA.F$_1$, mice were bred at the TNO breeding facilities, Rijswijk, The Netherlands. Animals were used at 16–24 weeks of age and were kept under a standard protocol with free access to pelleted food and acidified water (pH 3). Experiments were performed under auspices of the Dutch Veterinary Inspection, as described in the law on animal experiments.

8.1.2. Chemicals

Alkaline phosphatase (AP; P-6774, type VII-T, 1020 U/mg protein), 3-amino-9-ethylcarbazole (AEC; A-5754), Complete Freunds Adjuvant (CFA), 3,3-diaminobenzidine-tetrahydrochloride (DAB), Fast blue BB Base (F-0125), Fast red, horseradish peroxidase (HRP), Incomplete Freunds Adjuvant (IFA), levamisole, naphthol AS-MX phosphate (3-hydroxy-2-naphtoic acid 2,4-dimethyl-anilide), were obtained from Sigma, St. Louis, Mo., USA. N-hydroxysuccinimidyl-(biotinamido)-hexanoate and MHS (maleimidohexanoyl-n-hydroxysuccinimide ester) were obtained from Pierce, Rockford, Ill., USA. β-galactosidase (β-gal; *E. coli*-derived β-D-galactoside galactohydrolase, MW 540 KD), and X-Gal (5-bromo-4-chloro-3-indolyl-β-D-galactopyranoside) were obtained from Boehringer, Mannheim, FRG.

8.1.3. Reagents

TNP-Ficoll and TNP-KLH were prepared as previously described (Claassen et al. (1986) *Eur. J. Immunol.* 16:271), Claassen et al. (1986) *Eur. J. Immunol.* 16:492). The rat mAb Lyt2+ (CD8) (clone 53.6.7.2) (Ledbetter et al. (1979) *Immunol. Rev.* 47:63) and L3T4 (CD4)(clone GK-1.5) (Dialynas et al. (1983) *J. Immunol.* 131:2445) were used as cell markers. The control hamster antibodies and ascites from the cell lines MR1 (Noelle et al. (1992) *Proc. Natl. Acad. Sci. USA* 89:6550), a mAb directed to gp39 and RG7, a mAb specific for rat/hamster Igκ (RG-7; (Springer (1982) *Hybrid* 1:257)) chain were purified by means of a protein-A column. Anti-human IgG1 (3.1.1; (Boersma et al. (1989) *Prot. Biol. Fluids.* 36:157)) and Human IgG1 were obtained from Nordic Immunol. Labs, Tilburg, The Netherlands. The murine mAb DB-1 directed to IFN-γ, was a kind gift of Dr. P. H. van der Meide (Van der Meide et al. (1989) *Lymphokine Res.* 8:439). The cells of the rat mAb 11B11, directed to IL-4, and IL-4 were a kind gift of Dr. W. E. Paul, Laboratory of Immunology, National Institute of Allergy and Infectious Diseases, N.I.H., Bethesda, Md. (Ohara et al. (1985) *Nature* 315:333). The IL-2 specific mAb, S4B6, was a kind gift of Dr. T. Mosmann (Mosmann (1986) *J. Immunol.* 136:2348). Control rat mAb (2A4, 1G11) were a kind gift of Dr. A. Zantema, Sylvius Laboratory, Leiden, The Netherlands (Zantema et al. (1985) *Virology* 142:44). Recombinant mouse IL-2 was obtained from Genzyme, Cambridge, Mass., USA. The X6310 cell lines producing IL-4 or IL-2 were a kind gift of Dr. F. Melchers, Basel Institute of Immunology, Basel, Switzerland (Karasuyama et al. (1988) *Eur. J. Immunol.* 18:97). Antibodies were purified from culture supernatants using an affinity chromatography goat anti-rat Ig column. Cytokine-specific, gp39-specific and control antibodies were conjugated to AP and HRP, as described in (Claassen et al. (1988) *J. Histochem. Cytochem* 36:1455). Conjugation to β-gal was performed according to the procedure described by Deelder and De Water (Deelder et al. (1981) *Histochem. and Cytochem.* 29:1273) with minor modifications (Van der Eertwegh et al. (1992) *Eur. J. Immunol.* 22:719). TNP-AP and KLH HRP was prepared according to the methods described in (Claassen et al. (1986) *Eur. J. Immunol.* 16:271, Claassen et al. (1986) *Eur. J. Immunol.* 16:492).

BCBA.F$^1$ mice were injected i.v. with 100 μg of KLH or TNP-KLH or 20 μg of TNP-Ficoll and killed after 0, 1, 2, 3, 4, 5, 6, and 7 days. Another group of mice was injected with 100 μg of KLH, boosted 16 weeks later with 100 μg TNP-KLH and killed after 0, 1, 2, 3, 4, 5 and 7 days. In a parallel experiment, mice were immunized I.p. with TNP-KLH in CFA, boosted 4 weeks later I.p. with 20 μg TNP-KLH in IFA and killed 6 days after injection. Spleens and popliteal lymph nodes were removed and immediately frozen in liquid nitrogen and stored at −70° C.

8.1.4. Immunohistochemistry

Splenic cryostat sections (−20° C., 8 μm), one for every mouse, were picked up on the same glass slide and kept overnight under high humidity at RT. Slides were air-dried and stored in air-tight boxes until use. Slides were fixed for 10 minutes in acetone containing 0.02% $H_2O_2$. Slides were incubated horizontally overnight at 4° C. with primary cytokine-specific antibody-conjugates diluted in PBS containing 0.1% BSA and titrated to obtain optimal results. Immunohistochemical demonstration of gp39 was performed in two ways: first, with a gp39-specific hamster mAb, MR-1, followed by a hamster-Ig-specific mAb, RG-7, conjugated to peroxidase; second, with a fusion-protein of the gp39 receptor, CD40-IgG1 (Noelle et al. (1992) Proc. Natl. Acad. Sci. USA 89:6550), followed by a human-IgG1-specific mAb conjugated to peroxidase. For double staining of gp39 and CD4 or CD8, spleen sections were incubated simultaneously with MR-1-AP and L3T4-HRP or Lyt2$^+$-HRP. Detection of KLH-specific antibody forming cells (KLH-AFC) and TNP-AFC were detected according to previously described methods (Claassen et al. (1986) Eur. J. Immunol. 16:271), (Claassen et al. (1986) Eur. J. Immunol. 16:492). Slides were washed with PBS (three times 5 minutes) and immunohistochemical revelation was performed as described previously; AP (Claassen et al. (1988) J. Histochem. Cytochem 36:1455), HRP (Claassen et al. (1988) J. Histochem. Cytochem 36:1455) and β-gal (Deelder et al. (1981) Histochem and Cytochem. 29:1273). For double staining the immunohistochemical revelation of AP was performed prior to HRP, and the β-gal staining prior to AP or HRP, because both the peroxidase substrate as well as the AP substrate were found to inhibit the β-gal activity. To ensure that no over- or understaining occurred, slides with adherent substrate solution were monitored by light microscopy during histochemical reactions. Sections were counterstained with hematoxylin and mounted in glycerin-gelatin. Antibody-forming cells, gp39$^+$ cells and cytokine-PC were counted, and image-analysis was performed as previously described (Van den Eertwegh (1991) J. Immunol. 147:439). A minimum of three sections of each mouse were examined.

8.2. Results

8.2.1. Gp39 Expression in Immune Spleen

Spleen sections from mice immunized with KLH were stained for the expression of gp39. Two gp39-specific reagents were used for detection: first, MR1, a gp39-specific mAb, and second, CD40-IgG1, a soluble, recombinant fusion protein of the gp39 receptor and IgG1. In serial spleen sections CD40-IgG1 and anti-gp39 identified the same number of cells, which were localized in identical anatomical locations (FIG. 9A and 9B). Moreover, MR1 blocked the staining with CD40-IgG1 in a dose-dependent manner, confirming the fact that MR1 and CD40-IgG1 recognize the same molecule, gp39 (Noelle et al. (1992) Proc. Natl. Acad. Sci. USA 89:6550). Immunohistochemical double staining, using anti-gp39 and anti-CD4 mAb, showed that gp39 expression was restricted to the CD4 lineage cells (FIG. 9C).

TABLE I

Localization of gp39$^+$ cells in different compartments of the spleen after immunization with thymus (in)dependent antigens.

| Immunization[a] | Day[b] | Reagent[c] | Fc[d] | GC | iP | oP | MZ | TA | Red pulp |
|---|---|---|---|---|---|---|---|---|---|
| Saline | 4 | MR-1 | 0[e] | 0 | 0 | 2 ± 2 | 0 | 7 ± 5 | 0 |
| TNP-KLH: primary | 4 | CD40-Ig | 0 | 0 | 0 | 16 ± 7 | 0 | 115 ± 16 | 0 |
|  | 4 | MR-1 | 0 | 0 | 0 | 20 ± 5 | 0 | 106 ± 30 | 0 |
| TNP-KLH: secondary | 4 | MR-1 | 1 ± 1 | 0 | 0 | 36 ± 12 | 0 | 165 ± 19 | 0 |
| TNP-Ficoll: primary | 5 | MR-1 | 0 | 0 | 0 | 60 ± 18 | 0 | 222 ± 30 | 0 |

[a]Mice were immunized and sacrificed at the indicated day[b]. [c]Cryostat sections were prepared from spleens and immunohistochemical demonstration of gp39 was performed with an anti-gp39 mAb, or with CD40-Ig followed by secondary peroxidase-conjugates. Cells were counted in each anatomical compartment[d] of the spleen: Follicular corona, Fc; germinal center, GC; inner-PALS, iP; outer-PALS, oP; marginal zone, MZ; terminal arterioles, TA.
[e]Values represent mean ± SD number of positive cells in each compartment of spleen sections from three mice.

8.2.2. Localization and Kinetics of Gp39$^+$ Cells in Lymphoid Tissue

Gp39$^+$ Th cells were found predominantly in the outer-periarteriolar lymphocyte sheaths (PALS) and around the terminal arterioles (TA) of the spleen (Table 1, FIG. 9A; FIG. 10B). Double staining for CD4$^+$ and gp39 clearly revealed that CD4$^+$ cells in primary follicles were not gp39 positive (FIG. 9C). After secondary immunization, only a few gp39$^+$ cells were observed in the follicular corona, but not in the GC of secondary follicles (FIG. 9A). Examination of lymph node sections of TNP-KLH immunized mice revealed that gp39$^+$ cells were localized in the deep cortex and along the medulary cords (FIG. 9B). Incidently, gp39$^+$ cells were observed in the corona, but not in the GC, of follicles in lymph nodes.

At day 3 and 4 after injection of KLH we observed the maximum number of gp39$^+$ cells (FIGS. 11A–11B). Thereafter, the number decreased and remained stable during the next three days. Another group of mice was boosted 16 weeks later with KLH. Already during the first two days after secondary immunization we observed a striking increase of the number of gp39$^+$ cells, which was markedly higher as compared to the primary response. After four days, the gp39$^+$ cells reached maximum numbers, which were about two times higher as we observed during the primary immune response against KLH (FIGS. 11A–11B). Immunization with TNP-Ficoll, a TI type II antigen, resulted in an increase in the frequency of gp39$^+$ Th cells, attaining maximum frequencies 5 days after injection (FIG. 12). Similar as observed for TD antigens, in the antibody response against TNP-Ficoll gp39$^+$ cells were localized in the outer PALS and around the TA of the spleen (FIG. 10b). No gp39 expression was observed in the follicles of mice immunized with TNP-Ficoll.

8.2.3. Localization and Kinetics of Cytokine-producing Cells in the Spleen

Figure 9D:
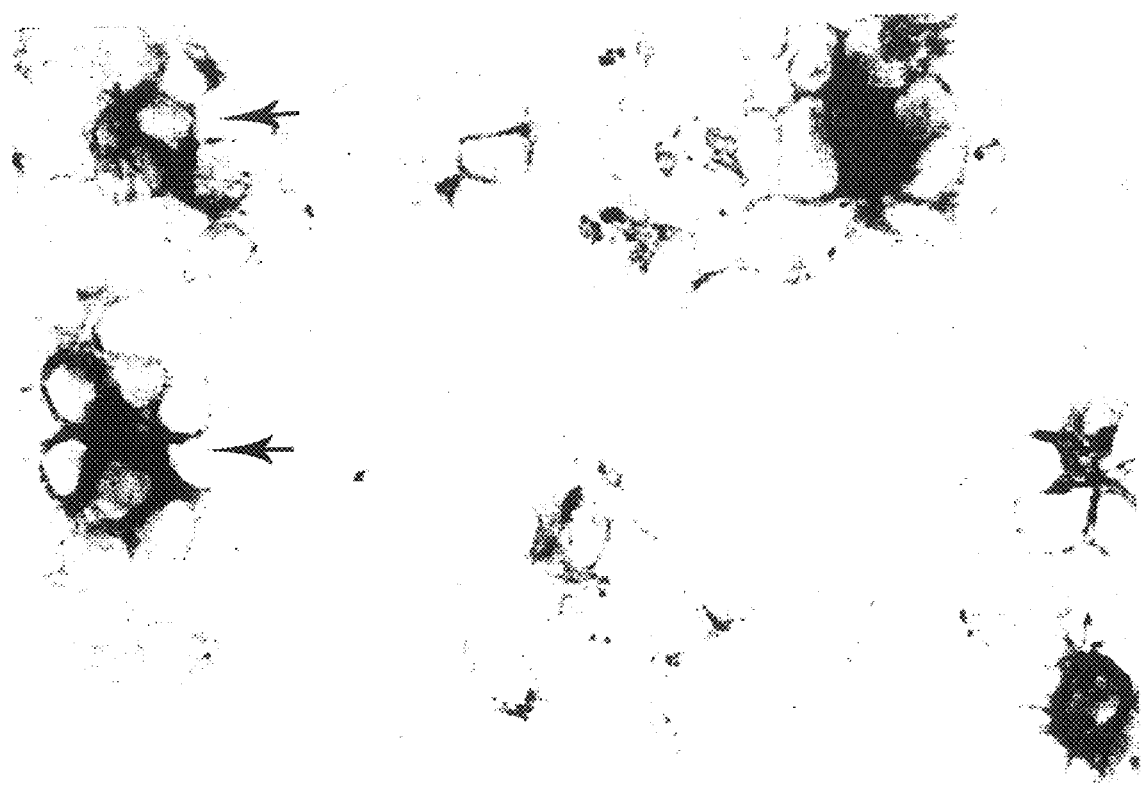

Th cell derived cytokines have a decisive role in isotype-selection (Snapper et al. (1987) Science 236:944), Snapper et al. (1988) *Immunol. Rev.* 102:51; Stevens et al. (1986) *Nature* 334:255). As antibody responses against TNP-KLH are dominated by IgG1 antibodies, we investigated whether a Th subset (Th1/Th2) was preferentially activated and where these cytokine-PC were localized in the spleen. Detection of cytokine-PC was performed with cytokine-specific mAb conjugated to different enzymes on splenic cryostat sections of TNP-KLH immunized mice. The IL-4-specific mAb (11B11) conjugated to β-gal was used for the in situ demonstration of IL-4-PC. After immunohistochemical revelation, IL-4-PC characterized by a turquoise cytoplasm were detected (FIG. 9d). No staining was observed in control slides from any specimen treated by omission or substitution of the primary antibody. Preincubation of 11B11 conjugated to β-gal with recombinant IL-4 inhibited the staining of IL-4-PC, in a dose-dependent manner. Moreover, the specificity of the staining was confirmed on cytospin preparations of cells from an IL-4-producing cell line (X6310-IL-4). IL-2-PC were demonstrated with an IL-2-specific mAb (S4B6) conjugated to HRP and were characterized by a red stained cytoplasm, respectively. Control immuno-conjugates showed no staining. Furthermore, the specific staining was inhibited by recombinant IL-2 in a dose dependent manner. In addition, specificity was confirmed on cytospin preparations of cells from an IL-2-producing cell line (X6310-IL-2). The specific demonstration of IFN-γ-PC, with an IFN-γ specific mAb (DB-1) conjugated to alkaline phosphatase, was performed as described in (Van den Eertwegh et al. (1991) *J. Immunol.* 147:439), Van den Eertwegh et al. (1991) *Lymphatic Tissues and In Vivo Immune Responses*, Imhof et al., Marcel Dekker, Inc., N.Y. 207:213). In all spleen sections examined, cytokine-PC were observed in the outer-PALS and around the terminal arterioles (TA) of the spleen. Cytokine-PC were never observed in the follicles or marginal zone of the spleen. Analysis of the kinetics of cytokine-PC revealed higher frequencies of IL-2-PC and IL-4-PC, relative to IFN-γ-PC, in the antibody response against TNP-KLH, reaching maximum frequencies at 3–4 days after immunization (FIG. 13A).

8.2.4. Cytokine-production by Gp39 Positive Cells

Gp39$^+$ cells are a prerequisite for B cell activation in vitro (Noelle et al. (1992) *Proc. Natl. Acad. Sci. USA* 89:6550) and TD antibody responses in vivo. Thereafter, cytokine-producing Th cells are thought to be active as regulators of antibody responses. In order to investigate whether gp39$^+$ cells have the capacity to produce cytokines, as was suggested by in vitro experiments (Hodgkin et al. (1991) *J. Immunol.* 147:3696), we performed double-staining experiments. MR-1 (gp39) was conjugated to AP, whereas S4B6 (IL-2) and 11B11 (IL-4) were conjugated to HRP and β-galactosidase, respectively. Double staining for IFN-γ and gp39 was performed with a direct IFN-γ-specific conjugate and MR-1 followed by a secondary HRP-conjugated mAb directed to hamster Ig. Double staining for IL-2 and gp39 revealed red stained cells producing IL-2, blue stained gp39$^+$ cells and violet double staining cells, representing gp39$^+$ cells producing IL-2. In the case of IL-4 and gp39, the turquoise stained cells were IL-4-producing cells, the red stained cells were gp39 positive, whereas double staining violet cells were gp39$^+$ cells producing IL-4 (FIG. 9D). After double staining for IFN-γ and gp39, we observed blue stained IFN-γ-PC, red stained gp39$^+$ cells and double staining violet cells, representing gp39+ cells producing IFN-γ. In the spleen, gp39$^+$ cells producing IL-2, IL-4 or IFN-γ were found both during TD as well as TI-2 antibody responses.

8.2.5. Kinetics and Localization of Antigen-specific AFC

Using KLH-HRP and TNP-AP conjugates, we were able to study the development of KLH-AFC and TNP-AFC in the spleen after immunization with KLH or TNP-KLH (Claassen et al. (1992) *J. Immunol. Methods* 150:207). As demonstrated in FIGS. 11A–11B and 12, in both experiments the kinetics of KLH-AFC or TNP-AFC developed according to similar patterns attaining maximum frequencies at 4 days after immunization. The frequency of TNP-(hapten)-specific AFC was about 10 times higher than the detected frequency of AFC specific for the carrier (KLH). After boosting with KLH we found about 8 to 10 times more KLH-AFC as compared to the primary immunization at the peak of the response (FIGS. 11A–11B). Immunization with TNP-Ficoll resulted in a gradual increase of the number of TNP-AFC attaining the maximum number at day 5 after immunization (FIG. 12).

8.2.6. Gp39$^+$ Positive Cells Co-localize With Antigen-specific B Cells

As gp39$^+$ Th cells have been found to be essential for the activation of B cells in vitro and in vivo, their anatomical localization in relation to resting and antibody-producing B cells was examined. Double immunohistochemical staining for resting B cells (membrane IgM-bearing) or B plasma blasts (cytoplasmic Ig) and gp39, revealed that the majority of gp39$^+$ Th cells were co-distributed amongst both B cell types in the outer PALS and TA. In addition, when antibody-forming B cells, specific for the immunizing antigen, were revealed, the majority of the KLH-AFC/TNP-AFC were found in intimate contact (juxtaposition) with the gp39$^+$ Th cells (FIG. 10A). Also in the immune response against TNP-Ficoll we observed antigen-specific B cells (TNP-AFC) co-localizing with gp39$^+$ cells in the outer-PALS and around the TA (FIG. 10B).

8.3. Discussion

The present study demonstrates that during in vivo antibody responses gp39 expression and cytokine-production develop simultaneously and are predominantly localized in the outer-PALS and around the TA of the spleen. The gp39$^+$ cells and cytokine-PC are found in juxtaposition to antigen-specific B cells. These results suggest that the initial Th cell induced B cell activation and the subsequent Th cell regulated B cell differentiation occur in restricted compartments of the spleen. The observed high frequency of IL-4-PC, relative to IFN-γ-PC, indicates that Th2-like cells are dominating in the antibody response against KLH.

In the primary antibody response against KLH, maximum frequencies of gp39$^+$ Th cells were observed 3–4 days after i.v. immunization (FIG. 11A). Later during the course of the immune response, reduced number of gp39$^+$ Th cells were present. Parallel studies using KLH-primed mice showed that upon secondary immunization with KLH, a significant increase in gp39$^+$ Th cells was observed within 24 hrs (FIG. 11B). Maximum frequencies in the secondary response were reached at day 4 and were about twice as high as those observed during primary responses. This observation is in agreement with the results described in the following section which show a twofold increase in helper activity after adoptive transfer of SRBC immunized spleen cells. Furthermore, the kinetics of appearance of gp39$^+$ Th cells and KLH-AFC were superimposable (FIGS. 11A–11B). In vitro studies using Th cell clones have demonstrated that gp39 is rapidly expressed upon triggering with anti-CD3 mAb (Noelle, et al. (1992) *Proc. Natl. Acad. Sci. USA* 89:6550). Data presented herein document that in vivo administration of antigen induces a rapid expression of gp39 on CD4+ Th cells. The simultaneous development of gp39+ cells and KLH-AFC, together with the demonstration of gp39+ Th cells juxtaposed to KLH-AFC, indicate that gp39 expression plays a role in the specific antibody production. This is substantiated by experiments described in the following section which show that anti-gp39 mAb were able to significantly reduce the antibody responses to KLH in vivo.

It is well known that rigorous T cell depletion completely abrogates the anti-TI-2 antibody response, indicating that T cells are necessary for a bona fide TI-2 response (Mond et al. (1980) *J. Immunol.* 125:1066; Mond et al. (1983) *J. Immunol.* 131:633; Endres et al. (1983) *J. Immunol.* 131:781). The observed high frequency of gp39+ Th cells after immunization with TNP-Ficoll was surprising, given the fact that the antibody responses to TNP-Ficoll were unaffected in vivo following administration of anti-gp39 mAb. This data confirms that the initiation of the antibody response against TNP-Ficoll was not dependent on gp39. TI-2 immune responses activated B cells appear to be responsible for the activation of T cells.

Analysis of the kinetics of cytokine-PC revealed that IL-2-PC and IL-4-PC were predominant in the antibody response against KLH with maximum frequencies at 3–4 days after immunization. The IFN-γ-PC were also found to be active in this immune response, reaching maximum levels at day 3, but the number of IFN-γ-PC was low as compared to the number of IL-2- and IL-4-PC. Bradley et al. (Bradley et al. (1991) *J. Exp. Med.* 174:547) observed that the kinetics of appearance of effector CD4+ T cells that produce cytokines upon restimulation with KLH in vitro were similar for each of the cytokines investigated. These results confirm our in vivo findings and suggest that after immunization and subsequent antigen presentation, T cells with potency to produce IL-2, and/or IL-4, IL-5 and/or IFN-γ are activated at about the same time and differentiate into cytokine-PC, following a similar time course. At the peak of the immune response, we observed relatively high frequencies of IL-2-PC and IL-4-PC in the outer-PALS and around the TA. As these cytokine-PC were observed in close conjunction, it is likely that these cells create a microenvironment which is rich in IL-2 and IL-4. Such a microenvironment has been suggested to be essential for the development IL-4-PC, as was demonstrated in vitro (Le Gros et al. (1990) *J. Exp. Med.* 172:921; Swain et al. (1990) *J. Immunol.* 145:3796; Swain et al. (1991) *Immunol. Rev.* 123:115). These experiments suggested that IL-2 was required for the optimum proliferation of cytokine-producing T cells (Le Gros et al. (1990) *J. Exp. Med.* 172:921; Swain et al. (1990) *J. Immunol.* 145:3796; Powers et al. (1988) *J. Immunol.* 140:3352), while IL-4 would propagate the preferential development of IL-4-PC (Le Gros et al. (1990) *J. Exp. Med.* 172:921; Swain et al. (1990) *J. Immunol.* 145:3796). After double staining we were able to detect TNP-AFC in close conjunction with cytokine-PC, indicating that these cytokines have a role in B cell differentiation. Nossal and Riedel (Nossal et al. (1989) *Proc. Natl. Acad. Sci. USA* 86:4679), demonstrated a rapid rise in precursors of KLH-binding IgG1-secreting B cells in the spleen 5 to 7 days after KLH immunization. IL-4 has been suggested to play a role to B cell switching to IgG1 and in the propagation of IgG1+ AFC (Stevens et al. (1986) *Nature* 334:255). Consequently, the observed juxtaposition of IL-4-PC to KLH-specific B cells may represent Th2-B cell interactions which stimulate the preferential development of IgG1+ cells. In this study we observed incidentally (<1%) gp39+ cells in the corona of the follicles, but no gp39+ cells or cytokine-producing T cells were found in the GC. These observations are compatible with studies in humans, (Bosseloir et al. (1991) New York, Marcel Dekker Inc. 315–319; Bowen et al. (1991) *Hum. Immunol.* 31:67, and mice, Van den Eertwegh et al. (1991) *J. Immunol.* 147:439; Van den Eertwegh et al. (1992) *Crit. Rev. Immunol.* 11:337), which demonstrated that none of the B cell differentiation factors, such as IL-2, IL-4 and IFN-γ, were localized in the follicles of lymphoid tissue.

During primary immune responses, antibody production in PALS and around TA precedes the germinal center formation, indicating that the initial B cell activation occurs outside the follicles (Liu et al. (1992) *Immunol. Today* 13:17; Kosco et al. (1992) *Immunol. Rev.* 126:63; Jacob et al. (1991) *J. Exp. Med.* 173:1165). This is in agreement with the results presented in this report, showing no gp39+ cells and cytokine-PC in the follicles, but in the outer-PALS and around the terminal arterioles. Only after secondary immunization, we observed a low frequency of gp39+ cells in the corona of lymphoid follicles. The similar localization of AFC (Claassen et al. (1992) *J. Immunol. Methods* 150:207), gp39+ cells and cytokine-PC as observed in the immune response against KLH or TNP-Ficoll, suggests that T-B cell interactions during primary and secondary antibody response against TD or TI-2 antigens occur in the same splenic compartments, e.g. the outer-PALS and terminal arterioles. Furthermore, it validates in vitro experiments demonstrating that the kinetics of cytokine production and CD40-ligand expression are superimposable (Hodgkin et al. (1990) *J. Immunol.* 145:2025). The observation that during the entire experimental period antigen-specific AFC and gp39+ cells were found in close conjunction, additional to in vitro experiments showing that extended contact (more than 48 hrs) is required for maximal proliferative responses (Kehry et al. (1990) *Res. Immunol.* 141:421), or cytokine production, Swoboda et al. (1991) *Eur. J. Immunol.* 21:1691, suggests that T-B conjugates may persist for several days in vivo.

FIG. 14 shows a model for the development of TD antibody responses in the spleen based on presented data and on the localization and migration of immune cells (Van den Eertwegh et al. (1992) *Crit. Rev. Immunol.* 11:337). According to this model, during the primary antibody response, TD antigens are presented by interdigitating cells in the PALS, leading to increasing numbers of antigen-specific T cells which subsequently encounter antigen-specific B cells in the PALS, forming T-B cell conjugates. During this cognate T-B cell interaction, CD4+ Th cells will be activated by antigen-presenting B cells and express CD40CR. Gp39 will trigger B cell growth and differentiation. Some of the activated B cells migrate to the follicles to undergo follicular processes, such as B cell selection, somatic mutation, affinity maturation and memory formation (Liu et al. (1992) *Immunol. Today* 13:17; Kosco et al. (1992) *Immunol. Rev.* 126:63). Other activated B cells migrate to the TA and differentiate into antigen-specific AFC regulated by activated cytokine-producing T cells. After secondary immunization, antigen-specific memory B cells acquire the antigen in the follicle, where it is presented by follicular dendritic cells in the form of immune complexes (Liu et al. (1992) *Immunol. Today* 13:17; Kosco et al. (1992) *Immunol. Rev.* 126:63). These B cells will migrate to the PALS and meet antigen-specific T cells and will subsequently follow the pathway as described for primary immune responses. In the case of secondary TD antibody responses, the follicles already contain relatively high frequencies of antigen-specific B cells, which increases the likelihood that B cells encounter antigen-specific T cells in the PALS. This may explain the relatively high frequency of activated gp39⁺ T cells and antigen-specific AFC found during secondary immune responses. The observation of higher frequencies of antigen-specific AFC relative to gp39⁺ T cells (FIG. 11), suggests that one T cell may be able to-activate more than one B cell. Alternatively, the relatively low frequencies of gp39⁺ T cells could be due to the shorter lasting expression of gp39 by T cells (Hodgkin et al. (1990) *J. Immunol.* 145:2025; Lederman et al. (1992) *J. Exp. Med.* 175:1091) as compared to the expression of antigen-specific antibodies of B cells.

In conclusion, this study demonstrates that gp39⁺ T cells and cytokine-PC are simultaneously upregulated in vivo after immunization. Furthermore, the observed high frequencies of gp39⁺ cells and IL-4-PC in close conjunction to antigen-specific B cells, may represent Th2-B cell interactions which propagate the preferential development of IgG1⁺ AFC in the antibody response against KLH. Finally, the data suggest that the initial cognate B cell activation and the subsequent regulation of B cell differentiation by T cells occur in the non-follicular areas of the spleen, namely the outer-periarteriolar sheaths and around the terminal arterioles.

9. EXAMPLE

Prolonged Suppression of the Humoral Immune Response by an Antibody to the Ligand for CD40. Gp39

This example shows that in vivo administration of anti-gp39 dramatically reduced both primary and secondary humoral immune responses to erythrocytes and soluble protein antigens without altering responses to the T-independent type II antigen (TI-typeII), TNP-Ficoll. Treatment of mice for 4 days with anti-gp39 inhibited the anti-sheep red blood cell (SRBC) response for at least three weeks and inhibited the expression of all Ig isotypes in secondary responses to the protein antigen, KLH. To examine the direct effect of anti-gp39 on $T_h$ function, SRBC-immune $T_h$ cells from anti-gp39-treated mice were adoptively transferred and shown fully capable of providing help. This suggested that anti-gp39 treatment did not cause $T_h$ deletion or anergy. In addition, proliferation of antigen-primed lymph node cells in vitro was not inhibited by anti-gp39. Anti-gp39 may mediate its profound immunosuppressive effects on humoral immunity by blocking gp39-CD40 interactions. Moreover, these studies establish gp39-CD40 as an important receptor-ligand pair for the targeting of therapeutic antibodies to control TD humoral responses.

9.1. Materials and Methods

9.1.1. Animals

Female, 6–8 week old BALB/C mice (Jackson Laboratories, Bar Harbor, Me.) were used for the in vivo experiments presented in this study. Animals were maintained in the specific pathogen-free animal facility at Dartmouth Medical School.

9.1.2. Helper T Cell Clones ($T_h1$)

D1.6, an I-A$^d$-restricted, rabbit Ig-specific $T_h1$ clone Kurt-Jones et al. (1987) *J Exp. Med.* 166:1774 was obtained from Dr. David Parker, University of Mass. at Worcester. Herein, D1.6 will be referred to as $T_h1$.

9.1.3. Reagents and Antibodies

MR1, hamster anti-murine gp39 mAb (14) was purified by DEAE HPLC from ascites fluid. Hamster Ig (HIg), used as a control antibody, was purified similarly from hamster serum (Accurate Chemical and Scientific Corp., Westbury, N.Y.). RG7/7.6.HL, a mouse anti-rat κ chain (strongly crossreactive with hamster κ chain) antibody, (RG7), (Springer et al. (1982) *Hybrid.* 1:257) was conjugated with HRPO or FITC and used as a secondary reagent to detect MR1 and HIg. Affinity-purified goat anti-mouse IgM, IgG$_1$, IgG$_{2a}$, IgG$_{2b}$ and IgG$_3$ (Southern Biotechnology, Birmingham, Ala.) were used as detection antibodies in the antigen specific ELISAs as well as in the total IgM and IgG1 ELISAs. B1E3, (kindly provided by Dr. T. Waldschmidt, Univ. of Iowa) a monoclonal anti-murine IgE, was used as the detection antibody for the IgE anti-KLH ELISA. Chimeric-L6 (Chi-L6), a humanized IgG$_1$ specific for the tumor antigen L6 (21), was kindly provided by Bristol-Myers Squibb Pharmaceutical Research Institute, Seattle Wash. Anti-CD4, GK 1.5 (Wilde et al. (1983) *J. Immunol.* 131:2178) was prepared by HPLC purification of ascites fluid. Sheep red blood cells (SRBC) were purchased from Colorado Serum Co. (Denver, Colo.). Sea Plaque agarose for use in anti-SRBC plaque assay was obtained from FMC Corporation (Rockland, Mass.). Baby rabbit complement was purchased from Cedarlane (Hornby, Ontario, Canada). KLH, Keyhole limpet hemocyanin, (from Megathura crenulita) was purchased from Calbiochem (La Jolla, Calif.). Complete Freund's adjuvant (CFA) for immunizations was obtained from Sigma Chemical Co. (St. Louis, Mo.). TNP-SRBC, TNP-KLH and TNP-BSA were prepared as previously described (Snow et al. (1987) *Immunol. Rev.* 99:173).

9.1.4. Immunizations for Generation of in vivo Primary and Secondary Antibody Responses For eliciting primary antibody responses to SRBC or TNP-SRBC, mice were immunized with 200 μl of 1% SRBC or TNP-SRBC suspension (i.v.). The IgM, anti-SRBC response was assayed 5 d after administration of antigen using a modification of the Jerne plaque assay (Jerne et al. (1974) *Transplant Rev.* 18:130). IgM anti-TNP responses were measured by ELISA on day 6. Primary responses to the heterologous immunogobulin Chi-L6 were generated by i.p. immunization of 100 μg Chi-L6, in alum, per mouse. The serum IgM anti-Chi-L6 antibody response was measured after 7 d. Primary responses to TNP-Ficoll were generated by immunization with 25 μg of TNP-Ficoll i.p. The IgM anti-TNP response was measured on day 6 by ELISA.

For generation of secondary humoral responses to KLH, animals were immunized with KLH in CFA (50 μg; i.p.). Mice were subsequently challenged with 10 μg of soluble KLH (i.p.) three months later. The anti-KLH antibody response was measured on d7 from the serum of immune mice utilizing isotype specific ELISAs. Secondary antibody responses to Chi-L6 were generated by challenging Chi-L6 immune mice with 10 μg soluble Chi-L6 i.p. The serum IgG, anti-Chi-L6 antibody response was measured after 7 d.

9.1.5. Anti-Gp39 Treatment

Sterile, HPLC-purified anti-gp39 (MR1) or HIg (as an antibody control) was administered (i.p.) on d0, d2, d4 post immunization or challenge as indicated for each experiment.

9.1.6. Antigen Specific ELISAs

The antigen specific IgM, IgG$_1$, IgG$_{2a}$, IgG$_{2b}$, IgG$_3$, and IgE antibody titers were determined using isotype specific ELISAs. Briefly, antigen, (1 mg/ml of KLH, Chi-L6, $TNP_{16}$-BSA, or $TNP_2$-BSA in PBS) was absorbed onto flexible polyvinyl microtiter dishes, overnight at 4° C. Plates were washed and blocked with PBS-1% FCS-azide. Diluted serum samples were incubated for 2 hours at 37° C. Samples were washed and the antigen specific antibody titers determined with one of the following alkaline-phosphatase conjugated detection antibodies: goat anti-mouse IgM, $IgG_1$, $IgG_{2a}$, $IgG_{2b}$, or $IgG_3$ (Southern Biotechnology, Birmingham, Ala.). The IgE specific ELISA was detected using biotin-conjugated B1E3 followed by alkaline phosphatase avidin (South San Francisco, Calif.). All ELISAs were developed by reaction of alkaline-phosphatase with phosphatase substrate (Sigma Chemical, Co., St. Louis, Mo.). Plates were analyzed on a Dynatech MR700 ELISA reader at 410 nm. Units represent arbitrary values based on the titration curve of a standard immune serum. All experimental groups were titered from 1:100 to 1:100,000 and the titer ascertained based on multiple point analysis. The levels of anti-KLH, anti-Chi-L6 and anti-TNP antibodies in unchallenged controls were below detection.

9.1.7. Detection of Serum Anti-Gp39

Serum from mice receiving 750 μg anti-gp39 (250 μg on d0, d2, d4) was obtained on d7, d14, and d21 after initiation of anti-gp39 treatment. The serum was run on a 7.5% SDS gel under non-reducing conditions, transferred to nitrocellulose, and blotted with HRPO-conjugated RG7. Following chemiluminescent detection, areas of the blot corresponding to 150–165 kDa were scanned and digitized using an Apple Scanner and the Image 4.1 software program.

Anti-CD3-activated $T_h1$, which express gp39, were stained with dilutions of serum from mice receiving 750 μg anti-gp39 (250 μg on d0, d2, d4) to determine the amount of biologically active gp39 remaining in the serum. Titrations of serum containing anti-gp39 were incubated with activated $T_h1$ cell clones for 30 minutes at 4° C., followed by washing and subsequent incubation with FITC-RG7, 30 minutes at 4° C. A standard curve of MFI vs anti-gp39 concentration was generated using purified anti-gp39. Samples were analyzed on a Becton Dickinson FACScan and the percent anti-gp39 remaining in the serum was deduced based on the anti-gp39 standard curve. The level of anti-gp39 present in the serum at d7 was set at 100%.

9.1.8. Generation and Proliferation of Antigen-primed Lymph Node Cells

Mice were immunized by footpad injection with 50 μl of KLH in CFA. Popliteal lymph nodes were removed on d5 after the administration of antigen and single cell suspensions were prepared. Lymph node cells were cultured in 200 μl complete RPMI at 100,000 cells per well in 96-well microtiter plates in the presence or absence of 100 μg/ml KLH. Anti-gp39 (MRI) was added to the cultures as indicated. Cellular proliferation was assessed using $^3$H-thymidine incorporation 3 d after initiation of culture.

9.1.9. Adoptive Transfer of Helper T Cells

Mice were immunized with SRBC (200 μl of 1% SRBC, i.v.) and administered anti-gp39 or HIg (250 μg on d0, d2, d4). On d7 the splenocytes were removed, erythrocyte depleted, washed and transferred (i.v., 50×10⁶/mouse) into irradiated recipients (600 rads) with or without 50×10⁶ spleen cells from TNP-KLH primed (TNP-KLHCFA, 50 μg i.p.) mice as a source of immune B cells. At the time of transfer, mice were immunized with TNP-SRBC (200 μl of 1% TNP-SRBC i.v.) Serum $IgG_1$ anti-TNP titers were ascertained on d6 post-transfer.

9.2. Results

9.2.1. Anti-gp39 Inhibits the Generation of Primary Antibody Responses to Erythrocyte Antigens The impaired TD immunity observed in patients with HIM, as well as the potent inhibitory effects of anti-gp39 and CD40-Ig on $T_h$-dependent B cell activation in vitro, provided the basis for the study of the potential immunosuppressive effects of anti-gp39 on humoral-mediated immunity in vivo. To investigate the role of gp39-CD40 interactions in primary TD humoral immune responses, the effect of in vivo administration of anti-gp39 on the primary antibody response to sheep red blood cells (SRBC) was determined. Animals were immunized with SRBC and administered anti-gp39 mAb (or control HIg) over the course of 4 d. On d5, the primary anti-SRBC antibody response of anti-gp39-treated, HIg-treated and control mice was ascertained. The IgM anti-SRBC plaque-forming cell (PFC) response of mice that received a total of 1.5 mg of anti-gp39 (500 μg/mouse on d0, d2 and d4) was reduced 99% when compared to the anti-SRBC PFC response from control or HIg-treated mice (FIG. 15A). In addition, administration of as little as 300 μg/mouse (100 μg/mouse on d0, d2, and d4) of anti-gp39 reduced the anti-SRBC primary immune response by 66%. Results from these experiments demonstrate that anti-gp39 treatment ablates primary antibody responses in vivo.

The duration of the immunosuppressive effects of anti-gp39 on the primary humoral immune response to SRBC was subsequently examined. Mice immunized with SRBC were treated with anti-gp39 for 4 d and assayed at various later time points for the capacity to mount a primary anti-SRBC response. In this set of experiments, all animals were immunized with SRBC on do and administered anti-gp39 or HIg on d0, d2, d4. The IgM anti-SRBC PFC response was measured for one group on d5. Additional SRBC-immune groups were challenged with SRBC on d7 or d14. Five days following each antigenic challenge (d12 and d19, respectively), the IgM anti-SRBC PFC response was measured. The results of one such experiment are depicted in FIG. 15B. As in FIG. 15A, the primary anti-SRBC responses were inhibited 80–90% 5 d after anti-gp39 administration was begun. In addition, the primary anti-SRBC responses 12 d and 19 d following anti-gp39 treatment were also inhibited >90%. These results demonstrate that even brief anti-gp39 treatment results in prolonged inhibition of primary antibody responses.

9.2.2. Anti-gP39 Inhibits the Generation of Secondary Anti-KLH Antibody Responses Using schedules of anti-gp39 administration that reduced the primary anti-SRBC PFC response, experiments were designed to evaluate the effects of anti-gp39 treatment on the secondary antibody responses. In these experiments, KLH-immune mice (immunized 3 months prior with CFA and KLH) were challenged with soluble KLH (10 μg/mouse/i.v.). On the day of antigen challenge (d0), mice were also given 250 μg of anti-gp39 or HIg, followed by anti-gp39 or HIg on d2 and d4. At d7 (FIG. 16B) and d14 (FIG. 16B) following challenge with KLH, the mice were bled and the titers of IgM, $IgG_1$, $IgG_{2a}$, $IgG_{2b}$, $IgG_3$ and IgE anti-KLH were determined. The results demonstrate several points: 1) challenge with soluble KLH induced an enduring secondary immune response that persisted for up to 14 d; 2) the administration of anti-gp39 significantly reduced the secondary anti-KLH response of the isotypes measured when compared to the administration of equal quantities of HIg; and 3) the immunosuppressive effects of anti-gp39 appeared to be sustained for at least 14 d after the initiation of anti-gp39 treatment. Taken together, results from these experiments demonstrate that similar to primary humoral immune responses, the generation of secondary humoral immune responses were also blocked by anti-gp39.

9.2.3. Anti-gP39 Inhibits the Generation of Antibody Responses to Heterologous IG Experiments depicted in FIGS. 15A and B demonstrate the immunosuppressive activity of anti-gp39 during a primary response to a strongly immunogenic particulate antigen, SRBC. The cellular nature of erythrocytes makes them unique in their capacity to elicit strong immune responses. Heterologous Ig molecules share this characteristic of being highly immunogenic, and therefore provide an additional model antigen system with which to examine the effects of anti-gp39 treatment on the generation of primary and secondary antibody responses. Animals were immunized with a heterologous Ig molecule, Chi-L6, a humanized mouse anti-tumor cell mAb, and treated with anti-gp39 or control HIg. After 7 d, sera was collected and assayed for the production of IgM anti-Chi-L6 antibodies In addition, mice were challenged with Chi-L6 14 d after initial immunization and anti-gp39 treatment, and assayed for IgG, anti-Chi-L6 antibody production on d21. FIGS. 17A–17B depicts the results of one such experiment. The primary antibody response to Chi-L6 in mice treated with anti-gp39 is inhibited by >90% when compared to HIg-treated mice. Moreover, the secondary, IgG, response to Chi-L6 is similarly inhibited. These results demonstrate that anti-gp39 treatment ablates primary and secondary antibody responses to a second type of TD antigen, heterologous Ig, as effectively as it suppresses responses to erythrocyte and soluble protein antigens.

9.2.4. Anti-gp39 Does Not Inhibit the Generation of Primary Antibody Responses to the T-independent Type II Antigens, TNP-Ficoll Although the above-described experiments demonstrate that anti-gp39 effectively blocks the generation of primary and secondary antibody responses to TD antigens in vivo it is unclear whether gp39-CD40 interactions play a role in the initiation of humoral responses to TI antigens. Data described herein demonstrate that immunization with the TI-type II antigen, TNP-Ficoll, results in gp39 expression by $T_h$ cells in vivo. In order to address whether gp39-CD40 interactions are necessary for the generation of antibody responses to this TI antigen, the effect of anti-gp39 treatment on mice immunized TNP-Ficoll, was assessed. Mice immunized with TNP-Ficoll or TNP-SRBC were treated with anti-gp39 or HIg and the IgM anti-TNP antibody response determined after 6 days. FIG. 18A and Panel A demonstrates that animals immunized with the TD antigen TNP-SRBC elicit significant anti-TNP serum antibody responses. As predicted from the previously described experiments, anti-gp39 treatment dramatically inhibits the primary anti-TNP response generated in these mice. In contrast, mice immunized with TNP-Ficoll mount a higher titered anti-TNP antibody response (FIG. 18B); however, treatment with anti-gp39 does not inhibit the antibody response to TNP-Ficoll. Results from these experiments demonstrate that, unlike responses to TD antigens, anti-gp39 does not block the generation of humoral responses to TNP-Ficoll, suggesting that responses to TI antigens may be gp39-independent.

9.2.5. Anti-gp39 Administration Does Not Functionally Delete SRBC-specific $T_h$ The preceding data indicates that anti-gp39 interferes with the development of TD humoral immunity. Immune suppression by anti-gp39 may be mediated by: 1) the negative signalling of gp39-bearing T cells causing $T_h$ anergy; 2) mAb-mediated cytotoxic deletion of anti-gp39 beating CD4+ T cells; and/or 3) the blocking of gp39 binding to CD40. A series of experiments were performed to gain insights into which of these mechanisms may be operative in the protracted immune suppression observed with anti-gp39 therapy. To explore the possibility that antigen-specific $T_h$ were deleted or energized by anti-gp39 therapy, antigen-specific $T_h$ function from gp39-treated mice was measured by adoptive transfer. Briefly, mice were immunized with SRBC (to prime SRBC-specific $T_h$) and administered anti-gp39 or HIg (250 µg/mouse on d0, d2, d4). After 7 d, SRBC-immune spleen cells from HIg-treated or anti-gp39-treated mice were adoptively transferred into recipient mice with TNP-immune spleen cells as a source of TNP-primed B cells. Mice were simultaneously challenged with TNP-SRBC, and the $IgG_1$ anti-TNP titer ascertained on d5. As shown in FIG. 19, SRBC helper activity from HIg-treated and anti-gp39-treated mice were similar, indicating that anti-gp39 treatment did not alter $T_h$ function or block the priming of $T_h$. Moreover, antigen-responsive $T_h$ were not deleted or energized as a result of anti-gp39 treatment, as they provided helper-effector function upon transfer.

9.2.6. Anti-gp39 Administration Does Not Block the Proliferation of Antigen-primed T Cells To gain further support of the tenet that anti-gp39 does not negatively signal $T_h$, the effect of anti-gp39 on antigen-induced Tb proliferative responses was determined. Briefly, mice were primed in the footpads with KLH in CFA (50 µg/footpad). After 5 d, the popliteal lymph nodes were removed and lymph node cells were cultured in vitro with antigen in the presence or absence of anti-gp39. The results demonstrate that the addition of anti-gp39 to cultures of KLH-primed lymph node cells does not block the antigen-induced proliferative response. In four separate experiments, the proliferative response of lymph node cells cultured with antigen alone was similar to that of cells cultured with antigen plus as much as 25 µg/ml of anti-gp39. In one representative experiment, in vivo primed lymph node cells cultured in vitro with 100 µg/ml KLH incorporated 87854±3522 cpm of $^3$H-thymidine, whereas cells cultured with antigen and 25 µg/ml of anti-gp39 incorporated 89084±1619 cpm. Cells cultured with no antigen yielded 2819±453 cpm. These data indicate that anti-gp39 does not functionally alter $T_h$ cells, at least in terms of their capacity to proliferate in response to antigen. Results from these experiments provide further evidence that anti-gp39 treatment does not negatively signal $T_h$.

9.2.7. In vivo Clearance of Hamster Anti-gp39

Assuming that the in vivo immunosuppressive effects of anti-gp39 are due to the blocking of gp39-CD40 interactions, long-term immune suppression observed with anti-gp39 administration requires the persistence of anti-gp39 in the host. To determine if anti-gp39 could be detected for the period of time that immune suppression was evident, the in vivo clearance rate of anti-gp39 from serum was determined. Mice were given a regimen of antibody (3×250 μg anti-gp39) over the course of 4 d and assayed for the levels of serum anti-gp39 at 7 d, 14 d, and 21 d after the initiation of antibody administration. Western blot analysis for non-reduced MR1 (160 kd) indicated that intact, serum anti-gp39 could be detected for at least 21 d after the initiation of antibody treatment (FIG. 20A). The serum concentration of anti-gp39 in animals at 21 d was approximately 5% (based on scanning densitometry), when compared to the signals derived from serum of animals analyzed 7 d after initiation of antibody therapy.

Although it was determined that intact anti-gp39 was present in serum, it was also important to ascertain that the anti-gp39 was biologically active. Therefore, sera from mice which received 3×250 μg of anti-gp39 over the course of 4 d were used to stain gp39-bearing $T_h$ (FIG. 20B). The level of serum anti-gp39 3 d after the last injection (7 d after initiation of antibody treatment) was set at 100%. Fourteen days after the initiation of antibody therapy, approximately 10–15% of the biologically active anti-gp39 mAb was detected in the serum. Twenty-one days post-initiation of therapy, 2–3% of anti-gp39 remained in the serum. Therefore, both the determination of intact gp39 by Western blotting and of biologically active anti-gp39 revealed that approximately 5% of the anti-gp39 was present 21 d after beginning anti-gp39 therapy. These results demonstrate the half-life of anti-gp39 to be approximately 12 d and offer evidence consistent with the hypothesis that prolonged suppression of humoral immune responses by anti-gp39 is due to persistent blocking of $T_h$ function.

9.3. Discussion

The present study demonstrates that an anti-gp39 antibody, which blocks gp39-CD40 interactions in vitro, results in profound inhibition of both primary and secondary humoral immune responses to TD antigens, but not TI-type II antigens. In addition, this study demonstrates that anti-gp39 treatment does not block the priming of, or proliferation of, antigen-primed $T_h$ cells. Therefore, the gp39-CD40 ligand-receptor pair can be used as a target for the therapeutic manipulation of the humoral immune response.

To gain insight into how anti-gp39 was exerting its immunosuppressive effect on humoral immunity, the direct effects of anti-gp39 on $T_h$ function were addressed. The data indicate that SRBC-immune $T_h$ from anti-gp39-treated mice were fully capable of providing help upon adoptive transfer. In addition, anti-gp39 did not reduce the in vitro T cell proliferative response to antigen. Taken together, these data suggest that anti-gp39 treatment did not cause $T_h$ deletion or anergy in vivo, or impose a negative signal to antigen-induced T cell proliferation in vitro. These results led to the speculation that anti-gp39 mediates its immunosuppressive effects by blocking gp39 binding to CD40 and not by the inactivation of gp39-bearing $T_h$. In support of this hypothesis in vitro studies here established that anti-gp39 blocks the binding of CD40 to gp39. Furthermore, biologically active anti-gp39 could be detected in serum for the period of time that immune suppression was apparent. Although only 5% of anti-gp39 was present in serum at a time when immune suppression was evident, it is possible that the local tissue concentrations of anti-gp39 in specific sites of secondary lymphoid organs is higher and clearance rates are slower than that of serum anti-gp39.

Treatment of mice with anti-gp39 inhibited the primary immune response to SRBC and heterologous Ig>90% for prolonged periods of time. Assuming that anti-gp39 is mediating the inhibition by blocking gp39 function, these data implicate gp39-CD40 interactions as essential in the development of primary immune responses to TD antigens. Immunohistochemical analysis establish that gp39 is induced as a consequence of immunization with TD antigens and may be of functional significance. The in situ studies of gp39 expression illustrate that the initial site of gp39-CD40 interactions during primary humoral immune responses is in the peripheral aspects of the periarteriolar lymphoid sheaths (PALS) and around the terminal arterioles (TA) of the spleen. It is at these sites that conjugates between gp39-expressing $T_h$ and antigen-specific B cells were found juxtaposed, suggesting that the outer PALS is a major site of T cell-B cell interactions during primary humoral immune responses. Therefore, the PALS may be the site at which anti-gp39 interacts with gp39-expressing $T_h$ cells to ultimately inhibit T-B interaction and subsequent Ig production.

Similar to primary responses, the secondary humoral immune response of mice primed to KLH in CFA was also shown to be inhibited by the administration of anti-gp39. Consistent with the reduction of anti-SRBC PFC by anti-gp39, reductions in serum antibodies titers to antigenic challenge were also observed. The serum titers of all anti-KLH Ig isotypes measured (IgM, $IgG_1$, $IgG_{2a}$, $IgG_{2b}$, $IgG_3$, and IgE) were reduced by the treatment of mice with anti-gp39. The effect of anti-gp39 administration was apparent for at least 14 d after secondary challenge with antigen, establishing a persistent immune suppression by anti-gp39. Anti-gp39-mediated immune suppression of secondary responses to KLH is not unique to KLH, since secondary immune responses to heterologous Ig and heterologous erythrocytes were also inhibited by anti-gp39 therapy. The anatomical distribution of gp39-expressing $T_h$ was identical to that observed upon primary immunization, however, the frequency of gp39-expressing $T_h$ in immune spleen was increased over that observed during primary immune responses. No gp39-expressing $T_h$ were found in the germinal centers or follicles of immune spleen. Thus, it appears that B cells are triggered to respond to activated $T_h$ cells in the PALS and TA of the spleen and later migrate to the follicles and germinal centers.

The focus of the present study was to demonstrate the potential use of anti-gp39 in the control of TD humoral immunity. Brief treatment regimes with anti-gp39 resulted in prolonged suppression, an attractive attribute of this therapeutic antibody. Of special interest may be the capacity of anti-gp39 to prevent primary and secondary humoral responses to other heterologous, therapeutic antibodies such as Chi-L6. This would permit the exposure of patients to repeated adminstrations of heterologous therapeutic antibodies. Inhibitory effects on humoral immunity have been observed with other mAbs, i.e. anti-CD4 E (Carteron et al. (1990) *Clin. Immunol. Pathol.* 56:373; Horneff et al. (1991) *Arthritis and rheumatism* 34:129). Although it is unclear how anti-CD4 mediates immune suppression, extensive deletion of CD4+ T cells is correlated with suppressive efficacy (Shizuru et al. (1992) *Immunol. Rev.* 129:103), a phenomenon not observed with anti-gp39 therapy. In addition to anti-CD4, it has been shown that the interference by CTLA-4 of CD28 triggering, a co-stimulatory molecule on $T_h$ cells, also suppresses TD antibody responses (Linsley et al. (1992) *Science* 257:792) and blocks xenogeneic graft rejection (Lenschow et al. (1992) *Science* 257:789). Similar to anti-gp39 administration, CTLA-4 induced a state of prolonged immune suppression. Because anti-gp39 and CTLA-4 mediate their immunosuppressive effects at distinct stages of the humoral immune response, co-administration of these two immunosuppressive drugs may provide additive or synergistic immunosuppressive effects on immunity.

10. EXAMPLE

Analysis of the Signal Transduction Pathways Triggered by Activated Helper T Cell in Resting B Cells In this example, the signal transduction pathway initiated in B cells as a consequence of interacting with activated $T_h$ is examined. Unlike anti-mIg or anti-MHC class II, plasma membranes isolated from activated $T_h$, $PM^{Act}$, did not trigger an increase in the B cell intracellular concentrations of cAMP or calcium. In addition, $PM^{Act}$ did not stimulate PKC activation as measured by MARCKS phosphorylation and PKC translocation. $PM^{Act}$, however, induced the tyrosine phosphorylation of several B cell substrates, including a 43 kd protein which comigrated with ERK 1. Neutralizing antibodies directed against gp39 blocked $PM^{Act}$-induced B cell PTK activity; conversely, agonistic antibodies directed against CD40 stimulated B cell PTK activity. Since triggering through CD40 appear essential for $T_h$-dependent B cell activation, these results suggest that CD40 initiates a signal transduction pathway in B cells which is different from the pathway initiated by mIg or MHC class II.

10.1. Materials and Methods

10.1.1. Animals

Female DBA/2j mice (Jackson Laboratories, Bar Harbor, Me.) at 6–8 weeks of age were used for the preparation of filler cells to support the growth of $T_h$ clones of plasma membrane isolation and in the preparation of resting B lymphocytes.

10.1.2. Helper T Cell Clone ($T_h$)

Membrane fractions from resting and activated D1.6, an I-A$^d$ restricted, rabbit IgG-specific $T_h1$ clone (Kurt-Jones et al. (1988) *J. Immunol.* 140:3773), were used.

10.1.3. Activation of $T_h$ by Anti-CD3

$T_h1$ were cultured at $8 \times 10^6$ cells/well in cluster wells (6 well, Corning Glass Works, Corning N.Y.) coated with 10 μg/ml of anti-CD3 in PBS (Leo et al. (1987) *Proc. Natl. Acad. Sci. USA* 84:1374). Cells were incubated for 16 hours at 37° C., harvested, and washed.

10.1.4. Preparation of $T_h$ Plasma Membranes

Plasma membranes were prepared by discontinuous sucrose gradient sedimentation, as described previously (Noelle et al. (1991) *J. Immunol.* 146:1118).

10.1.5. Preparation of Murine Resting B Lymphocytes

B cells were prepared from the spleens of 6–8 week old DBA/2J mice (Jackson Laboratories), as described in (Noelle et al. (1991) *J. Immunol.* 146:1118).

10.1.6. IL4 Pretreatment of Resting B Lymphocytes

Resting B cells at $5 \times 10^6$/ml were incubated with mouse rIL4 (10 ng/ml; kindly provided by Drs. C. Maliszewski and K. Grabstein, Immunex Corporation, Seattle, Wash.), in RPMI containing 10% FCS (Hyclone, Logan, Utah), for 16 hours at 37° C.

10.1.7. Antibodies

The following antibodies were purified by ion exchange HPLC from ascites grown in mice which had been irradiated and bone marrow reconstituted: anti-CD3: 145-2C11 (Leo et al. (1987) *Proc. Natl. Acad. Sci. USA* 84:1374); anti-CD4: RL172/4 (Mizouchi et al. (1989) *J. Immunol.* 142:270) and GK1.5 (Armitage et al. (1992) *Nature* 357:80); anti-MHC class II: M5/114.15.2 (Bhattacharya et al. (1981) *J. Immunol* 127:2488); anti-gp39 (MR1) (Noelle et al. (1992) *Immunol. Tod.* 13:431); and anti-TcR ($\alpha/\beta$): H57-597 (Kubo et al. (1989) *J. Immunol.* 142:2736).

10.1.8. Reagents

The following reagents were utilized: forskolin (Sigma Chemical Co.) and Bapta-AM (Molecular Probes Inc., Eugene, Oreg.).

10.1.9. Preparation of Human B Lymphocytes

E$^-$ rosetted B cells were isolated from blood samples obtained from normal donors. Sheep red blood cells (RBCs; Kroy Medical Inc., Stillwater, Minn.) were incubated in AET (2-aminoethyl isothiouronium bromide, 140 mM, pH 9.0; Sigma Chemical Co.) for 15 minutes at 37° C. and washed. Peripheral blood lymphocytes (PBLs) were separated from whole blood by flotation on Ficoll gradients and rotation to remove monocytes. PBLs were then mixed with AET-treated sheep RBCs, at a ratio of 1 PBL:30 sheep RBCs, for 15 minutes at 37° C. Cells were pelleted, set on ice for 2 hours, and separated by flotation on a Ficoll gradient. The interface, containing E$^-$ B cells and sheep RBCs, was harvested and washed. The contaminating sheep RBCs were lysed by treatment with Tris-buffered ammonium chloride.

10.1.10. Measurement of B Cell RNA Synthesis

B cell cultures, in 96-well flat bottomed plates (Costar, Cambridge, Mass.), were pulsed with $^3$H-Uridine (5 μCi/well; NEN, Dupont Co., Boston, Mass.) at 8 hours post-culture. Cells were incubated for an additional 2 hours, harvested, and processed for liquid scintillation spectroscopy.

10.1.11. Measurement of Intracellular cAMP Concentration

Murine resting B cells at $10^6$ cells/sample were incubated with $PM^{rest}$ (1 ng–10 μg/sample), $PM^{Act}$ (1 ng–10 μg/sample), anti-MHC class II (50 μg/ml) or forskolin (50 μM; Sigma Chemical Co.) in RPMI containing 10% FCS (Hyclone) and rolipram (0.1 mM; Diagnostic Products Corp.) for various time points and volumes. The reaction was stopped with the addition of cold TCA (2 mM) and samples were analyzed with a $^3$H-cAMP Assay Kit, (Diagnostic Products Corp.). Briefly, samples were ether-extracted 3 times, dried, and resuspended in Tris-EDTA. $^3$H-cAMP and a cAMP-binding protein were added to each sample and all samples were set on ice for 90 minutes. Charcoal-dextran was added to each sample to absorb free $^3$H-cAMP. Samples were centrifuged and the resulting supernatants were prepared for liquid scintillation spectroscopy.

10.1.12. Measurement of Intracellular Calcium Concentration

Murine resting B cells at $10^7$ cells/ml were loaded with Indo-1 (5 μM; Molecular Probes Inc.), in RPMI containing 10% FCS (Hyclone), for 30 minutes at 37° C. Cells were washed, aliquoted at $10^6$/sample, and maintained at 37° C. Indo-1 fluorescence was measured on an Ortho Systems 50H Cytofluorograph (Ortho Pharmaceutical, Raritan, N.J.). During analysis, the following activators were added: $PM^{rest}$ (1 ng–10 µg/sample), $PM^{Act}$ (1 ng–10 µg/sample), ionomycin (5 µM; Molecular Probes Inc.), and GαM IgG F(ab')$_2$ (50 µg/ml; Cappel, Organon Teknika, Corp.); PM samples were incubated at various volumes. In each experiment, cells were gated by forward versus side scatter to eliminate dead cells; approximately $7.5 \times 10^5$ cells were analyzed per sample, collecting over a 45 minute period. The fluorescence intensity ratio of 404 nm/485 nm was calculated for each cell and calibrated against intracellular calcium concentration, as previously described (Rabinovitch et al. (1986) *J. Immunol.* 137:952).

10.1.13. Detection of MARCKS Phosphorylation

Murine resting B cells at $10^7$ cells/ml were labeled with $^{32}$P-orthophosphate (0.5 mCi/ml; New England Nuclear, Dupont Co.) for 1 hour at 37° C. in phosphate-free DMEM containing 10% FCS (Hyclone). Cells were washed, aliquoted at $5 \times 10^5$ cells/sample, and incubated with the following activators, in phosphate-free DMEM containing 10% FCS (Hyclone) for various time points and volumes: $PM^{rest}$ (1 ng–10 µg/sample), $PM^{Act}$ (1 ng–10 µg/sample), PMA (100 ng/ml; Sigma Chemical Co.), and GαM IgG F(ab')2 (50 µg/ml; Cappel, Organon Teknika, Corp.). Cells were lysed in Extraction Buffer (10 mM Tris, pH 7.4, 0.15 mM NaCl, 0.02% NaN$_3$, 0.5% NP-40, and 100 µg/ml each of aprotinin, leupeptin, pepstatin A (Sigma Chemical Co.)) and immunoprecipitated for 16 hours at 4° C. with an anti-MARCKS polyclonal antiserum followed by Protein A Sepharose for 1 hour at 4° C. (Sigma Chemical Co.). The anti-MARCKS polyclonal antiserum was generated through the use of a MARCKS peptide, kindly provided by Dr. P. Hornbeck, University of Maryland, Baltimore, Md. Samples were washed three times with Extraction Buffer, electrophoresed on a 7.5% SDS/Page gel (Laemmili (1970) *Nature* 227:680), transferred to 0.2 µm nitrocellulose (Schleicher & Schuell, Keene, N.H.), and prepared for autoradiography.

10.1.14. Detection of Protein Kinase C Translocation

Murine resting B cells at $5 \times 10^5$ cells/sample were incubated with $pM^{rest}$ (1 ng–10 µg/sample), $PM^{Act}$ (1 ng–10 µg/sample), PMA (100 ng/ml; Sigma Chemical Co.) or GαM IgG F(ab')2 (50 µg/ml; Cappel, Organon Teknika, Corp.) in RPMI, containing 10% FCS (Hyclone), for various time points at 37° C. and volumes. Cells were washed in PBS and digitonin permeabilized according to Berry et al. (Berry et al. (1989) *J. Immunol.* 143:1407). Briefly, cells were resuspended in Translocation Buffer (20 mM MOPS (Sigma Chemical Co.) pH 7.2, 10 mM EGTA (Sigma Chemical Co.), 5 mM EDTA (Fisher Chemical Co., Fair Lawn, N.J.), 0.5 mg/ml digitonin (Wako Chemicals USA, Inc.), 100 µg/ml each of pepstatin A, leupeptin, and aprotinin (Sigma Chemical Co.)) set on ice for 5 minutes and spun at 300 rpm for 2 minutes. The supernatant (cytosolic fraction) and the remaining pellet (membrane fraction) for each sample were analyzed via SDS/Page electrophoresis and Western blotting; samples were electrophoresed on a 7.5% SDS/Page gel and transferred to 0.2 µm nitrocellulose (Schleicher & Schuell). The blot was probed with an anti-PKC polyclonal antiserum (Kraft et al. (1988), *J. Biol. Chem.* 264:8437), kindly provided by Dr. C. Ashendel, Purdue University, Purdue, Ind., followed by GαCh IG-HPRO (Southern Biotechnology Inc.) and developed with the ECL Western Detection Blotting System (Amersham Co., Arlington Heights, Ill.).

10.1.15. Detection of Phosphotryosine Proteins

B cells at $5 \times 10^5$ cells/100 µl were warmed in 96-well plates (Costar) with RPMI containing 10% FCS (Hyclone) for 30 minutes at 4° C. or 37° C. The following activators were added to the B cell cultures and incubated for various time points at 4° C. or 37° C.: $PM^{rest}$ (1 ng–10 µg/10 µl), $PM^{Act}$ (1 ng–10 µg/100 µl), GαM IgG F(ab')2 (50 µg/ml; Cappel, Organon Teknika, Corp.), anti-CD40 (1 µg/ml; G28.5; kindly provided by Dr. J. Ledbetter, Bristol-Meyers Squibb, Seattle, Wash.) (Clark et al. (1988) *Eur. J. Immunol.* 18:451), mouse IgG$_1$ (1 µg/ml; Southern Biotechnology Inc.), PMA (100 ng/ml; Sigma Chemical Co.), or ionomycin (75 ng/ml; Molecular Probes Inc.). Cells were harvested and washed in PBS—5% FCS (Hyclone). Cells were lysed in Phosphotyrosine Detection Buffer (Extraction Buffer containing 1 mM vanadate (Sigma Chemical Co.)) then prepared for SDS/Page electrophoresis and Western blotting. Briefly, samples were electrophoresed on a 10% SDS/Page gel and transferred to 0.45 µm PVDF Immobilon (Millipore, Bedford, Mass.). The blot was probed with the anti-phosphotyrosine antibody 4G10 (Davis et al. (1991), *Science* 252:712), kindly provided by Dr. R. Frackelton, Brown University, Providence R.I., followed by GαM IgG$_{2b}$-HPRO (Southern Biotechnology Inc.) and then developed with the ECL Western Detection Blotting System (Amersham Co.).

10.1.16. Detection of ERK Proteins

Murine resting B cells at $5 \times 10^5$ cells/sample were lysed in Extraction Buffer, prepared for SDS/Page electrophoresis and Western blotting as described above. Blots were then probed with anti-ERK polyclonal antiserum #691 (Boulton et al. (1991) *Cell. Regulat.* 2:357), kindly provided by Dr. M. Cobb, Southwestern Medical Center, Dallas, Tex., followed by GαRb IgG-HPRO (Southern Biotechnology Inc.) and developed with ECL Western Detection Blotting System (Amersham Co.). To probe phosphotyrosine blots for ERK proteins, phosphotyrosine blots were stripped of all detecting antibodies by incubating blots in 0.2M glycine and 0.05% Tween 20 (Sigma Chemical Co.), pH 2.5, for 2 hours at 80° C. Blots were then probed with anti-ERK polyclonal antiserum #691, as described above.

10.2. Results

10.2.1. Measurement of $T_h$ Dependent B Cell RNA Synthesis

Since $PM^{Act}$ drive B cells into the cell cycle as measured by increased B cell RNA synthesis (Noelle et al. (1991) *J. Immunol.* 146:1118), a measurement of B cell RNA synthesis was included in each experiment described below as a control for B cell cycle entry. B cells were cultured with $PM^{rest}$, $PM^{Act}$, or anti-mIg for 8 hours, which is the time closest to $T_h$-B interaction when an increase in B cell RNA synthesis was reproducibly detected over backgound, pulsed with $^3$H-uridine and then processed for liquid spectroscopy. As antibody-mediated crosslinking of mIg triggers B cell cycle entry and proliferation, anti-mIg was included as a mitogenic control (Defranco et al. (1982) *J. Exp. Med.* 155:1523). At 8 hours post-culture, both anti-mIg and $PM^{Act}$ stimulated a 3-fold increase in B cell RNA synthesis, as compared to B cells alone or B cells cultured with $PM^{rest}$ (FIG. 21A). At 24 hours, much larger differences in levels of RNA synthesis in PM$^{Act}$-stimulated B cells vs PM$^{rest}$-stimulated B cells were observed (FIG. 21B). In addition, both anti-mIg and PM$^{Act}$ (10 μg/sample) stimulated an equivalent percentage (80%) of B cells, as analyzed by increased MHC class II and ICAM1 expression, respectively. Taken together, these results indicate that the indexes of activated $T_h$ and anti-mIg stimulation were equivalent. Therefore, it was hypothesized that if $T_h$ and anti-mIg triggered a similar signalling pathway, then they would also stimulate equivalent magnitudes of the same second messenger events.

10.2.2. Detection of Intracellular cAMP Production

Cambier et al. have shown that ligation of Ia on quiescent B cells increases the production of intracellular cAMP (Cambier et al. (1987) *Nature* 327:629). To determine if PM$^{Act}$ also induced an increase in the B cell intracellular cAMP concentration, B cells were incubated with either PM$^{rest}$, PM$^{Act}$, forskolin or anti-MHC class II for various time points. Samples were processed immediately and the cAMP$_i$ was measured through the cAMP-specific radio immunoassay, as described in Materials and Methods. Forskolin and anti-MHC class II were included as positive controls. At 15 minutes post-stimulation, forskolin induced a 20-fold increase in cAMP$_i$, 3.0×10$^4$ fmol cAMP/10$^6$ B cells, and anti-MHC class II induced a 4-fold increase, 6.0×10$^3$ fmol cAMP/10$^6$ B cells; B cells alone or cultured with PM$^{rest}$ averaged 1.5×10$^3$ fmol cAMP/10$^6$ B cells (FIG. 22). However, at this time point, PM$^{Act}$ induced only a 1.2-fold increase in cAMP$_i$, 1.8×10$^3$ fmol cAMP/10$^6$ B cells (FIG. 22). Similar experiments were performed to determine if increased concentrations of PM and/or shorter or longer incubation periods induced alterations in cAMP$_i$. As noted in Table II, higher concentrations of PM, as well as alterations in the time of sampling still did not reveal alterations in B cell cAMP$_i$. Previous studies revealed that B cells pretreated with IL-4 enhanced the proliferative response of B cells to PM$^{Act}$ (Noelle et al. (1991) *J. Immunol.* 146:1118]. Therefore, the cAMP$_i$ response of IL4-pretreated B cells was tested. IL4, in combination with PM$^{Act}$, which increases the percentage of B cells responsive to PM$^{Act}$ from 13.3% to 43.8% (Noelle et al. (1991) *J. Immunol.* 146:1118] did not cause increased cAMP$_i$.

TABLE II

Description of experimental parameters altered during analysis of Th-dependent B cell activation

| Experiment[a] | PM/sample[b] | Kinetics[c] | IL4 Pretreatment[d] |
|---|---|---|---|
| [cAMP]$_i$ | 0.1 μg, 1 μg, 2.5 μg, 5 μg, 10 μg | 0', 2.5', 5', 10', 15', 20', 30', 45', 60' | yes |
| [Ca$^{2+}$]$_i$ | ↓ | ↓ | yes |
| MARCKS Phosphorylation | | 5', 15', 30', 45', 60', 90', 2 hrs, 4 hrs | yes |
| PKS Translocation | | ↓ | yes |

[a]-described in text
[b]-amount of PM$^{rest}$ or PM$^{Act}$ utilized per sample, at each time point listed.
[c]-time points of T$_h$-B incubation
[d]-B cells were treated with or without IL4, as described in Methods and Materials, prior to T$_h$-B culture at the various PM/sample and time points listed

10.2.3. Analysis of Intracellular Calcium Mobilization

Recent studies report that ligation of either MHC class II molecules on B cells, primed by exposure of IL4 and antigen receptor binding, or mIg initiates calcium mobilization through the phospholipase C (PLC)/protein kinase C (PKC) signalling pathway (Ransom et al. (1986) *J. Immunol.* 137:708; Cambier et al. (1991) *J. Immunol.* 146:2075). To determine if $T_h$-B contact drives calcium mobilization, B cells were loaded with Indo-1, a calcium-sensitive dye (Grynkiewicz et al. (1985) *J. Biol. Chem.* 260:3440), and then incubated with PM$^{rest}$, PM$^{Act}$, anti-mIg or ionomycin, a calcium ionophore (Liu et al. (1978) *J. Biol. Chem.* 253:5892) for various time points. Changes in Indo-1 fluorescence were monitored via flow cytometry as described in Materials and Methods. Ionomycin and anti-mIg were included as positive controls increasing Ca$^{2+}$$_i$ to 1.3×10$^3$ nM and 490 nM, respectively; B cells alone or cultured with PM$^{rest}$ averaged 80 nM calcium (FIG. 23). Although PM$^{Act}$ induced approximately a 2-fold increase in B cell Ca$^{2+}$$_i$ over time, from 75 nM at 0 minutes to 140 nM at 20 minutes post-incubation, this increase was not significantly different as compared to PM$^{rest}$ (FIG. 23). Additional experiments were performed with various PM$^{Act}$ concentrations, incubation times and IL4 pretreated B cells (Table II). Despite these manipulations, PM$^{Act}$ did not induce significant increases in the B cell Ca$^{2+}$$_i$.

10.2.4. Measurement of MARCKS Phosphorylation

A number of studies demonstrated that in addition to stimulating increased cAMP$_i$ and Ca$^{2+}$$_i$, engagement of mIg or MHC class II molecules activated the serine/threonine kinase PKC (Chen et al. (1986) *J. Immunol.* 136:2300; Cambier et al. (1987) *Nature* 327:629). To examine PKC activity during $T_h$-dependent B cell activation, the phosphorylation of the myristoylated-alanine-rich-C-kinase-substrate (MARCKS), an endogenous PKC substrate (Graff et al. (1991) *Science* 246:503) was monitored. B cells were labeled with $^{32}$porthophosphate and incubated with PM$^{rest}$, PM$^{Act}$ or phorbol myristate acetate (PMA). Samples were immunoprecipitated with an anti-MARCKS polyclonal antiserum (Hornbeck et al. (1989) *Molec. Cell. Biol.* 9:3727) and prepared for electrophoresis and autoradiography as described in Materials and Methods. The MARCKS protein has a molecular weight of approximately 80 kd. PMA, which directly activates PKC (Schmidt et al. (1975) *Cancer Res.* 35:1375), was included as a positive control inducing a significant increase in the phosphorylation of the MARCKS protein at 30 minutes post-stimulation; B cells alone exhibited a basal level of MARCKS phosphorylation (FIG. 24). PM$^{Act}$, however, induced little or no increase in MARCKS phosphorylation at 1, 2 or 4 hours post-stimulation as compared to PM$^{rest}$ (FIG. 24). Additional experiments were performed with various PM$^{Act}$ concentrations, incubation times and IL4 pretreated B cells (Table II). Despite these manipulations, PM$^{Act}$ did not induce significant increases in the phosphorylation of the B cell MARCKS protein.

10.2.5. Analysis of Protein Kinase C Translocation

As a second indicator of PKC activation, the translocation of PKC from the cytoplasm to the membrane compartment was monitored in B cells stimulated with PM$^{Act}$. B cells were incubated with PM$^{rest}$, PM$^{Act}$, PMA, or anti-mIg and permeabilized. Permeabilization facilitated the isolation of cytosolic and membrane fractions which were then analyzed for PKC content with an anti-PKC polyclonal antibody (Kraft et al. (1988) *J. Biol. Chem.* 263:8437). As such, inactive PKC was detected in the cytoplasmic fraction while active PKC was detected in the membrane fraction. FIG. 25 illustrates the results of the B cell membrane fractions only.

PMA and anti-mIg, included as positive controls, induced significant increases in PKC translocation to the B cell membrane at 5 minutes post-culture; at this time point, B cells alone exhibited a basal level of PKC translocation (FIG. 25). Unlike PMA, anti-mIg induced the translocation of two PKC isoforms at approximately 80 kd and 78 kd (FIG. 25). However, PM$^{Act}$ did not induce a detectable increase in PKC translocation at 30 minutes post-culture as compared to PM$^{rest}$ (FIG. 25). Analysis of cytosolic fractions revealed a concomitant loss of PKC in response to PMA or anti-mIg, but not to PM$^{rest}$ or PM$^{Act}$. Additional experiments were performed with various PM$^{Act}$ concentrations, incubation times and IL4 pretreated B cells (Table II). Despite these manipulations, PM$^{Act}$ did not induce detectable increases in PKC translocation to the B cell membrane.

Taken together, these data demonstrate that calcium mobilization and PKC activation are not increased during $T_h$-dependent B cell activation. In addition, these findings suggest that, unlike anti-mIg, $T_h$-mediated B cell responses are triggered via a pathway independent of PKC activation.

10.2.6. Detection of Phosphotyrosine Proteins Induced by PM$^{Act}$

Antibody-mediated cross-linking of mIg (Gold et al. (1990) *Nature* 345:810; Campbell et al. (1990) *EMBO J.* 9:2125) or MHC class II molecules on B cells triggers a PTK pathway (Lane et al. (1990) *J. Immunol.* 144:3684), implicating tyrosine phosphorylation in the initiation of B cell growth. To examine PTK activity during $T_h$-dependent B cell activation, B cells were incubated with PM$^{rest}$, PM$^{Act}$ or anti-mIg for various time points. Cell lysates were then prepared for electrophoresis and Western blotting with the anti-phosphotyrosine monoclonal antibody 4G10 (Davis et al. (1991) *Science* 252:712) as described in Materials and Methods. Lysates from anti-mIg stimulated cells were included as positive controls; at present, there are no specific reagents against murine CD40. Both anti-mIg and PM$^{Act}$ induced an increase in the tyrosine phosphorylation of several proteins, including 95 kd, 50 kd, 43 kd, 39 kd, and 33 kd proteins (FIGS. 26A–26B). PM$^{Act}$ stimulated phosphorylation of these proteins was transient with peak phosphorylation at 1 hour post-culture. Additional experiments were performed with IL4 pretreated B cells; however, IL4 pretreatment had no effect on the phosphotyrosine profile induced by PM$^{Act}$.

10.2.7. Determination of Tyrosine Phosphorylation as an Active Event

The increased number and intensity of phosphotyrosine proteins shown in FIGS. 26A–26B is most likely the result of PM$^{Act}$ stimulating B cell PTK activity. However, it is possible that these proteins are passively acquired by the B cell as a result of binding PM$^{Act}$ which contain an array of phosphoproteins. To eliminate this possibility, a number of studies were performed. First, if the phosphoproteins were constitutively expressed by PM$^{Act}$, passive acquisition of the phosphoproteins should be observed at both 4° C. and 37° C. As such, B cells were incubated with either PM$^{rest}$ or PM$^{Act}$ at 4° C. or 37° C. and prepared for phosphotyrosine analysis, as described previously. PM$^{Act}$ enhanced the tyrosine phosphorylation of several proteins, in a concentration dependent manner, at 37° C. but not at 4° C. (FIG. 27A). Although there may appear to be some differences in the PM$^{Act}$-induced phosphotyrosine profile, as compared to FIG. 26B, the phosphotyrosine profile in FIG. 27A was underexposed in order to demonstrate clearly the concentration dependence of the PM$^{Act}$ effect. These results suggest that tyrosine phosphorylation was not a passive binding event of PM$^{Act}$, but rather an active event in the B cell. In order to verify that PM$^{Act}$ bound to B cells at 4° C., B cells were cultured with PM$^{Act}$ at both 4° C. and 37° C. and then analyzed for cell cycle entry, as measured by increased RNA synthesis. As shown in FIG. 28, the binding of PM$^{Act}$ was not inhibited at 4° C., since B cells incubated with PM$^{Act}$ at either temperature were able to enter the cell cycle (FIG. 28).

Although it was unlikely that B cells passively acquired phosphotyrosine proteins from PM$^{Act}$, it was possible that the altered phosphotyrosine profiles, in the presence of PM$^{Act}$, were due to increased PTK activity in the PM vesicles bound to B cells. To determine whether or not the PM$^{Act}$ were metabolically competent to phosphorylate tyrosine-containing PM proteins, the following experiment was performed. Intact $T_h$, PM$^{rest}$ and PM$^{Act}$ were incubated with PMA, which activates PTK in T cells (Nel et al. (1990) *J. Immunol.* 145:971), and samples were prepared for phosphotyrosine analysis, as described previously. It is likely that only a small percentage of the input PM$^{Act}$ bind to B cells and could contribute to the anti-pTyr profiles observed. A maximal amount of PM$^{Act}$ (10 µg) was analyzed to see if PTK activity in the PM$^{Act}$ could contribute to the profiles. PMA-treated $T_h$, as a positive control (FIG. 29A), induced the tyrosine phosphorylation of several proteins; however, no phosphotyrosine proteins were detected in PMA-treated or untreated PM$^{Act}$ (FIG. 29B). These findings strongly suggest that the binding of PM$^{Act}$ to B cells stimulates PTK activity resulting in an increase in the number and intensity of B cell phosphotyrosine proteins. These findings further suggest that tyrosine phosphorylation was not an active event in PM$^{Act}$ and, therefore, that the phosphotyrosine proteins detected above were associated with the B cell.

10.2.8. Anti-gp39 Inhibits PM$^{Act}$-Induced Tyrosine Phosphorylation

Several studies support CD40 as a trigger molecule for a tyrosine kinase pathway in B cells: CD40 is homologous to the low affinity nerve growth factor receptor (p75$^{NGFR}$) (Stamenkovic et al. (1989) The *EMBO J* 8:1403), which together with the trkA gene product (p140$^{trkA}$), initiates a protein tyrosine kinase (PTK) pathway (Miyasaka et al. (1991) *Proc. Natl. Acad. Sci. USA* 88:2653); and antibody-mediated cross-linking of CD40 induces the tyrosine phosphorylation of several B cell substrates (Uckun et al. (1991) *J. Biol. Chem.* 266:17478). To determine if gp39-CD40 interaction was essential for enhanced PTK activity, B cells were incubated with either PM$^{rest}$ or PM$^{Act}$ in the presence and absence of anti-gp39 or an anti-TcR monoclonal antibody, included as a negative control. Although the blot was overexposed in order to show the effect of anti-gp39, it does demonstrate the PM$^{Act}$ stimulated the tyrosine phosphorylation of several B cell substrates (FIG. 30), including a 93 kd, 43 kd and a 33 kd protein. However, the PM$^{Act}$ enhanced tyrosine phosphorylation of these B cell substrates, especially the 43 kd protein, was blocked in the presence of anti-gp39, but not anti-TcR. These results support the tenet the gp39-CD40 interaction is necessary for PM$^{Act}$ induction of PTK activity.

10.2.9. Detection of Human B Cell Phosphotyrosine Proteins Induced by Anti-CD40

Human B cells were utilized to identify CD40 as the trigger molecule for the enhanced tyrosine kinase activity.

Human B cells were incubated with anti-CD40 (Clark et al. (1986) *Proc. Natl. Acad. Sci.* 83:4494), mIgG, or PMA plus ionomycin, for various time points and prepared for phosphotyrosine analysis as described previously. PMA plus ionomycin, which induces the tyrosine phosphorylation of B cell substrates (Uckun et al. (1991) *J. Biol. Chem.* 266:17478), was included as a positive control; mIgG was included as a negative control for anti-CD40. Both PMA plus ionomycin and anti-CD40 induced the tyrosine phosphorylation of a 43 kd phosphoprotein, while mIgG had no effect (FIG. 31A). The blot in FIG. 31A, was overexposed in order to show the specific phosphorylation of the 43 kd protein, characterized as ERK I in the following section. Phosphorylation was transient, peaking at 5 minutes post-culture for both PMA plus ionomycin and anti-CD40.

10.2.10. Characterization of the 43 kd Phosphotyrosine Protein

Since Casillas et al. reported that anti-mIg triggered the phosphorylation of an ERK protein (Casillas et al. (1991) *J. Biol. Chem.* 266:19088), studies were designed to characterize the 43 kd phosphotyrosine protein, phosphorylated in response to gp39-CD40 interaction, as ERK I. B cells were incubated with either $PM^{rest}$ or $PM^{Act}$ and prepared for phosphotyrosine analysis as described above. In addition, unstimulated B cells were analyzed in parallel and probed with the anti-ERK polyclonal antiserum #691 which detects both ERK I (43 kd) and ERK II (41 kd) (Boulton et al. (1991) *Cell. Regulat.* 2:357). As shown in FIGS. 27A–27B, the 43 kd phosphotyrosine protein, enhanced by $PM^{Act}$, comigrated with ERK I (FIG. 27B). In addition, the human B cell 43 kd phosphotyrosine protein detected above comigrated with ERK I (FIG. 31B); neither ERK I nor ERK II were detected in PMA-treated or untreated $PM^{Act}$ (FIG. 29b). Although these results suggest that the B cell 43 kd substrate is ERK I, studies in which ERK I is immunoprecipitated and then analyzed for phosphotyrosine content are in progress to confirm this observation.

Taken together, these data demonstrate that PTK activation is increased during $T_h$-dependent B cell activation. Further, this increase in PTK activity appears to phosphorylate a 43 kd protein which comigrates with ERK I.

10.3. Discussion

The data presented herein demonstrate that, during $T_h$-dependent B cell activation, $T_h$ trigger a tyrosine kinase-dependent signalling pathway in B cells. Specifically, activated $T_h$ enhanced the tyrosine phosphorylation of several proteins, including a 43 kd protein which comigrated with ERK I, in the absence of increased calcium mobilization and protein kinase C (PKC) activation. The increased tyrosine phosphorylation of these proteins was an active event in the B cell, and not in activated $T_h$, demonstrating that these proteins were B cell substrates. In addition, an anti-gp39 monoclonal antibody, which inhibited $T_h$-dependent B cell activation, blocked increased tyrosine phosphorylation suggesting that gp39-CD40 interactions triggered signal transduction between $T_h$ and B cells. CD40 was further implicated as a trigger molecule since an agonistic anti-CD40 monoclonal antibody enhanced tyrosine phosphorylation of several human B cell substrates, including a 43 kd protein.

Pollock et al. have reported that activated Th cells induce a transient increase in the intracellular concentration of cAMP in B cells (Pollok et al. (1991) *J. Immunol.* 146:1633), in contrast with those results presented herein. Recently, it was determined that, unlike $PM^{Act}$, fixed, activated $T_h$ release low levels of lymphokines following fixation. This observation suggests that the activated $T_h$-mediated increase in B cell $cAMP_i$ may be due to the effect of contaminating lymphokines in culture. Alternatively, activated $T_h$ may cross-link MHC class II molecules more effectively than $PM^{Act}$, since activated $T_h$ have a larger surface area. Consequently, activated $T_h$, but not $PM^{Act}$ would trigger an increase in B cell $cAMP_i$. However, because $PM^{Act}$ induce B cell cycle entry, and not an increase in cAMP, these results suggest that an increase in $cAMP_i$ is not essential for $T_h$-dependent B cell activation.

Antibody mediated cross-linking of either mIg or MHC class II has facilitated the study of second messenger events initiated during B cell activation. These studies have shown that cross-linking of mIg or MHC class II triggers increased intracellular cAMP, production, PTK activity, phosphoinositol turnover, intracellular calcium mobilization and PKC activation. Additionally, Lane et al. have reported increased phosphoinositol turnover and intracellular calcium concentration in a human B lymphoblastoid cell line which present peptide to an antigen-specific T cell clone (Lane et al. (1991) *J. Immunol.* 147:4103). In contrast, our data indicate that during $T_h$-dependent B cell activation activated $T_h$ trigger PTK stimulation through CD40 on interacting B cells in the absence of increased intracellular cAMP production, intracellular calcium mobilization or PKC activation. Our findings are supported by Gruber et al. who have demonstrated that B cells stimulated through CD40 or mIg differed in their sensitivity to anti-CD45, suggesting that pathway utilized by CD40 was different from that utilized by mIg (Gruber et al. (1989) *J. Immunol.* 142:4144). Further, Chartash et al. observed that $T_h$ did not stimulate increased phosphoinositol turnover and intracellular calcium concentration in normal human B cells which had been pulsed with antigen (Chartash et al. (1988) *J. Immunol.* 140:1974). Although there are differences in the B cell populations examined (e.g. human B lymphoblast vs. murine resting B cell) as well as differences in the methods of analysis, these findings support the tenet that CD40 initiates a signal transduction pathway in B cells during the Th-dependent B cell activation which is different from the pathway initiated by mIg or MHC class II.

B cells are activated by both thymus-independent (TI) or thymus-dependent (TD) antigens. Although both of these antigenic types initiate B cell proliferation and antibody production, they do so through different triggering systems. TI antigens deliver mitogenic signals via mIg; whereas, TD antigens ultimately trigger B cell activation via CD40. It appears, based on the data presented in this section, that the biochemical signalling pathways employed to initiate B cell activation by TI and TD antigens are quite divergent, and that unlike TI antigens, TD antigens, with T cell help, trigger signal transduction through CD40, initiating PTK activity in the absence of increased intracellular cAMP production, intracellular calcium mobilization and PKC activation.

11. EXAMPLE

Inhibition of Primary and Secondary Immune Response, Induced by CHI-L6, by Treatment with an ANTI-gp39 Antibody

11.1. Materials and Methods

11.1.1. Animals

DBA/2j mice were used and obtained from NCI laboratories (Bethesda, Md.).

11.1.2. Alum Precipitation of Antigen

For the primary immunizations Chi-L6 was precipitated on alum (aluminum potassium sulfate, Sigma, St. Louis, Mo.) by adding 10% alum solution to 1 mg/ml Chi-L6 to a ratio of 1:1(v:v). The pH was then adjusted to 6.5 with NaOH and then the reaction mixture was allowed to stand for 30 minutes at room temperature. The mixture was then washed twice with PBS (pH 7.4) and then resuspended at 1 mg/ml of antigen.

11.1.3. Immunization Protocol

Three groups of mice, with 3 in each group, were immunized with 100 µg i.p. of Chi-L6 on alum. One group then received 250 mg injections i.p. of the anti-gp39 antibody, MR1, one days 0, 2, 4, and 6. The second group received the same injection regime but using an irrelevant hamster control antibody (HIg) and the third group received no antibody treatment. All animals were bled before the primary immunization and then bled after 1 week. Serum samples were then prepared to analyze for the presence of anti-chi-L6 antibodies (IgM) in the primary immune response. After this period mice were injected with 100 µg of soluble chi-L6 i.p. and no further antibody treatment was given. These mice were then left for 2 weeks, when they were again bled and the serum samples prepared for detection of IgG antibodies to chi-L6, indicative of a secondary immune response.

11.1.4. ANTI-CHI-L6 Specific ELISA

An ELISA was developed to detect the presence of anti-Chi-L6 antibodies in the serum of the mice. The wells of a 96 well polyvinyl microtitre plate were coated with Chi-L6 at a concentration of 10 µg/ml (100 µl), and incubated overnight at 4° C. The plate was then washed 3 times and 100 µl of PBS containing 5% FCS and 0.02% azide was added to each well as the blocking step and incubated for 60 minutes at 37° C. The plate was again washed 3 times and the serum samples were then added at various dilutions. The test serum and standard serum were incubated for 2 hours at 37° C. and then removed by washing the plate 3 times. The appropriate alkaline phosphatase conjugate antibody (goat anti-mouse $IgG_1$ or IgM, (1:500 dilution), Southern Biotechnology Inc. Birmingham, Ala.) was added to each well and after 2 hours of a 37° C. incubation the conjugated antibody was removed by thorough washing. The phosphatase substrate (1 mg/ml, Sigma, St. Louis, Mo.) was then added for approximately 15 minutes or until the appropriate color change occurred. Readings were determined by an ELISA reader (Dynatech Laboratories, Inc.) at an absorbance of 410 nm. Concentrations of Ig were determined by comparison to the appropriate positive serum (Chi-L6 immunized animal serum) standard curve and expressed as the mean antibody units±standard error (n=3).

11.2. Results

FIG. 32 indicates that the treatment of immunized animals with anti-gp39 antibody does in fact inhibit the primary IgM response to Chi-L6. The profound induction of anti-chi-L6 antibodies is markedly reduced by the MR1 treatment. When animals are then challenged with the soluble form of Chi-L6 but receive no further antibody treatment, it is found that the IgG response, indicative of a secondary immune response, is also inhibited.

It was originally thought that a relevant control for these experiments would be equivalent treatment of GVHD-induced mice with hamster Ig(HIg) (i.p. 250 µg) but it was observed that an 8 fold increase was detected in the level of Ig produced by 1 week HIg treated GVHD-induced mice compared to untreated 1 week GVHD-induced mice. Also increased spleen cell counts were obtained in the HIg treated GVHD-induced mice compared to untreated GVHD-induced mice. Consequently it was decided to designate the untreated $F_1$ recipient mice as the control.

Reversal of the splenomegaly inhibition of hyper Ig production in GVH-induced mice by anti-gp 39 administration, indicates that anti-gp39 blocked the ability of the grafted T cells to induce host B cell activation (FIG. 33). This inhibition persists for 7 days even when the treatment is terminated. These results indicate that T cell function has been affected either by clonal deletion of the reactive T cells or that T cell anergy has occurred. Alternatively, inhibitory levels of anti-gp39 remain during this 7 day interval resulting in the blockade of Th effector function. This data suggests that anti-gp39 interferes with the ability of T cells to elicit a strong GVHD clinical immunopathology and splenomegaly.

12. EXAMPLE

Antibody Targeting to GP39, the Ligand for Murine CD40, Prevents the Development of Collagen Induced Arthritis The role of gp39-CD40 interactions in the development of autoimmune disease has been investigated in vivo using an antibody that blocks gp39-CD40 interactions. Arthritis induced in mice by immunization with type II collagen (CII) was completely inhibited by the administration of anti-gp39. Administration of anti-gp39 to CII-immunized mice blocked the development of joint inflammation, serum antibody titers to collagen, the infiltration of inflammatory cells into the subsynovial tissue and erosion of cartilage and bone. These results indicate that blocking the gp39-CD40 interactions may have significant therapeutic potential in the treatment of autoimmune disease.

Experimental evidence has established that the CD40 ligand, gp39, is essential in the development of thymus-dependent immunity, (Noelle et al. (1992) *Immunol. Tod.* 13:431) The expression of gp39 is largely restricted to activated $CD4^+$ T cells (Lane et al. (1990) *J. Immunol.* 144:3684; Spriggs et al. (1992) *J. Exp. Med.* 176:1543; Lederman et al. (1992) *J. Exp. Med.* 175:1091) and its receptor, CD40, is a mitogenic receptor expressed on mature B cells. It has been postulated that expression of gp39 during cognate T-B cell interactions is an essential signal in the development of thymus dependent immunity. This postulate has been proven with the recognition that X-linked hyper IgM syndrome (HIM), a condition that results in the severe reduction in thymus dependent responses and immunoglobulin (Ig) isotype switching, is due to point mutations in the gp39 gene (Korthauer et al. (1993) *Nature* 361:539; DiSanto et al. (1993) *Nature* 361:541; Allen et al. (1993) *Science* 259:990; Noelle et al. (1992) *Proc. Natl. Acad. Sci. USA* 89:6550). Mutant gp39 proteins from HIM patients cannot trigger B cell activation and are unable to bind to CD40 (Korthauer et al. (1993) *Nature* 361:539). Although thymus dependent (TD) humoral immune responses in HIM patients are impaired, cell-mediated immune responses are intact, suggesting that gp39 is only essential in antibody-mediated immunity. A monoclonal antibody (mAb) specific to murine gp39, MR1, blocks the binding of gp39 to CD40 and also blocks T helper cell (Th)-dependent B cell activation in vitro. Experiments were designed to evaluate the ability of a mAb specific to gp39 to control the course of humoral immune responses in normal and disease states. Administration of anti-gp39 interferes with the development of primary and secondary humoral immune responses, apparently by blocking the binding of gp39 to CD40.

The effects of anti-gp39 administration on a murine model of human autoimmune disease, rheumatoid arthritis, is presented herein to determine the role of gp39-CD40 interactions in the development of autoimmune disease. Collagen type II-induced arthritis (CIA) is induced in susceptible strains of mice by intradermal injections of heterologous native type II collagen (CII) (Cathcart et al. (1986) Lab. Invest. 54:26). Since the transfer of antibodies to CII to naive animals leads to a condition histopathologically different from CIA and results in only transient synovitis (Seki et al. (1992) Journal of Immunology 148:3093–9), the role of humoral immunity in the development of CIA is not completely understood. In contrast, the transfer of both antibodies to CII and CD4+T cells from mice immunized with denatured CII, completely reconstitutes classical arthritis (Linsley et al. (1992) Science 257:792–5). Therefore, synergy between the cellular and humoral arms of the immune response appears to be essential in the development of arthritis.

The kinetics of disease progression that results from the immunization of DBA/1J (H-28) mice with CII is depicted in FIGS. 34A–34B. Mice were immunized with chick CII in Complete Freunds Adjuvant (CFA), then challenged three weeks later with soluble CII. After challenge with soluble CII, a dramatic rise in rate of disease progression, was noted. To quantitate the course of disease progression, mice were assigned scores depending on the severity of the inflammation of the fore and hind limbs. In the experiment depicted in FIG. 34, three groups of mice (eight mice per group) were immunized with CII in CFA and then one week later each group received either no mAb, anti-gp39, or irrelevant hamster Ig (HIg). Mice were subsequently administered antibody (250 µg per mouse) every four days until the end of the experiment. This antibody treatment regime was used because previous titrations established that this regime of mAb administration inhibited greater that 90% of the primary (IgM) anti-SRBC response (Courtenay et al. (1980) Nature 283:665). Antibody half life is estimated to be 12 days and thus injections every four days maintains adequate levels for the blocking of gp39 function. Since the secondary boost of CII is primarily involved in the induction of arthritogenic antibody, anti-gp39 was administered prior to the secondary boost so as to interfere with the development of clinical disease. The HIg-treated mice developed CIA at a more aggressive rate than the control animals, but by 40 days post-primary immunization 75–80% of the HIg and control animals had developed CIA (FIG. 34A). Anti-gp39 therapy prevented all mice in this group from presenting with any signs of clinical disease. The mean arthritis index (MAI) was used as a means of measuring disease severity. This index reflects the extent of clinical disease per animal and the percentage of animals in each group with disease (FIG. 34B). A high percentage of the untreated and HIg-treated mice presented with extensive distal joint inflammation. None of the anti-gp39-treated mice showed any signs of such inflammation.

Another consequence of immunization with CII is a precipitous rise in serum IgG titers to CII. In CII-immunized mice treated with anti-gp39, the serum IgG anti-CII titers were inhibited compared to the anti-CII titers found in mice untreated or treated with HIg (FIG. 35). In fact, titers of anti-CII in anti-gp39-treated mice were similar to titers found in nonimmune control sera (Cooper et al. (1992) Clin. Exp. Immunol. 89:244–250). Furthermore, during the course of the experiments (40–60 days), the administration of anti-gp39 did not alter the levels of total serum IgM or IgG$_1$, as one might have anticipated from the HIM studies (Trentham et al. (1977) J. Exp. Med. 146:857–868). In addition, at this time, we have not been able to detect antibodies against the anti-gp39 mAb in treated mice (Courtenay et al. (1980) Nature 283:665). Finally, CII-immunized mice that have been treated with anti-gp39 for 40 days and then not given additional anti-gp39 have not developed clinical signs of CIA at 70 days post-initial immunization. Therefore, anti-gp39 does not have to be continuously given to prevent disease onset (Cremer et al. (1992) J. Immunol. 149:1045–1058).

Histologically, joints from all of the untreated and HIg-treated mice were severely damaged by the rapidly expanding synovial pannus. Mononuclear cell infiltration, thickening of synovial membrane, and bone erosion by osteoclasts were apparent as well as exudate and polymorphonuclear cell accumulation in the synovial space. In marked contrast, there were no signs of inflammatory processes in four of five joints examined from anti-gp39-treated mice. In one joint from an anti-gp39 treated mouse, only rare polymorphonuclear leukocytes were present. Thus, the lack of clinical arthritis in these mice was not simply the result of a low level of inflammation but rather a complete lack of initiation of synovial inflammation.

13. EXAMPLE

Role of CD40-GP39 Interactions in Chronic Graft-Versus-Host Disease

Increased polyclonal immunoglobulin (Ig) production has been associated with the induction of chronic GVHD. This is thought to be due to T-B cell cognate interactions. It has been proposed that CD40, on antigen-presenting B cells, interacts with its ligand, gp39, on activated T helper cells, and it is this recognition that elicits thymus-dependant (TD) humoral immune responses. A murine model for GVHD was used to test the hypothesis that CD40-gp39 interactions are responsible for the hyperproduction of immunoglobulin (Ig). The effect of in vivo administration of anti-gp39 antibody on GVHD-induced polyclonal B cell activation was ascertained. GVHD-induced polyclonal IgG$_1$ and IgA production was completely reversed by anti-gp39 antibody administration. Furthermore, in the mice with GVHD, there was a marked increased in the spleen size that was reversed by the administration of anti-gp39. Both spleen size and reduced Ig levels remained normal for extended time periods when the antibody treatment was terminated.

This data suggests that the CD40-gp39 interactions, between the donor T cells and the recipient B cells, are responsible for increased Ig levels and splenomegaly observed in GVHD.

13.1. Materials and Methods

13.1.1. Mice

DBA/2 (H-2$^d$) and B6D2F$_1$ ((C57BL/6 (H-2$^d$)×DBA/2)F$_1$ hybrid) mice were obtained from the NCI laboratories (Bethesda, Md.). All the mice used in this study were female.

13.1.2. Induction of Chronic GVHD

Chronic GVHD was induced by the i.v. injection of parental (DBA/2) spleen cells into non-irradiated (C57BL/6×DBA/2) F$_1$ hybrid recipients (Fast (1990) J. Immunol. 144:4177). Parental mice were anesthetized and killed by cervical dislocation in preparation for removal of the spleen. Dissociated spleen cells were washed and resuspended in RPMI 1640 medium (Whittaker, Walkersville, Md.) for i.v. injection into the F$_1$ recipients.

13.1.3. Antibodies

MR1 was produced in our laboratory as previously described (Noelle et al. (1992) Proc. Natl. Acad. Sci. USA 89:6550). All anti-IgG$_1$ and IgA antibodies and standard controls were obtained from Southern Biotechnology Associates, Inc., (Birmingham, Ala.).

13.1.4. Antibody Treatment

Mice with ongoing GVHD were treated with MR1 following the regime indicated in FIG. 36.

13.1.5. Assessment of GVHD

GVHD induction was determined by splenomegaly and hyperproduction of Ig in vitro. Spleens were removed from treated or untreated mice with ongoing GVHD. Cells suspensions were treated with Tris-buffered ammonium chloride and total white blood cell counts were determined by visual hemocytometer counting. Cells were incubated ($5 \times 10^6$) in 1 ml of RPMI-1640 medium (supplemented with 10% fetal calf serum, 25 mM HEPES, 2 mM L-glutamine, 5000 U/ml penicillin and 5000 µg/ml streptomycin) for 3 days at 37° C., 5% $CO_2$. Cell supernatants were collected by pelleting the cells and Ig was quantified by an isotype-specific ELISA assay. The ELISA was performed by absorbing goat anti-mouse IgG$_1$ or IgA (10 µg/ml; Southern Biotechnology Associates, Inc., Birmingham, Ala.) in PBS onto wells of a 96-well polyvinyl microtitre plate for 1 hour at 37° C. then overnight at 4° C. Plates were washed and blocked with PBS containing 1% FCS for 1 hour at 37° C. Plates were washed again and the appropriate dilutions of supernatants and standard controls (IgG$_1$ and IgA, Southern Biotechnology Associates, Inc., Birmingham, Ala.) were added for 2 hours at 37° C. After this time, the plates were washed 3 times and alkaline-phosphatase conjugated goat anti-mouse IgG$_1$ or IgA (1:500 dilutions) (Southern Biotechnology Associates, Inc., Birmingham, Ala.) were added for 2 hours at 37° C. Plates were thoroughly washed and phosphatase substrate (1 mg/ml; Sigma Diagnostics, St. Louis, Mo.) added resulting in the appropriate color change. Readings were determined by an ELISA reader (Dynatech Laboratories, Inc.) at an absorbance of 410 nm. Concentrations of Ig were determined by comparison to the appropriate isotype standard curve and expressed as the mean±standard error (n=3).

13.2. Results and Discussion

13.2.1. GVHD in Mice Results in Splenomegaly

In the mouse, one of the classical consequences of GVH reaction is the enlargement of the spleen. It is primarily the host's own cells that infiltrate and enlarge the spleen, although this is in response to the presence of the graft cells. It was observed, upon removal of the spleens from GVHD-induced mice, that GVHD resulted in splenomegaly. FIGS. 38A–38B indicates that mice induced with GVHD for 1 week and 2 weeks resulted in spleens with almost twice the cell numbers compared to normal F$_1$ recipients. When mice were treated with the anti-gp39 antibody (250 µg/mouse, days 0,2,4, and 6), the cell numbers returned to levels of the normal spleens and remained low for 1 week after the antibody treatment was terminated (2 wk GVHD+1 wk MR1 (FIG. 37)).

13.2.2. GVHD-induced Hyperproduction of Polyclonal Immunoglobulin

It has been reported that hyperproduction of Ig occurs in mice with chronic GVHD. This increased level of Ig production is due to T-B-cognate interactions (Morris et al. (1990) *J. Exp. Med.* 171:503) between the donor T cells and the recipient B cells. The donor B cells are irrelevant and do not participate in this syndrome (Morris et al. (1990) *J. Immunol.* 3:916).

To determine whether the anti-gp39 inhibits hyper Ig production, mice with GVHD were administered anti-gp39. On day 7 or 14, spleens were removed from control and treated mice. In vitro cultures of spleens from all test groups were assayed for the presence of IgG$_1$ and IgA. Spleens from mice with GVHD produced high levels of IgA and IgG$_1$ (FIGS. 38A and B). When GVHD mice were treated with anti-gp39 for 1 week, the levels of all IgG$_1$ and IgA returned to basal levels. The levels of both IgG$_1$ and IgA remained at basal levels for 1 week after termination of anti-gp39.

It was originally thought that a relevant control for these experiments would be equivalent treatment of GVHD-induced mice with hamster Ig (HIg) (i.p. 250 µg) but it was observed that an 8 fold increase was detected in the level of Ig produced by 1 week HIg treated GVHD-induced mice compared to untreated 1 week GVHD-induced mice. Also increased spleen cell counts were obtained in the HIg treated GVHD-induced mice compared to untreated GVHD-induced mice. Consequently it was decided to designate the untreated F$_1$ recipient mice as the control.

Reversal of splenomegaly and inhibition of hyper Ig production in GVH-induced mice by anti-gp39 administration, indicates that anti-gp39 blocked the ability of the grafted T cells to induce host B cell activation. This inhibition persists for 7 days even when the treatment is terminated. These results indicate that T cell function has been affected either by clonal deletion of the reactive T cells or that T cell anergy has occurred. Alternatively, inhibitory levels of anti-gp39 remain during this 7 day interval resulting in the blockade of Th effector function. This data indicates that anti-gp39 interferes with the ability of T cells to elicit a strong GVHD clinical immunopathology and splenomegaly.

Various publications are cited herein which are hereby incorporated by reference in their entirety.

What is claimed is:

1. A method of inhibiting B-cell activation comprising a mixture of B-cells and T cells to an effective concentration sufficient to reduce B-cell activation of a ligand that comprises a) at least a portion of the extracellular domain of a CD40 protein having a sequence as set forth in SEQ ID NO:1 attached to a second molecule wherein said second molecule is selected from the group consisting of peptides, proteins, carbohydrates and lipids and wherein the extracellular domain at the site of fusion has the amino acid sequence as set forth in SEQ ID NO:3 and b) being capable of specifically binding to a CD40 counter receptor (CD40CR) having a molecular weight of 39 kD as determined by SDS-PAGE under reducing conditions, and which CD40CR is expressed on activated T cells and binds to soluble CD40.

2. The method of claim 1 wherein the second molecule is at least a portion of an immunoglobulin molecule.

3. The method of claim 2 wherein the portion of an immunoglobulin molecule comprises a Fc fragment.

4. The method of claim 1 in which the ligand is CD40-Ig, as produced by the plasmid pCD40Ig depicted in FIG. 8B.

5. The method of claim 1 in which the ligand is capable of competitively inhibiting the binding of CD40 CD40CR.

6. The method of claim 1 in which the ligand is capable of competitively inhibiting the binding of monoclonal antibody MR1, as deposited with the ATCC having accession nunber HB11048, to its target antigen.

7. A method of reducing B-cell activation in a subject suffering from a disorder associated with B cell activation, comprising administering to the subject a therapeutically effective amount sufficient to reduce B cell activation of a ligand that comprises a) at least a portion of the extracellular domain of a CD40 protein having a sequence as set forth in SEQ ID NO:1 attached to a second molecule wherein said second molecule is selected fdrom the group consisting of peptides, proteins, carbohydrates and lipids and wherein the extracellular domain at the site of fusion has the amino acid sequence as set forth in SEQ ID NO:3 and b) being capable of specifically binding to a CD40 counter receptor (CD40CR) having a molecular weight of 39 kD as determined by SDS-PAGE under reducing conditions, and which CD40CR is expressed on activated T cells and binds to soluble CD40.

8. The method of claim 7 in wherein the second molecule is at least a portion of an immunoglobulin molecule.

9. The method of claim 8 wherein the portion of an immunoglobulin molecule comprises a Fc fragment.

10. The method of claim 7 in which the ligand is CD40-Ig, as produced by the Plasmid pCD40-Ig depicted in FIG. 8B.

11. The method of claim 7 in which the ligand is capable of competitively inhibiting the binding of CD40 to CD40CR.

12. The method of claim 7 in which the ligand is capable of competitively inhibiting the binding of monoclonal antibody MR1, as deposited with the ATCC having accession number HB11048, to its target antigen.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1004 base pairs
      (B) TYPE: nucleic acid
      (C) STRANDEDNESS: double (D) TOPOLOGY: unknown (ii) MOLECULE TYPE: cDNA (ix) FEATURE:
        (A) NAME/KEY: CDS
        (B) LOCATION: 48..878

(xi) SEQUENCE DESCRIPTION: SEQ ID NO:1:

```
GCCTCGCTCG GGCGCCCAGT GGTCCTGCCG CCTGGTCTCA CCTCGCC ATG GTT CGT            56
                                                     Met Val Arg
                                                       1

CTG CCT CTG CAG TGC GTC CTC TGG GGC TGC TTG CTG ACC GCT GTC CAT           104
Leu Pro Leu Gln Cys Val Leu Trp Gly Cys Leu Leu Thr Ala Val His
        5                   10                  15

CCA GAA CCA CCC ACT GCA TGC AGA GAA AAA CAG TAC CTA ATA AAC AGT           152
Pro Glu Pro Pro Thr Ala Cys Arg Glu Lys Gln Tyr Leu Ile Asn Ser
 20                  25                  30                  35

CAG TGC TGT TCT TTG TGC CAG CCA GGA CAG AAA CTG GTG AGT GAC TGC           200
Gln Cys Cys Ser Leu Cys Gln Pro Gly Gln Lys Leu Val Ser Asp Cys
                 40                  45                  50

ACA GAG TTC ACT GAA ACG GAA TGC CTT CCT TGC GGT GAA AGC GAA TTC           248
Thr Glu Phe Thr Glu Thr Glu Cys Leu Pro Cys Gly Glu Ser Glu Phe
             55                  60                  65

CTA GAC ACC TGG AAC AGA GAG ACA CAC TGC CAC CAG CAC AAA TAC TGC           296
Leu Asp Thr Trp Asn Arg Glu Thr His Cys His Gln His Lys Tyr Cys
         70                  75                  80

GAC CCC AAC CTA GGG CTT CGG GTC CAG CAG AAG GGC ACC TCA GAA ACA           344
Asp Pro Asn Leu Gly Leu Arg Val Gln Gln Lys Gly Thr Ser Glu Thr
     85                  90                  95

GAC ACC ATC TGC ACC TGT GAA GAA GGC TGG CAC TGT ACG AGT GAG GCC           392
Asp Thr Ile Cys Thr Cys Glu Glu Gly Trp His Cys Thr Ser Glu Ala
100                 105                 110                 115

TGT GAG AGC TGT GTC CTG CAC CGC TCA TGC TCG CCC GGC TTT GGG GTC           440
Cys Glu Ser Cys Val Leu His Arg Ser Cys Ser Pro Gly Phe Gly Val
                120                 125                 130

AAG CAG ATT GCT ACA GGG GTT TCT GAT ACC ATC TGC GAG CCC TGC CCA           488
Lys Gln Ile Ala Thr Gly Val Ser Asp Thr Ile Cys Glu Pro Cys Pro
            135                 140                 145

GTC GGC TTC TTC TCC AAT GTG TCA TCT GCT TTC GAA AAA TGT CAC CCT           536
Val Gly Phe Phe Ser Asn Val Ser Ser Ala Phe Glu Lys Cys His Pro
        150                 155                 160

TGG ACA AGC TGT GAG ACC AAA GAC CTG GTT GTG CAA CAG GCA GGC ACA           584
Trp Thr Ser Cys Glu Thr Lys Asp Leu Val Val Gln Gln Ala Gly Thr
    165                 170                 175

AAC AAG ACT GAT GTT GTC TGT GGT CCC CAG GAT CGG CTG AGA GCC CTG           632
Asn Lys Thr Asp Val Val Cys Gly Pro Gln Asp Arg Leu Arg Ala Leu
180                 185                 190                 195

GTG GTG ATC CCC ATC ATC TTC GGG ATC CTG TTT GCC ATC CTC TTG GTG           680
Val Val Ile Pro Ile Ile Phe Gly Ile Leu Phe Ala Ile Leu Leu Val
                200                 205                 210

CTG GTC TTT ATC AAA AAG GTG GCC AAG AAG CCA ACC AAT AAG GCC CCC           728
Leu Val Phe Ile Lys Lys Val Ala Lys Lys Pro Thr Asn Lys Ala Pro
            215                 220                 225

CAC CCC AAG CAG GAA CCC CAG GAG ATC AAT TTT CCC GAC GAT CTT CCT           776
His Pro Lys Gln Glu Pro Gln Glu Ile Asn Phe Pro Asp Asp Leu Pro
        230                 235                 240

GGC TCC AAC ACT GCT GCT CCA GTG CAG GAG ACT TTA CAT GGA TGC CAA           824
Gly Ser Asn Thr Ala Ala Pro Val Gln Glu Thr Leu His Gly Cys Gln
    245                 250                 255

CCG GTC ACC CAG GAG GAT GGC AAA GAG AGT CGC ATC TCA GTG CAG GAG           872
```

```
Pro Val Thr Gln Glu Asp Gly Lys Glu Ser Arg Ile Ser Val Gln Glu
260                 265                 270                 275

AGA CAG TGAGGCTGCA CCCACCCAGG AGTGTGGCCA CGTGGGCAAA CAGGCAGTTG         928
Arg Gln

GCCAGAGAGC CTGGTGCTGC TGCTGCAGGG GTGCAGGCAG AAGCGGGGAG CTATGCCCAG       988

TCAGTGCCAG CCCCTC                                                      1004

(2) INFORMATION FOR SEQ ID NO:2:

(i) SEQUENCE CHARACTERISTICS:
            (A) LENGTH: 277 amino acids
            (B) TYPE: amino acid
            (D) TOPOLOGY: linear (ii) MOLECULE TYPE: protein (xi) SEQUENCE DESCRIPTION: SEQ ID NO:2:

Met Val Arg Leu Pro Leu Gln Cys Val Leu Trp Gly Cys Leu Leu Thr
 1               5                  10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275
```